(12) United States Patent  
DiCosimo et al.

(10) Patent No.: US 8,222,012 B2  
(45) Date of Patent: *Jul. 17, 2012

(54) PERHYDROLASE FOR ENZYMATIC PERACID PRODUCTION

(75) Inventors: Robert DiCosimo, Chadds Ford, PA (US); John Edward Gavagan, Wilmington, DE (US); Mark Scott Payne, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 369 days.

This patent is subject to a terminal disclaimer.

(21) Appl. No.: 12/571,702

(22) Filed: Oct. 1, 2009

(65) Prior Publication Data

US 2011/0081693 A1    Apr. 7, 2011

(51) Int. Cl.
C12P 7/14       (2006.01)
C12N 9/14      (2006.01)
C12N 15/00    (2006.01)
C12N 1/21      (2006.01)

(52) U.S. Cl. .................. 435/136; 435/195; 435/252.3; 435/320.1

(58) Field of Classification Search .............. 435/136, 435/195, 252.3, 320.1
See application file for complete search history.

(56) References Cited

U.S. PATENT DOCUMENTS

| | | | |
|---|---|---|---|
| 3,974,082 A | 8/1976 | Weyn | |
| 4,444,886 A | 4/1984 | Esders et al. | |
| 4,585,150 A | 4/1986 | Beacham et al. | |
| 4,678,103 A | 7/1987 | Dirksing | |
| 5,116,575 A | 5/1992 | Badertscher et al. | |
| 5,152,461 A | 10/1992 | Proctor | |
| 5,281,525 A | 1/1994 | Mitsushima et al. | |
| 5,296,161 A | 3/1994 | Wiersema et al. | |
| 5,338,676 A | 8/1994 | Mitsushima et al. | |
| 5,364,554 A | 11/1994 | Stanislowski et al. | |
| 5,398,846 A | 3/1995 | Corba et al. | |
| 5,528,152 A | 6/1996 | Hinoshita et al. | |
| 5,532,157 A | 7/1996 | Fink | |
| 5,605,793 A | 2/1997 | Stemmer | |
| 5,624,634 A | 4/1997 | Brougham et al. | |
| 5,683,724 A | 11/1997 | Hei et al. | |
| 5,811,238 A | 9/1998 | Stemmer et al. | |
| 5,830,721 A | 11/1998 | Stemmer et al. | |
| 5,837,458 A | 11/1998 | Minshull et al. | |
| 5,862,949 A | 1/1999 | Markey et al. | |
| 5,932,532 A | 8/1999 | Ghosh et al. | |
| 5,954,213 A | 9/1999 | Gerhart et al. | |
| 6,183,807 B1 | 2/2001 | Gutzmann et al. | |
| 6,210,639 B1 | 4/2001 | Vlass et al. | |
| 6,223,942 B1 | 5/2001 | Markey et al. | |
| 6,319,888 B2 | 11/2001 | Wei et al. | |
| 6,391,840 B1 | 5/2002 | Thompson et al. | |
| 6,465,233 B1 | 10/2002 | Knauseder et al. | |
| 6,518,307 B2 | 2/2003 | McKenzie et al. | |
| 6,545,047 B2 | 4/2003 | Gutzmann et al. | |
| 6,635,286 B2 | 10/2003 | Hei et al. | |
| 6,645,233 B1 | 11/2003 | Ayers et al. | |
| 6,758,411 B2 | 7/2004 | Conway et al. | |
| 6,995,125 B2 | 2/2006 | Dasque et al. | |
| 7,448,556 B2 | 11/2008 | Muehlhausen et al. | |
| 7,951,566 B2 * | 5/2011 | DiCosimo et al. ............ 435/136 |
| 7,964,378 B2 * | 6/2011 | DiCosimo et al. ............ 435/136 |
| 8,030,038 B2 * | 10/2011 | DiCosimo et al. ............ 435/136 |
| 2002/0030063 A1 | 3/2002 | Leray et al. | |
| 2004/0127381 A1 | 7/2004 | Scialla et al. | |
| 2005/0008526 A1 | 1/2005 | Bianchetti et al. | |
| 2008/0176299 A1 | 7/2008 | DiCosimo et al. | |
| 2008/0176783 A1 | 7/2008 | DiCosimo et al. | |
| 2009/0005590 A1 | 1/2009 | DiCosimo et al. | |

FOREIGN PATENT DOCUMENTS

| | | |
|---|---|---|
| EP | 0807156 B1 | 11/1997 |
| WO | WO96/32149 | 10/1996 |
| WO | WO97/41833 | 11/1997 |
| WO | WO99/03984 | 1/1999 |
| WO | WO00/61713 | 10/2000 |
| WO | WO02/22467 | 3/2002 |
| WO | WO2005/035705 A2 | 4/2005 |
| WO | WO2007/070609 A2 | 6/2007 |
| WO | WO2007/106293 A1 | 9/2007 |
| WO | WO2008/073139 A1 | 6/2008 |

OTHER PUBLICATIONS

Copending U.S. Appl. No. 12/572,086, filed Oct. 1, 2009.
Copending U.S. Appl. No. 12/572,070, filed Oct. 1, 2009.
Copending U.S. Appl. No. 12/572,107, filed Oct. 1, 2009.
Copending U.S. Appl. No. 12/572,115, filed Oct. 1, 2009.
Belghith, Stabilization of Penicillium Occitanis Cellulases by Sray Drying in Presence .., Enzyme and Microbial Tech., 28 (2001) 253-258, XP-002558791.
Justus Liebigs Annalen der Chemie; 105:206 (1858).
Wurtz, Annales de Chimie; 55:443 (1859).
Seelig, Univ. of Berlin Laboratory; 24: 3466 (1891).
Stöchiometrie und Verwandtschaftslehre vol. 183, [K. Loskit, On the Knowledge of Triglycerides, p. 135-155], vol. 134, Nos. 1 and 2, May 1928.
Abbott et al., Physical Properties and Kinetic Behavior of a Cephalosporin . . . , Appl. Microbiol. 30(3):413-419 (1975).
Funasaki, N. et al., Intramolecular Hydrophobic Association of Two Alkyl Chains of Ollgoethylene Glycol Diethers and Diesters in Water, J. Phys. Chem. 88:5786-5790 (1984).

(Continued)

Primary Examiner — Tekchand Saidha

(57) ABSTRACT

A process is provided for rapidly producing target concentrations of peroxycarboxylic acids from carboxylic acid esters. More specifically, carboxylic acid esters are reacted with a source of peroxygen, such as hydrogen peroxide, in the presence of an enzyme catalyst comprising an enzyme having identity to an acetyl xylan esterase from *Lactococcus lactis* having perhydrolysis activity. The polypeptide is an enzyme structurally classified as a member of the carbohydrate esterase family 7 (CE-7). The peroxycarboxylic acids produced by the present process can be used in disinfecting, bleaching, and other laundry care applications. Compositions comprising the reaction components and the peroxycarboxylic acids produced by the process are also provided.

22 Claims, 2 Drawing Sheets

OTHER PUBLICATIONS

C. Laane et al., Rules for Optimization of Biocatalysis in Organic Solvents, Biotechnol. Bioeng, 30:81-87 (1987).
Cowan et al., Biocatalysis in Organic Phase Media., Ch. 7 in Biocatalysis at Extreme Temperatures . . . , Amer. Chem. Soc. Symposium Series 498, pp. 86-107 (1992).
Lee, Y.E. et al., Genetic Organization, Sequence and Biochemical Characterization of Recombinant . . . , J Gen Microbiol. (1993), 139:1235-1243.
Mitsushima et al Gene Cloning, Nucleotide Sequence, and Expression.., Appl. Env. Microbiol. 61(6):2224-2229, (1995).
Fromant et al., Direct Random Mutagenesis of Gene-Sized DNA Fragments Using Polymerase Chain Reaction, Analytical Biochemistry 224, 347-353 (1995).
Kobayashi et al., Purification and Properties of an Alkaline Protease from *Alkalophilic bacillus* sp. KSM-K16, Appl. Microbiol. Biotechnol. 43 (3), 473-481 (1995).
Kuo, S.-J. et al., Solvent Polarity Influences Product Selectivity of Lipase-Mediated Esterification Reactions in Microaqueous Media, J. Am. Oil Chem. Soc. 73:1427-1433 (1996).
Pinkernell, U. et al., Simultaneous HPLC Determination of Peroxyacetic Acid and Hydrogen Peroxide, Anal. Chem., 69(17):3623-3627 (1997).
Kunst et al., The Complete Genome Sequence of the Gram-Positive *Bacterium bacillus subtilis*, Nature 390:249-256 (1997).
Lin-Goerke et al., PCR-based Random Mutagenesis Using Manganese and Reduced dNTP Concentration, Biotechniques, 23(3):409-12 (1997).
Nixon et al., Assembly of an Active Enzyme by the Linkage of Two Protein Modules, PNAS, 94:1069-1073 (1997).
Lorenz et al., Isolation, Analysis and Expresion of Two Genes from *Thermoanaerobacterium* . . . , J. Bacteriol 179:5436-5441 (1997).
Politino et al., Purification and Characterization of a Cephalosporin Esterase . . . , Appl. Environ. Microbiol., 63(12):4807-4811 (1997).
Sakai et al., Purification and Properties of Cephalosporing-C Deacetylase from the Yeast . . . , J. Ferment. Bioeng. 85:53-57 (1998).
Gilbert et al., , Recent Advances in Carbohydrate Bioengineering, The Royal Society of Chemistry, Cambridge, pp. 3-12. (1999).
Nelson et al., Evidence for Lateral Gene Transfer Between Archaea and Bacteria From Genome Sequence of Thermotoga Maritime, Nature, 399:323-329 (1999).
Melnikov et al., Random Mutagenesis by Recombinational Capture of PCR Products in *Bacillus subtilis* and *Acinetobacter calcoaceticus*, Nucleic Acids Res. 27(4):1056-62 (1999).
Cardoza et al., A Cephalosporin C Acetylhydrolase is Present in the Cultures of Nocardia Lactamdurans, Appl. Microbiol. Biotechnol., 54(3):406-412 (2000).
Berman, H.M. et al., The Protein Data Bank. Nucleic Acids Research, 28 pp. 235-242 (2000).
Degrassi et al., The Acetyl Xyland Esterase of *Bacillus pumilus* Belongs to a Family . . . , Microbiology., 146:1585-1591 (2000).
Takami et al., Complete Genome Sequences of the Alkaliphilic Bacterium *Bacillus halodurans* and . . . , NAR, 28(21):4317-4331 (2000).
Gunning, Y. M. et al., Phase Behavior and Component Partitioning in Low Water Content Amorphous Carbohydrates . . ., J. Agric. Food Chem. 48:395-399 (2000).
Vincent et al., Multifunctional Xylooligosaccharide/Cephalosporin C Deacetylase . . . , J. Mol. Biol., 330:593-606 (2003).
Ru et al, On the Salt-Induced Activation of Lyophilized Enzyme in Organic Sovents, J. Am. Chem. Soc. vol. 122, No. 8, pp. 1465-1571, Feb. 9, 2000.
Ikeda et al., Complete Genome Sequence and Comparative Analysis of the Industrial Microorganism *Streptomyces avermitilis*, Nat. Biotechnol. 21 (5), 526-531 (2003).
H.M. Berman, Announcing the Worldwide Protein Data Bank, Nature Structural Biology 10 (12), p. 980 (2003).
Rey et al., Complete Genome Sequence of the Industrial Bacterium *Bacillus licheniformis* and . . . , Genome Biol., 5(10): article 77, R77.1-R77-12, (2004).
Braeken, L. et al., Modeling of the Adsorption of Organic Compounds on Polymeric Nanofiltration Membranes in Solutions Containing . . . , Chem Phys Chem, 6:1606-1612 (2005).
Castillo et al., On the Activity Loss of Hydrolases in Organic Solvents . . . , J. Mol. Catalysis Elsevier, vol. 35, No. 4-6, pp. 147-153, Sep. 1, 2005.
Krastanova et al., Heterologous Expression, Purificaiton, Crystallization, X-Ray Analysis and . . . , Biochimica ET Biophysica Acta, vol. 1748, No. 2, May 2005, pp. 222-230.
Serdakowski et al., Enzyme Activation for Organic Solvents Made Easy, Treads in Biotechnology, Trends in Biotechnology, Review, vol . 26, No. 1, pp. 48-54, Nov. 26, 2007.
Siezen et al., Genome-Scale Genotype-Phenotype Matching of Two *Lactococcus lactis* Isolates from Plants Identifies . . . , Appl. Environ. Microbiol. (2008) 74(2): 424-436).
Yoshii et al., Effects of protein on Retention of ADH enzyme Activity Encapsulated . . . , Journal of Food Engr., vol. 87, No. 1, pp. 34-39, Feb. 23, 2008.
DiCosimo, Thermophilic Perhydrolases for Peracetic Acid Production, Sim Annual Meeting and Exhibition, XP0002557717, Jul. 30, 2009.
Copending U.S. Appl. No. 11/638,635, filed Dec. 12, 2006.
Copending U.S. Appl. No. 12/143,375, filed Jun. 20, 2008.
Copending U.S. Appl. No. 12/539,025, filed Aug. 11, 2009.
Copending U.S. Appl. No. 12/572,059, filed Oct. 1, 2009.
Copending U.S. Appl. No. 12/572,094, filed Oct. 1, 2009.

* cited by examiner

SEQ ID NO: 2   MQLFDLPLDQLQTYKPEKTAPKDFSEFWKLSLEELAKVQAEPDLQPVDYPADGVKVYRLT
SEQ ID NO: 4   ----MTKINNWQDYQGSSLKPEDFDKFWDEKINLVSNHQFEFELIEKNLSSKVVNFYHLW
SEQ ID NO: 6   MPFPDLIQPELGAYVSSVGMPDDFAQFWTSTIAEARQAGGEVSIVQAQTTLKAVQSFDVT
SEQ ID NO: 8   ---MFDMPLAQLQKYMGTNPKPADFADFWSRALEELSAQSLHYELIPATFQTTVASCYHLY
SEQ ID NO:39   MAFFDMPLEELKKYRPERYEEKDFDEFWRETLKESEGFPLDPVFEKVDFHLKTVETYDVT
SEQ ID NO:40   MAFFDLPLEELKKYRPERYEEKDFDEFWEETLAESEKFPLDPVFERMESHLKTVEAYDVT
SEQ ID NO:41   MQLFDLSLEELKKYKPKKTARPDFSDFWKKSLEELRQVEAEPTLESYDYPVKGVKVYRLT

SEQ ID NO: 2   YKSFGNARITGWYAVPDK-QGPHPAIVKYHGYNASYDGEIHEMVNWALHGYAAFGMLVRG
SEQ ID NO: 4   FTAIDGAKIHAQLIVPKNLKEKYPAILQFHGYHCDS-GDWVDKIGIVAEGNVVLALDCRG
SEQ ID NO: 6   FPGYGGHPIKGWLILPTHHKGRLPLVVQYIGYGGGR-GLAHEQLHWAASGFAYFRMDTRG
SEQ ID NO: 8   FTGVGGARVHCQLVKPREQKQGPGLVWFHGYHTNS-GDWVDKLAYAAAGFTVLAMDCRG
SEQ ID NO:39   FSGYRGQRIKGWLLVPKLAEEKLPCVVQYIGYNGGR-GFPHDWLFWPSMGYICFVMDTRG
SEQ ID NO:40   FSGYRGQRIKGWLLVPKLEEEKLPCVVQYIGYNGGR-GFPHDWLFWPSMGYICFVMDTRG
SEQ ID NO:41   YQSFGHSKIEGFYAVPDQ-TGPHPALVRFHGYNASYDGGIHDIVNWALHGYATFGMLVRG

SEQ ID NO: 2   QQS--------SEDTSISLHG-HALGWMTKGILDK---DTYYYRGVYLDAVRALEVISSFDEV
SEQ ID NO: 4   QGG--------LSQDNIQTMGMTKGLIVRGIDEG---YENLYYVRQFMDLITATKILSEFDFV
SEQ ID NO: 6   QGSDWSVGETAD-PVGSTS--SIPGFMTRGVLDK---NDYYRRLFTDAVRAIDALLGLDFV
SEQ ID NO: 8   QGG--------KSEDNLQVKGPTLKGHIIRGIEDPNPHHLYYRNVFLDTVQAVRILCSMDHI
SEQ ID NO:39   QGSGWMKGDTPDYPEGPVDPQYPGFMTRGILDP---GTYYYRRVFVDAVRAVEAAISFPRV
SEQ ID NO:40   QGSGWLKGDTPDYPEGPVDPQYPGFMTRGILDP---RTYYYRRVFTDAVRAVEAAASFPQV
SEQ ID NO:41   QGG--------SEDTSVTPGG-HALGWMTKGILSK---DTYYYRGVYLDAVRALEVIQSFPEV

FIG. 1A

```
SEQ ID NO: 2   DETRIGVTGGSQGGGLTIAAAALSD-IPKAAVADYPYLSNFERAIDVALEQPYLEINSFF
SEQ ID NO: 4   DETNISAQGASQGGALAVACAALSP-LIKKVTATYPFLSDYRKAYELGAEESAFEELPYW
SEQ ID NO: 6   DPERIAVCGDSQGGGISLAVGGIDP-RVKAVMPDVPFLCDFPRAVQTAVRDPYLEIVRFL
SEQ ID NO: 8   DRERIGVYGASQGGALALACAALEPSVVKKAVVLYPFLSDYKRAQELDMKNTAYEEIHYY
SEQ ID NO:39   DSRKVVVAGGSQGGGIALAVSALSN-RVKALLCDVPFLCHFRRAVQLVDTHPYVEITNFL
SEQ ID NO:40   DQERIVIAGGSQGGIALAVSALSK-KAKALLCDVPFLCHFRRAVQLVDTHPYAEITNFL
SEQ ID NO:41   DEHRIGVIGGSQGGALAIAAAALSD-IPKVVVADYPYLSNFERAVDVALEQPYLEINSYF

SEQ ID NO: 2   RRNGSPE--TEVQAMKTLSYFDIMNLADRVKVPVLMSIGLIDKVTPPSTVFAAYNHLETE
SEQ ID NO: 4   FQFKDPLHLREDWFFNQLEYIDIQNLAPRIKAEVIWILGGKDTVVPPITQMAAYNKIQSK
SEQ ID NO: 6   AQHRE----KKAAVFETLNYFDCVNFARRSKAPALFSVALMDEVCPPSTVYGAFNAYAGE
SEQ ID NO: 8   FRFLDPTHEREEEVFYKLGYIDIQLLADRICADVLWAVALEDHICPPSTQFAVYNKIRSK
SEQ ID NO:39   KTHRD----KEEIVFRTLSYFDGVNFAARAKVPALFSVGLMDTICPPSTVFAAYNHYAGP
SEQ ID NO:40   KTHRD----KEEIVFRTLSYFDGVNFAARAKIPALFSVGLMDNICPPSTVFAAYNYYAGP
SEQ ID NO:41   RRNSDPK--VEEKAFETLSYFDLINLAGWVKQPTLMAIGLIDKITPPSTVFAAYNHLETD

SEQ ID NO: 2   KELKVYRYFGHEYIPAFQT-EKLAFFKQHLKG---------
SEQ ID NO: 4   KSLYVLPEYGHEYLPKISD---------WLRENQ-
SEQ ID NO: 6   KTITEYEFNNHEGGQGYQERQQMTWLSRLFGVG--
SEQ ID NO: 8   KDMVLFYEYGHEYLPTMGDRAYLFFCPIFFPIQKRNVK
SEQ ID NO:39   KEIRIYPYNNHEGGGSFQAIEQVKFLKRLFEEG------
SEQ ID NO:40   KEIRIYPYNNHEGGGSFQAVEQVKFLKKLFEKG------
SEQ ID NO:41   KDLKVYRYFGHEFIPAFQT-EKLSFLQKHLLLST-----
```

PERHYDROLASE FOR ENZYMATIC PERACID PRODUCTION

TECHNICAL FIELD

The invention relates to the field of peroxycarboxylic acid biosynthesis and in situ enzyme catalysis. Specifically, a process is provided to produce peroxycarboxylic acids using an enzyme catalyst comprising an enzyme having identity to an acetyl xylan esterase from *Lactococcus lactis* subsp. *lactis*.

BACKGROUND

Peroxycarboxylic acid compositions can be effective antimicrobial agents. Methods of using peroxycarboxylic acids to clean, disinfect, and/or sanitize hard surfaces, textiles, meat products, living plant tissues, and medical devices against undesirable microbial growth have been described (U.S. Pat. No. 6,545,047; U.S. Pat. No. 6,183,807; U.S. Pat. No. 6,518,307; U.S. Patent Application Publication No. 20030026846; and U.S. Pat. No. 5,683,724). Peroxycarboxylic acids have also used in a various laundry care applications, such as their use as bleaching agents (U.S. Pat. No. 3,974,082; U.S. Pat. No. 5,296,161; and U.S. Pat. No. 5,364,554).

Peroxycarboxylic acids can be prepared by the chemical reaction of a carboxylic acid alkyl ester and a peroxide reagent, such as hydrogen peroxide (see *Organic Peroxides*, Daniel Swern, ed., Vol. 1, pp 313-516; Wiley Interscience, New York, 1971). However, under slightly basic to acidic pH (from about 8 to about 4) the reaction often does not proceed rapidly enough to produce a peroxycarboxylic acid concentration that is suitable for many commercial disinfecting and/or bleaching applications.

One way to overcome the disadvantages of chemical peroxycarboxylic acid production is to use an enzyme catalyst having perhydrolysis activity. U.S. patent application Ser. No. 11/638,635 and U.S. Patent Application Publication Nos. 2008/0176783; 2008/0176299; and 2009/0005590 to DiCosimo et al. disclose enzymes structurally classified as members of the CE-7 family of carbohydrate esterases (e.g., cephalosporin C deacetylases [CAHs] and acetyl xylan esterases [AXEs]) that are characterized by significant perhydrolysis activity for converting carboxylic acid esters (in the presence of a suitable source of peroxygen, such as hydrogen peroxide) into peroxycarboxylic acids at concentrations sufficient for use as a disinfectant and/or a bleaching agent. Some members of the CE-7 family of carbohydrate esterases have been demonstrated to have perhydrolytic activity sufficient to produce 4000-5000 ppm peracetic acid from acetyl esters of alcohols, diols, and glycerols in 1 min and up to 9000 ppm between 5 minutes and 30 minutes once the reaction components were mixed (DiCosimo et al., U.S. Patent Application Publication No. 2009/0005590). CE-7 perhydrolases will often produce increasing concentrations of peracids after 30 minutes or more under suitable aqueous reaction conditions that include excess substrate, a pH of about 6.0 to about 8.5, and suitable temperature range. Typically the pH of the reaction is maintained using an effective amount of at least one buffer. The amount of peroxyacetic acid produced using such conditions may exceed that which is desirable or may take too long to eventually reach an efficacious concentration for certain applications.

Enzymatic production of peroxycarboxylic acids (e.g., peracetic acid) is typically conducted using aqueous reaction conditions. As such, hydrolysis reactions (chemical and/or enzymatic) often occur that produce the corresponding carboxylic acid (e.g., acetic acid) from the hydrolysis of the ester substrate and/or hydrolysis of the peroxycarboxylic acid, thereby destroying the desired product. The products of enzymatic perhydrolysis (peroxycarboxylic acid or a mixture of the peroxycarboxylic acid and the corresponding carboxylic acid hydrolysis product) can be corrosive to certain metal surfaces. As such, it may be desirable to limit the total amount of peroxycarboxylic acid produced during the reaction to prevent or minimize the corrosive effect of the resulting solution. For example, applications that require production of no more than 200 ppm to 1000 ppm of peracid in 1 minute often employ reaction conditions that yield a final concentration of peracid well above these limits. In an application for in situ generation of peracid for disinfection of hard surfaces, it is desirable to have the ability to rapidly generate the desired concentration of peracid without significantly exceeding the upper efficacious disinfectant concentration, thereby limiting or preventing the corrosion of certain components of the surface. In an application for in situ generation of peracid for bleaching of laundry or textiles, similar limitations to the concentration of peracid generated above that required for bleaching are also desirable. As such, there is a need to provide a process to rapidly produce a desired "target" concentration of peroxycarboxylic acid, especially in the presence of excess substrate.

Many CE-7 carbohydrate esterases exhibit a decrease or inactivation in perhydrolysis activity when the pH drops below about 6.0 with most of the CE-7 perhydrolases inactivated at or below a pH of 5.0. U.S. patent application Ser. No. 12/539,025 to DiCosimo et al. teaches a process to produce a desired "target" concentration of peroxycarboxylic acid by selecting reaction components and conditions whereby reaction products are formed (i.e., the peroxycarboxylic acid and the corresponding carboxylic acid hydrolysis product) that drop the pH of the reaction mixture to value where the enzyme catalyst has little or no perhydrolysis activity. The reaction components and conditions are selected whereby the pH of the reaction mixture drops below 6.0 within 10 minutes or less, enabling one to control the concentration of peroxycarboxylic acid produced. However, a product mixture having a pH of less than 6.0 may not be desirable for some disinfecting and/or bleaching applications, especially when the surface in contact with the reaction products is susceptible to corrosion and excessive bleaching. Under such circumstances, there remains a need to control the amount of enzymatically produced peroxycarboxylic acid that is not dependent on a substantial drop in the pH of the reaction mixture.

The problem to be solved is to provide a process to enzymatically produce a desired concentration of peroxycarboxylic acid in an aqueous reaction mixture that is not dependent upon a significant drop in pH or a pH of less than 6.0. The selected reaction components and reaction conditions should be capable of rapidly producing the desired peroxycarboxylic acid at a concentration that does not substantially increase once the target concentration is achieved.

SUMMARY

The stated problem has been solved by the discovery of an enzymatic process to produce a desired concentration of peroxycarboxylic acid in 5 minutes or less that does not substantially increase once the desired concentration is achieved; wherein the pH of the reaction mixture is maintained between 6.0 and 9.0 over the course of the reaction. The process includes the use of an enzyme catalyst comprising an enzyme having perhydrolysis activity, said enzyme having at least 95% identity to an acetyl xylan esterase from *Lactococcus lactis* subsp. *lactis*. The present enzyme catalyst enables rapid production of a product mixture having a substantially stable target concentration of peroxycarboxylic acid concentration in 5 minutes or less, even in the presence of excess of substrate and a pH range of 6.0 to 9.0; conditions where other CE-7 perhydrolases typically produce substantially increasing concentrations of peroxycarboxylic acids after 5 minutes or more.

In one embodiment, a process for producing a target concentration of a peroxycarboxylic acid is provided comprising:
a) selecting a set of reaction components comprising:
1) at least one substrate selected from the group consisting of:
i) esters having the structure

wherein;
X=an ester group of the formula $R_6$—C(O)O;
$R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;
$R_5$=a C1 to C6 linear, branched, or cyclic hydrocarbyl moiety optionally substituted with hydroxyl groups; wherein each carbon atom in $R_5$ individually comprises no more than one hydroxyl group or no more than one ester group; wherein $R_5$ optionally comprises one or more ether linkages;
m=1 to the number of carbon atoms in $R_5$; and
wherein said esters have solubility in water of at least 5 ppm at 25° C.;
ii) glycerides having the structure

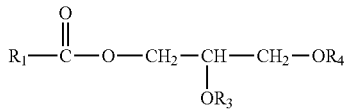

wherein $R_1$=$C_1$ to $C_7$ straight chain or branched chain alkyl optionally substituted with an hydroxyl or a C1 to C4 alkoxy group and $R_3$ and $R_4$ are individually H or $R_1$C(O); and
iii) acetylated saccharides selected from the group consisting of acetylated monosaccharides, acetylated disaccharides, and acetylated polysaccharides;
2) a source of peroxygen; and
3) an enzyme catalyst having perhydrolysis activity, wherein said enzyme catalyst comprises an enzyme having a signature motif that aligns with a reference sequence SEQ ID NO:2 using CLUSTALW, said signature motif comprising:
i) an RGQ motif at amino acid positions 118-120 of SEQ ID NO:2;
ii) a GXSQG motif at amino acid positions 179-183 of SEQ ID NO:2; and
iii) an HE motif at amino acid positions 298-299 of SEQ ID NO:2;
wherein said enzyme has at least 95% amino acid identity to SEQ ID NO:4; and
b) combining the reaction components under aqueous reactions to form a reaction mixture; whereby reaction products are formed comprising enzymatically-produced peroxycarboxylic acid; wherein
1) the pH of the reaction mixture remains in the range of from about 6.0 to about 9.0; and
2) the concentration of peroxycarboxylic acid produced one minute after combining the reaction components is not exceeded by more than 100% at a reaction time equal to or greater than five minutes after combining the reaction components.

In another embodiment, a process for producing a peroxycarboxylic acid is provided comprising:
a) selecting a set of reaction components comprising:
1) at least one substrate selected from the group consisting of:
i) esters having the structure

wherein
X=an ester group of the formula $R_6$—C(O)O;
$R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;
$R_5$=a C1 to C6 linear, branched, or cyclic hydrocarbyl moiety optionally substituted with hydroxyl groups; wherein each carbon atom in $R_5$ individually comprises no more than one hydroxyl group or no more than one ester group; wherein $R_5$ optionally comprises one or more ether linkages;
m=1 to the number of carbon atoms in $R_5$; and
wherein said esters have solubility in water of at least 5 ppm at 25° C.;
ii) glycerides having the structure

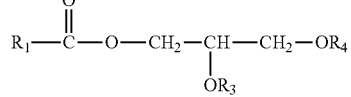

wherein $R_1$=$C_1$ to $C_7$ straight chain or branched chain alkyl optionally substituted with an hydroxyl or a C1 to C4 alkoxy group and $R_3$ and $R_4$ are individually H or $R_1$C(O); and
iii) acetylated saccharides selected from the group consisting of acetylated monosaccharides, acetylated disaccharides, and acetylated polysaccharides;
2) a source of peroxygen; and
3) an enzyme catalyst having perhydrolysis activity, wherein said enzyme catalyst comprises an enzyme having a signature motif that aligns with a reference sequence SEQ ID NO:2 using CLUSTALW, said signature motif comprising:
(i) an RGQ motif at amino acid positions 118-120 of SEQ ID NO:2;
(ii) a GXSQG motif at amino acid positions 179-183 of SEQ ID NO:2; and
(iii) an HE motif at amino acid positions 298-299 of SEQ ID NO:2;
wherein said enzyme has at least 95% amino acid identity to SEQ ID NO:4; and
b) combining the reaction components under aqueous reactions to form a reaction mixture; whereby reaction products are formed comprising enzymatically-produced peroxycarboxylic acid; wherein
1) the pH of the reaction mixture remains in the range of from about 6.0 to about 9.0; and
2) the concentration of peroxycarboxylic acid produced one minute after combining the reaction components is not exceeded by more than 100% at a reaction time equal to or greater than 30 minutes after combining the reaction components.

In another aspect, a composition comprising is also provided comprising:
a) a set of reaction components comprising:
1) at least one substrate selected from the group consisting of:
  i) esters having the structure

wherein
  X=an ester group of the formula $R_6$—C(O)O;
  $R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;
  $R_5$=a C1 to C6 linear, branched, or cyclic hydrocarbyl moiety optionally substituted with hydroxyl groups; wherein each carbon atom in $R_5$ individually comprises no more than one hydroxyl group or no more than one ester group; wherein $R_5$ optionally comprises one or more ether linkages;
  m=1 to the number of carbon atoms in $R_5$; and
  wherein said esters have solubility in water of at least 5 ppm at 25° C.;
  ii) glycerides having the structure

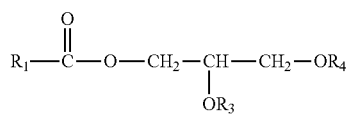

wherein $R_1$=$C_1$ to $C_7$ straight chain or branched chain alkyl optionally substituted with an hydroxyl or a C1 to C4 alkoxy group and $R_3$ and $R_4$ are individually H or $R_1$C(O); and
  iii) acetylated saccharides selected from the group consisting of acetylated monosaccharides, acetylated disaccharides, and acetylated polysaccharides;
2) a source of peroxygen; and
3) an enzyme catalyst having perhydrolysis activity, wherein said enzyme catalyst comprises an enzyme having a signature motif that aligns with a reference sequence SEQ ID NO:2 using CLUSTALW, said signature motif comprising:
  i) an RGQ motif at amino acid positions 118-120 of SEQ ID NO:2;
  ii) a GXSQG motif at amino acid positions 179-183 of SEQ ID NO:2; and
  iii) an HE motif at amino acid positions 298-299 of SEQ ID NO:2;
  wherein said enzyme also has at least 95% amino acid identity to SEQ ID NO:4; and
b) at least one peroxycarboxylic acid formed upon combining the set of reaction components of (a).

The present process produces the desired peroxycarboxylic acid upon combining the reaction components. The reaction components may remain separated until use. In further aspect, a kit comprising the reaction components is also provided comprising:
a) a first compartment comprising
1) an enzyme catalyst comprising an enzyme having at least 95% amino acid identify to SEQ ID NO: 4;
2) at least one substrate selected from the group consisting of:
  i) esters having the structure

wherein
  X=an ester group of the formula $R_6$—C(O)O;
  $R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;
  $R_5$=a C1 to C6 linear, branched, or cyclic hydrocarbyl moiety optionally substituted with hydroxyl groups; wherein each carbon atom in $R_5$ individually comprises no more than one hydroxyl group or no more than one ester group; wherein $R_5$ optionally comprises one or more ether linkages;
  m=1 to the number of carbon atoms in $R_5$; and
  wherein said esters have solubility in water of at least 5 ppm at 25° C.;
  ii) glycerides having the structure

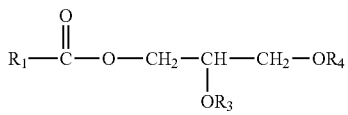

wherein $R_1$=$C_1$ to $C_7$ straight chain or branched chain alkyl optionally substituted with an hydroxyl or a C1 to C4 alkoxy group and $R_3$ and $R_4$ are individually H or $R_1$C(O); and
  iii) acetylated saccharides selected from the group consisting of acetylated monosaccharides, acetylated disaccharides, and acetylated polysaccharides; and
3) an optional buffer; and
b) a second compartment comprising
1) source of peroxygen;
2) a peroxide stabilizer; and
3) an optional buffer.

BRIEF DESCRIPTION OF THE FIGURE

FIGS. 1A and 1B show the results of a CLUSTALW alignment (version 1.83) of several enzymes having perhydrolase activity including the *Bacillus subtilis* ATCC® 31954™ cephalosporin C deacetylase reference sequence (SEQ ID NO: 2), a *Lactococcus lactis* subsp. *lactis* acetyl xylan esterase (SEQ ID NO: 4), a *Mesorhizobium loti* acetyl xylan esterase (SEQ ID NO: 6), a *Geobacillus stearothermophilus* acetyl xylan esterase, a *Thermotoga neapolitana* acetyl xylan esterase (SEQ ID NO: 39), a *Thermotoga maritima* acetyl xylan esterase (SEQ ID NO: 40), and a *Bacillus pumilus* acetyl xylan esterase (SEQ ID NO: 41). All of the enzymes have perhydrolase activity and are structurally classified members of the carbohydrate esterase family 7 (CE-7), sharing the conserved submotifs (underlined) that together form the signature motif for all CE-7 carbohydrate esterases (see Vincent et al., *J. Mol. Biol.*, 330:593-606 (2003) and U.S. Patent Application Publication No. 2008/0176783 to DiCosimo et al.).

BRIEF DESCRIPTION OF THE BIOLOGICAL SEQUENCES

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. §1.822.

SEQ ID NO: 1 is the nucleic acid sequence encoding the cephalosporin C deacetylase from *Bacillus subtilis* ATCC® 31954™ (GENBANK® accession number D10935).

SEQ ID NO: 2 is the amino acid sequence of the cephalosporin C deacetylase from *Bacillus subtilis* ATCC® 31954™.

SEQ ID NO: 3 is the nucleic acid sequence encoding the acetyl xylan esterase from *Lactococcus lactis* (GENBANK® accession number EU255910).

SEQ ID NO: 4 is the amino acid sequence of the acetyl xylan esterase from *Lactococcus lactis* (GENBANK® accession number ABX75634.1).

SEQ ID NO: 5 is the nucleic acid sequence encoding the acetyl xylan esterase from *Mesorhizobium loti* (GENBANK® accession number NC_002678.2).

SEQ ID NO: 6 is the amino acid sequence of the acetyl xylan esterase from *Mesorhizobium loti* (GENBANK® accession number BAB53179.1).

SEQ ID NO: 7 is the nucleic acid sequence encoding the acetyl xylan esterase from *Geobacillus stearothermophilus* (GENBANK® accession number AF038547.2).

SEQ ID NO: 8 is the amino acid sequence of the acetyl xylan esterase from *Geobacillus stearothermophilus* (GENBANK® accession number AAF70202.1).

SEQ ID NO: 9 is the nucleic acid sequence of a kanamycin resistance gene.

SEQ ID NO: 10 is the nucleic acid sequence of plasmid pKD13.

SEQ ID NOs: 11 and 12 are primers used to generate a PCR product encoding the kanamycin gene flanked by regions having homology to the katG catalase gene in *E. coli* MG1655. The product was used to disrupt the endogenous katG gene.

SEQ ID NO: 13 is the nucleic acid sequence of the PCR product encoding the kanamycin resistance gene flanked by regions having homology to the katG catalase gene in *E. coli* MG1655. The product was used to disrupt the endogenous katG gene.

SEQ ID NO: 14 is the nucleic acid sequence of the katG catalase gene in *E. coli* MG1655.

SEQ ID NO: 15 is the deduced amino acid sequence of the KatG catalase in *E. coli* MG1655.

SEQ ID NO: 16 is the nucleic acid sequence of plasmid pKD46.

SEQ ID NOs: 17 and 18 are primers used to confirm the disruption of the katG gene.

SEQ ID NO: 19 is the nucleic acid sequence of plasmid pCP20.

SEQ ID NO: 20 and 21 are primers used to generate a PCR product encoding the kanamycin gene flanked by regions having homology to the katE catalase gene in *E. coli* MG1655. The product was used to disrupt the endogenous katE gene.

SEQ ID NO: 22 is the nucleic acid sequence of the PCR product encoding the kanamycin resistance gene flanked by regions having homology to the katE catalase gene in *E. coli* MG1655. The product was used to disrupt the endogenous katE gene.

SEQ ID NO: 23 is the nucleic acid sequence of the katE catalase gene in *E. coli* MG1655.

SEQ ID NO: 24 is the deduced amino acid sequence of the KatE catalase in *E. coli* MG1655.

SEQ ID NOs: 25 and 26 are primers used to confirm disruption of the katE gene in the single knockout strain *E. coli* MG1655 ΔkatE, and in the double-knockout strain *E. coli* MG1655 ΔkatG ΔkatE, herein referred to as *E. coli* KLP18.

SEQ ID NO: 27 and 28 are the PCR primers used to generate a PCR product encoding a codon optimized version of the *Lactococcus lactis* acetyl xylan esterase subcloned in pTrcHis2-TOPO® to generate the plasmid identified as pSW229.

SEQ ID NO: 29 is the nucleic acid sequence of the PCR product in plasmid pSW229.

SEQ ID NO: 30 is the nucleic acid sequence of plasmid pSW229.

SEQ ID NO: 31 and 32 are the PCR primers used to generate a PCR product encoding a codon optimized version of the *Mesorhizobium loti* acetyl xylan esterase subcloned in pTrcHis2-TOPO® to generate the plasmid identified as pSW231.

SEQ ID NO: 33 is the nucleic acid sequence of the PCR product in plasmid pSW231.

SEQ ID NO: 34 is the nucleic acid sequence of plasmid pSW231.

SEQ ID NO: 35 and 36 are the PCR primers used to generate a PCR product encoding a codon optimized version of the *Geobacillus stearothermophilus* acetyl xylan esterase subcloned in pTrcHis2-TOPO® to generate the plasmid identified as pSW236.

SEQ ID NO: 37 is the nucleic acid sequence of the PCR product in plasmid pSW236.

SEQ ID NO: 38 is the nucleic acid sequence of plasmid pSW236.

SEQ ID NO: 39 is the amino acid sequence of a *Thermotoga neepolitana* enzyme having perhydrolysis activity (U.S. Patent Application Publication No. 2008-0176299; GENBANK® AAB70869.1).

SEQ ID NO: 40 is the amino acid sequence of a *Thermotoga maritima* enzyme having perhydrolysis activity (U.S. Patent Application Publication No. 2008-0176299; GENBANK® NP_227893.1).

SEQ ID NO: 41 is the amino acid sequence of a *Bacillus pumilus* enzyme having perhydrolysis activity (U.S. Patent Application Publication No. 2008-0176299; Degrassi et al., *Microbiology*, 146:1585-1591 (2000)).

DETAILED DESCRIPTION OF ILLUSTRATIVE EMBODIMENTS

A process is provided to produce a peroxycarboxylic acid by combining a substrate, a source of peroxygen, and an enzyme catalyst having perhydrolysis activity, wherein the enzyme catalyst comprises an enzyme having a CE-7 signature motif and at least 95% amino acid identity to SEQ ID NO: 4. The enzyme catalyst, when combined with the other reaction components, is characterized by a high initial rate of peroxycarboxylic acid production followed by a rapid decrease and/or loss in perhydrolysis activity when conducting the reaction in an aqueous reaction mixture that remains within a pH range of about 6.0 to about 9.0. The combination of these features facilitates the rapid production of a peroxycarboxylic acid concentration (the "target" concentration) that does not substantially increase once the desired peracid concentration is formed.

It is understood that the amount of peroxycarboxylic acid produced by the present process is not limited by the amount of substrate or the amount of peroxygen in the reaction mixture. In this way, one can control the amount of peroxycarboxylic acid produced by using the present enzyme catalyst under the reaction conditions described herein, conditions where other CE-7 enzymes having perhydrolysis activity typically continue to produce peroxycarboxylic acid at concentrations that substantially increase more than 5 minutes after combining the reaction components.

The peroxycarboxylic acid produced by the present process may be used in a variety of applications including, but not limited to, disinfecting, bleaching, or providing a benefit to textiles for laundry care applications that may also include (in addition to disinfecting and bleaching) destaining, deodorizing and combinations thereof. The present process is particularly attractive for use in applications where an excessive amount of peroxycarboxylic acid and/or a pH below 6.0 may have an undesirable effect, such as corrosion or excessive bleaching.

In this disclosure, a number of terms and abbreviations are used. The following definitions apply unless specifically stated otherwise.

As used herein, the term "comprising" means the presence of the stated features, integers, steps, or components as referred to in the claims, but does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the term "peroxycarboxylic acid" is synonymous with peracid, peroxyacid, peroxy acid, percarboxylic acid and peroxoic acid.

As used herein, the term "peracetic acid" is abbreviated as "PAA" and is synonymous with peroxyacetic acid, ethaneperoxoic acid and all other synonyms of CAS Registry Number 79-21-0.

As used herein, the term "monoacetin" is synonymous with glycerol monoacetate, glycerin monoacetate, and glyceryl monoacetate.

As used herein, the term "diacetin" is synonymous with glycerol diacetate; glycerin diacetate, glyceryl diacetate, and all other synonyms of CAS Registry Number 25395-31-7.

As used herein, the term "triacetin" is synonymous with glycerin triacetate; glycerol triacetate; glyceryl triacetate, 1,2,3-triacetoxypropane, 1,2,3-propanetriol triacetate and all other synonyms of CAS Registry Number 102-76-1.

As used herein, the term "monobutyrin" is synonymous with glycerol monobutyrate, glycerin monobutyrate, and glyceryl monobutyrate.

As used herein, the term "dibutyrin" is synonymous with glycerol dibutyrate and glyceryl dibutyrate.

As used herein, the term "tributyrin" is synonymous with glycerol tributyrate, 1,2,3-tributyrylglycerol, and all other synonyms of CAS Registry Number 60-01-5.

As used herein, the term "monopropionin" is synonymous with glycerol monopropionate, glycerin monopropionate, and glyceryl monopropionate.

As used herein, the term "dipropionin" is synonymous with glycerol dipropionate and glyceryl dipropionate.

As used herein, the term "tripropionin" is synonymous with glyceryl tripropionate, glycerol tripropionate, 1,2,3-tripropionylglycerol, and all other synonyms of CAS Registry Number 139-45-7.

As used herein, the term "ethyl acetate" is synonymous with acetic ether, acetoxyethane, ethyl ethanoate, acetic acid ethyl ester, ethanoic acid ethyl ester, ethyl acetic ester and all other synonyms of CAS Registry Number 141-78-6.

As used herein, the term "ethyl lactate" is synonymous with lactic acid ethyl ester and all other synonyms of CAS Registry Number 97-64-3.

As used herein, the terms "acetylated sugar" and "acetylated saccharide" refer to mono-, di- and polysaccharides comprising at least one acetyl group. Examples include, but are not limited to, glucose pentaacetate, xylose tetraacetate, acetylated xylan, acetylated xylan fragments, β-D-ribofuranose-1,2,3,5-tetraacetate, tri-O-acetyl-D-galactal, and tri-O-acetyl-glucal.

As used herein, the terms "hydrocarbyl", "hydrocarbyl group", and "hydrocarbyl moiety" mean a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, pentyl, cyclopentyl, methylcyclopentyl, hexyl, cyclohexyl, benzyl, and phenyl. In a preferred embodiment, the hydrocarbyl moiety is a straight chain, branched or cyclic arrangement of carbon atoms connected by single carbon to carbon bonds and/or by ether linkages, and substituted accordingly with hydrogen atoms.

As used herein, the terms "monoesters" and "diesters" of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,6-pentanediol, 1,2-hexanediol, 2,5-hexanediol, 1,6-hexanediol, refer to said compounds comprising at least one ester group of the formula RC(O)O, wherein R is a C1 to C7 linear hydrocarbyl moiety. In one embodiment, the substrate comprises propylene glycol diacetate (PGDA), ethylene glycol diacetate (EGDA) or a mixture thereof.

As used herein, the terms "suitable enzymatic reaction mixture", "components suitable for generation of a peroxycarboxylic acid", "suitable reaction components", "reaction components", "reaction mixture", and "suitable aqueous reaction mixture" refer to the materials and water in which the reactants and the present enzyme catalyst come into contact. The components of the reaction mixture are provided herein and those skilled in the art appreciate the range of component variations suitable for this process. In one embodiment, the enzymatic reaction mixture produces peroxycarboxylic acid in situ upon combining the reaction components. As such, the reaction components may be provided as a multicomponent system wherein one or more of the reaction components remains separated until use. The design of systems and means for separating and combining multiple active components are known in the art and generally will depend upon the physical form of the individual reaction components. For example, multiple active fluids (liquid-liquid) systems typically use multichamber dispenser bottles or two-phase systems (U.S. Patent Application Pub. No. 2005/0139608; U.S. Pat. No. 5,398,846; U.S. Pat. No. 5,624,634; U.S. Pat. No. 6,391,840; E.P. Patent 0807156B1; U.S. Patent Appln. Pub. No. 2005/0008526; and PCT Publication No. WO 00/11713A1) such as found in some bleaching applications wherein the desired bleaching agent is produced upon mixing the reactive fluids. Other forms of multicomponent systems used to generate peroxycarboxylic acid may include, but are not limited to, those designed for one or more solid components or combinations of solid-liquid components, such as powders (e.g., many commercially available bleaching composition, U.S. Pat. No. 5,116,575), multi-layered tablets (U.S. Pat. No. 6,210,639), water dissolvable packets having multiple compartments (U.S. Pat. No. 6,995,125) and solid agglomerates that react upon the addition of water (U.S. Pat. No. 6,319,888).

As used herein, the term "substrate" will refer to the reaction components enzymatically perhydrolyzed using the present enzyme catalyst in the presence of a suitable source of peroxygen, such as hydrogen peroxide. In one embodiment, the substrate comprises at least one ester group capable of being enzymatically perhydrolyzed using the present enzyme catalyst, whereby a peroxycarboxylic acid is produced. In a further embodiment, the present process comprises reaction components and conditions wherein a substantially stable target concentration of peroxycarboxylic acid produced is achieved in the presence of excess substrate.

As used herein, the term "reaction products" will refer to the mixture of compounds formed within the reaction mixture after combining the selected reaction components. The reaction products are comprised of the enzymatically-generated peroxycarboxylic acid (e.g., peracetic acid) as well as one or more hydrolysis products (enzymatic and/or chemical hydrolysis products), such as the corresponding carboxylic acid (e.g., acetic acid). In one embodiment, combining the selected set of reaction components generates a reaction mixture capable of forming reaction products that substantially decrease and/or inactivate the perhydrolysis catalyst within 10 minutes of combining the reaction components, preferably within about 1 minute to about 10 minutes, wherein the pH of the reaction mixture is maintained between 6.0 and 9.0, preferably between 6.5 and 8.0, until the desired target concentration of peroxycarboxylic acid is achieved. In one embodiment, the perhydrolysis activity of the enzyme catalyst is reduced at least 80% in 10 minutes or less after combining the reaction components.

As used herein, the term "perhydrolysis" is defined as the reaction of a selected substrate with a source of hydrogen peroxide to form a peroxycarboxylic acid. Typically, inorganic peroxide is reacted with the selected substrate in the presence of a catalyst to produce the peroxycarboxylic acid. As used herein, the term "chemical perhydrolysis" includes perhydrolysis reactions in which a substrate (a peroxycarboxylic acid precursor) is combined with a source of hydrogen peroxide wherein peroxycarboxylic acid is formed in the absence of an enzyme catalyst. As used herein, the term "enzymatic perhydrolysis" refers a reaction of a selected substrate with a source of hydrogen peroxide to form a peroxycarboxylic acid, wherein the reaction is catalyzed by an enzyme catalyst having perhydrolysis activity.

As used herein, the term "perhydrolase activity" refers to the enzyme catalyst activity per unit mass (for example, milligram) of protein, dry cell weight, or immobilized catalyst weight.

As used herein, "one unit of enzyme activity" or "one unit of activity" or "U" is defined as the amount of perhydrolase activity required for the production of 1 µmol of peroxycarboxylic acid product per minute at a specified temperature.

As used herein, the terms "enzyme catalyst" and "perhydrolase catalyst" refer to a catalyst comprising an enzyme having perhydrolysis activity and may be in the form of a whole microbial cell, permeabilized microbial cell(s), one or more cell components of a microbial cell extract, partially purified enzyme, or purified enzyme. The enzyme catalyst may also be chemically modified (e.g., by pegylation or by reaction with cross-linking reagents). The perhydrolase catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. As described herein, the present enzyme having perhydrolysis activity is structurally classified as a member of the carbohydrate family esterase family 7 (CE-7 family) of enzymes (see Coutinho, P. M., Henrissat, B. "Carbohydrate-active enzymes: an integrated database approach" in *Recent Advances in Carbohydrate Bioengineering*, H. J. Gilbert, G. Davies, B. Henrissat and B. Svensson eds., (1999) The Royal Society of Chemistry, Cambridge, pp. 3-12.). The present CE-7 perhydrolase catalyst comprises an enzyme having amino acid sequence SEQ ID NO: 4 or an enzyme substantially similar to SEQ ID NO: 4. Means to identify substantially similar biological molecules are well known in the art (e.g. sequence alignment protocols, nucleic acid hybridizations, presence of a conserved signature motif, etc.). In one aspect, the enzyme catalyst in the present process comprises a substantially similar enzyme having at least 95%, 96%, 97%, 98%, or 99% amino acid identity to SE ID NO: 4. The nucleic acid molecules encoding the present enzymes having perhydrolysis activity are also provided herein. In a further embodiment, the perhydrolase catalyst useful in the present process is encoded by a nucleic acid molecule that hybridizes stringent conditions to a nucleic acid molecule encoding a polypeptide having amino acid sequence SEQ ID NO: 4.

As used herein, the terms "cephalosporin C deacetylase" and "cephalosporin C acetyl hydrolase" refer to an enzyme (E.C. 3.1.1.41) that catalyzes the deacetylation of cephalosporins such as cephalosporin C and 7-aminocephalosporanic acid (Mitsushima et al., *Appl. Environ. Microbial.*, 61(6): 2224-2229 (1995); U.S. Pat. No. 5,528,152; and U.S. Pat. No. 5,338,676). Enzymes classified as cephalosporin C deacetylases have been shown to often have significant perhydrolase activity (DiCosimo et al., U.S. Patent Application Publication No. 2008/0176783).

As used herein, "acetyl xylan esterase" "refers to an enzyme (E.C. 31.1.72; AXEs) that catalyzes the deacetylation of acetylated xylans and other acetylated saccharides. Enzymes classified as acetyl xylan esterases have been shown to have perhydrolase activity (DiCosimo at al., U.S. 2009/0005590).

As used herein, the term "*Bacillus subtilis* ATCC® 31954™" refers to a bacterial cell deposited to the American Type Culture Collection (ATCC) having international depository accession number ATCC® 31954™. An enzyme having significant perhydrolase activity from *B. subtilis* ATCC® 31954™ has been previously described (U.S. patent application Ser. No. 11/638,635) and is provided as SEQ ID NO: 2 (GENBANK®Accession No. BAA01729.1). The *B. subtilis* ATCC® 31954™ perhydrolase sequence (SEQ ID NO: 2) is used as a reference sequence to illustrate the conserved CE-7 signature motif that defines the conserved structure within the family of CE-7 carbohydrate esterases (U.S. 2008/0176783 and Vincent at al., supra). An amino acid sequence alignment using CLUSTALW with the reference sequence SEQ ID NO: 2 may be used to identify enzymes having the CE-7 signature motif. An example of CLUSTAL alignment of several family 7 carbohydrate esterases illustrating the conserved motifs is provided in FIGS. 1A and 1B. Minor variations (typically 6 amino acids or less) between the relative amino acid positions of the motifs are expected due to small insertions and deletions. As such, the amino acid residue numbering of the reference sequence is used when referring to and claiming an amino acid sequence comprising a CE-7 signature motif.

As used herein, the term "*Lactococcus lactis*" refers to a species of bacteria that has been used in the fermentation of dairy products and non-dairy niches such as the fermentation of plant material (Siezen at al., *Appl. Environ. Microbiol.* (2008) 74(2): 424-436). *Lactococcus lactis* subsp. *lactis* is the subspecies more often associated with fermented plant materials whereas the subspecies *Lactococcus lactis* subsp. *cremora* is more commonly associated with the fermentation of dairy products. In one embodiment, the perhydrolase catalyst comprises an enzyme having at least 95% amino acid sequence identity (or, in various embodiments, 96%, 97%, 98%, or 99% sequence identity) to SEQ ID NO: 4. In a preferred embodiment, the present enzyme catalyst comprises an acetyl xylan esterase from *Lactococcus lactis* subsp. *lactis* having perhydrolysis activity having amino acid sequence SEQ ID NO: 4 (GENBANK® Accession No. ABX75634.1).

As used herein, the term "*Mesorhizobium loti*" refers to a thermophilic bacterium comprising an acetyl xylan esterase having perhydrolysis activity and is provided as SEQ ID NO: 6 (GENBANK® Accession No. BAB53179.1).

As used herein, the term "*Geobacillus stearothermophilus*" refers to a thermophilic bacterium comprising an acetyl xylan esterase having perhydrolysis activity and is provided as SEQ ID NO: 8 (GENBANK® Accession No. AAF70202.1).

As used herein, the term "*Thermotoga neapolitana*" refers to a bacterium comprising an acetyl xylan esterase having perhydrolysis activity and is provided as SEQ ID NO: 39 (GENBANK® AAB70869; U.S. Patent Application Publication No. 2008-0176299; incorporated herein by reference).

As used herein, the term "*Thermotoga maritima* MSB8" refers to a thermophilic bacterium comprising an acetyl xylan esterase having perhydrolysis activity and is provided as SEQ ID NO: 40 (GENBANK® NP_227893.1; U.S. Patent Application Publication No. 2008-0176299).

As used herein, the terms "*Bacillus pumilus* PS213" and "*Bacillus pumilus*" refer to a bacterium comprising an acetyl xylan esterase having perhydrolysis activity and is provided as SEQ ID NO: 41 (GENBANK® AJ249957; U.S. Patent Application Publication No. 2008-0176299).

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |

-continued

| Amino Acid | Three-Letter Abbreviation | One-Letter Abbreviation |
|---|---|---|
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid (or as defined herein) | Xaa | X |

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D., T. *Molecular Cloning: A Laboratory Manual*, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (Sambrook and Russell, supra). For hybridizations with shorter nucleic acids, i.e., oligonucleotides, the position of mismatches becomes more important, and the length of the oligonucleotide determines its specificity (Sambrook and Russell, supra). In one aspect, the length for a hybridizable nucleic acid is at least about 10 nucleotides. Preferably, a minimum length for a hybridizable nucleic acid is at least about 15 nucleotides in length, more preferably at least about 20 nucleotides in length, even more preferably at least 30 nucleotides in length, even more preferably at least 300 nucleotides in length, and most preferably at least 800 nucleotides in length. Furthermore, the skilled artisan will recognize that the temperature and wash solution salt concentration may be adjusted as necessary according to factors such as length of the probe.

As used herein, the term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects*

(Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs. Sequence alignments and percent identity calculations may be performed using the Megalign program of the LASERGENE bioinformatics computing suite (DNASTAR Inc., Madison, Wis.), the AlignX program of Vector NTI v. 7.0 (Informax, Inc., Bethesda, Md.), or the EMBOSS Open Software Suite (EMBL-EBI; Rice et al., *Trends in Genetics* 16, (6) pp 276-277 (2000)). Multiple alignment of the sequences can be performed using the Clustal method (i.e. CLUSTALW; for example version 1.83) of alignment (Higgins and Sharp, *CABIOS*, 5:151-153 (1989); Higgins et al., *Nucleic Acids Res.* 22:4673-4680 (1994); and Chema et al., *Nucleic Acids Res* 31 (13):3497-500 (2003)), available from the European Molecular Biology Laboratory via the European Bioinformatics Institute) with the default parameters. Suitable parameters for CLUSTALW protein alignments include GAP Existence penalty=15, GAP extension=0.2, matrix=Gannet (e.g. Gonnet250), protein ENDGAP=−1, Protein GAPDIST=4, and KTUPLE=1. In one embodiment, a fast or slow alignment is used with the default settings where a slow alignment is preferred. Alternatively, the parameters using the CLUSTALW method (version 1.83) may be modified to also use KTUPLE=1, GAP PENALTY=10, GAP extension=1, matrix=BLOSUM (e.g. BLOSUM64), WINDOW=5, and TOP DIAGONALS SAVED=5.

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNASTAR (DNASTAR, Inc. 1228 S. Park St. Madison, Wis. 53715 USA), CLUSTALW (for example, version 1.83; Thompson et al., *Nucleic Acids Research*, 22(22):4673-4680 (1994), and the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y.), Vector NTI (Informax, Bethesda, Md.) and Sequencher v. 4.05. Within the context of this application it will be understood that where sequence analysis software is used for analysis, that the results of the analysis will be based on the "default values" of the program referenced, unless otherwise specified. As used herein "default values" will mean any set of values or parameters set by the software manufacturer that originally load with the software when first initialized.

As used herein, the term "biological contaminants" refers to one or more unwanted and/or pathogenic biological entities including, but not limited to, microorganisms, spores, viruses, prions, and mixtures thereof. The present enzyme can be used to produce an efficacious concentration of at least one percarboxylic acid useful to reduce and/or eliminate the presence of the viable biological contaminants. In a preferred embodiment, the biological contaminant is a viable pathogenic microorganism.

As used herein, the term "disinfect" refers to the process of destruction of or prevention of the growth of biological contaminants. As used herein, the term "disinfectant" refers to an agent that disinfects by destroying, neutralizing, or inhibiting the growth of biological contaminants. Typically, disinfectants are used to treat inanimate objects or surfaces. As used herein, the term "antiseptic" refers to a chemical agent that inhibits the growth of disease-carrying microorganisms. In one aspect of the embodiment, the biological contaminants are pathogenic microorganisms.

As used herein, the term "virucide" refers to an agent that inhibits or destroys viruses, and is synonymous with "viricide". An agent that exhibits the ability to inhibit or destroy viruses is described as having "virucidal" activity. Peroxycarboxylic acids can have virucidal activity. Typical alternative virucides known in the art which may be suitable for use with the present invention include, for example, alcohols, ethers, chloroform, formaldehyde, phenols, beta propiolactone, iodine, chlorine, mercury salts, hydroxylamine, ethylene oxide, ethylene glycol, quaternary ammonium compounds, enzymes, and detergents.

As used herein, the term "biocide" refers to a chemical agent, typically broad spectrum, which inactivates or destroys microorganisms. A chemical agent that exhibits the ability to inactivate or destroy microorganisms is described as having "biocidal" activity. Peroxycarboxylic acids can have biocidal activity. Typical alternative biocides known in the art, which may be suitable for use in the present invention include, for example, chlorine, chlorine dioxide, chloroisocyanurates, hypochlorites, ozone, acrolein, amines, chlorinated phenolics, copper salts, organo-sulphur compounds, and quaternary ammonium salts.

As used herein, the phrase "minimum biocidal concentration" refers to the minimum concentration of a biocidal agent that, for a specific contact time, will produce a desired lethal, irreversible reduction in the viable population of the targeted microorganisms. The effectiveness can be measured by the $\log_{10}$ reduction in viable microorganisms after treatment. In one aspect, the targeted reduction in viable microorganisms after treatment is at least a 3-log reduction, more preferably at least a 4-log reduction, and most preferably at least a 5-log reduction. In another aspect, the minimum biocidal concentration is at least a 6-log reduction in viable microbial cells.

As used herein, the terms "peroxygen source" and "source of peroxygen" refer to compounds capable of providing hydrogen peroxide at a concentration of about 1 mM or more when in an aqueous solution including, but not limited to, hydrogen peroxide, hydrogen peroxide adducts (e.g., urea-hydrogen peroxide adduct (carbamide peroxide)), perborates, and percarbonates. As described herein, the concentration of the hydrogen peroxide provided by the peroxygen compound in the aqueous reaction mixture is initially at least 1 mM or more upon combining the reaction components. In one embodiment, the hydrogen peroxide concentration in the aqueous reaction mixture is at least 10 mM. In another embodiment, the hydrogen peroxide concentration in the aqueous reaction mixture is at least 100 mM. In another embodiment, the hydrogen peroxide concentration in the aqueous reaction mixture is at least 200 mM. In another embodiment, the hydrogen peroxide concentration in the aqueous reaction mixture is 500 mM or more. In yet another embodiment, the hydrogen peroxide concentration in the aqueous reaction mixture is 1000 mM or more. The molar ratio of the hydrogen peroxide to enzyme substrate, e.g. triglyceride, ($H_2O_2$:substrate) in the aqueous reaction mixture may be from about 0.002 to 20, preferably about 0.1 to 10, and most preferably about 0.5 to 5.

As used herein, the term "benefit agent" refers to something that promotes or enhances a useful advantage or favorable effect. In one embodiment, a process is provided whereby a benefit agent, such as a composition comprising a peroxycarboxylic acid, is applied to a textile to achieve a desired benefit, such as disinfecting, bleaching, destaining, deodorizing, and any combination thereof.

As used herein, the terms "not a substantial increase", "not a significant increase", and "is not exceeded" are used when referring to the increase in the concentration of peroxycarboxylic acid in the reaction mixture relative to a peroxycarboxylic acid concentration measured at a specified time point, wherein the time point refers to the amount of time after the reaction components are combined whereby a peroxycarboxylic acid is produced. The present process produces a substantially stable concentration of peroxycarboxylic acid at a specific time point. As used herein, "substantially stable concentration" will refer to the concentration of peroxycarboxylic acid in the reaction mixture that does not increase by more than a 100% (i.e. 2× or less) over a defined time interval. In one embodiment, the concentration of peroxycarboxylic acid produced 1 minute after combining the reaction components is the reference concentration upon which changes in concentration after 1 minute are compared. The changes in concentration may be reported as a percent (%) change in concentration relative to the reference time concentration. In another embodiment, the reference concentration of peroxycarboxylic acid is the concentration measured 5 minutes after combining the reaction components. In one embodiment, an increase in peroxycarboxylic acid concentration that is not substantial will be defined as an increase of 100% or less (i.e., 2×), preferably no more than 50%, and most preferably no more than 20% higher than the reference concentration measured at a specified time point.

In one embodiment, the concentration of peroxycarboxylic acid produced one minute after combining the reaction components is not exceeded by (i.e., is not increased by) more than 100%, preferably not more than 50%, and more preferably not more than 20% at a reaction time equal to or greater than 30 minutes, preferably 5 minutes, after combining the reaction components.

In another embodiment, the concentration of peroxycarboxylic acid produced 5 minutes after combining the reaction components is not exceeded by (i.e., is not increased by) more than 100%, preferably not more than 50%, and more preferably not more than 20% at a reaction time equal to or greater than 30 minutes after combining the reaction components.

As used herein, the terms "signature motif", "CE-7 signature motif", and "diagnostic motif" refer to conserved structures shared among a family of enzymes having a defined activity. The signature motif can be used to define and/or identify the family of structurally related enzymes having similar enzymatic activity for a defined family of substrates. The signature motif can be a single contiguous amino acid sequence or a collection of discontiguous, conserved motifs that together form the signature motif. Typically, each conserved motif is represented by a conserved amino acid sequence. Means to identify enzymes having the CE-7 signature motif are described herein.

Carbohydrate Esterase Family 7 Enzymes Having Perhydrolysis Activity and the CE-7 Signature Motif Enzymes belonging to the family of CE-7 carbohydrate esterases share a collection of discontiguous motifs that together form the CE-7 signature motif (defined by Vincent et al., supra). The signature motif for CE-7 esterases comprises 3 conserved motifs (residue position numbering relative to reference sequence SEQ ID NO: 2):

a) Arg118-Gly119-Gln120;

b) Gly179-Xaa180-Ser181-Gln182-Gly183; and c) His298-Glu299.

Typically, the Xaa at amino acid residue position 180 is glycine, alanine, proline, tryptophan, or threonine. Two of the three amino acid residues belonging to the catalytic triad are in bold. In one embodiment, the Xaa at amino acid residue position 180 is selected from the group consisting of glycine, alanine, proline, tryptophan, and threonine.

Amino acid residues belonging to the catalytic triad are in bold. An aspartic acid residue at position 269 (Asp269) is the third member of the catalytic triad (Ser181-Asp269-His298; all residue positions relative to the amino acid numbering of SEQ ID NO: 2).

Members of the CE-7 carbohydrate esterase family have been shown to have perhydrolysis activity suitable for producing peroxycarboxylic acids from carboxylic acid esters in the presence of a suitable source of peroxygen, such as hydrogen peroxide (DiCosimo et al., U.S. Ser. No. 12/143,375). The present perhydrolase is a member of the CE-7 carbohydrate esterase family. A CLUSTALW alignment of the present perhydrolase illustrates that it belongs to the CE-7 carbohydrate esterase family (FIGS. 1A and 1B; Table 2).

A number of well-known global alignment algorithms may be used to align two or more amino acid sequences representing enzymes having perhydrolase activity to determine if the enzyme is comprised of the CE-7 signature motif. The aligned sequence(s) are compared to the present reference sequence (SEQ ID NO: 2) to determine the existence of the signature motif. In one embodiment, a CLUSTAL alignment (e.g., CLUSTALW) using a reference amino acid sequence (as used herein the perhydrolase sequence (SEQ ID NO: 2) from the *Bacillus subtilis* ATCC® 31954™) is used to identify perhydrolases belonging to the CE-7 esterase family. The relative numbering of the conserved amino acid residues is based on the residue numbering of the reference amino acid sequence to account for small insertions or deletions (for example, 6 amino acids or less) within the aligned sequence.

Examples of other suitable algorithms that may be used to identify sequences comprising the CE-7 signature motif (when compared to the reference sequence) include, but are not limited to, Needleman and Wunsch (*J. Mol. Biol.* 48, 443-453 (1970); a global alignment tool) and Smith-Waterman (*J. Mol. Biol.* 147:195-197 (1981); a local alignment tool). In one embodiment, a Smith-Waterman alignment is implemented using default parameters. An example of suitable default parameters include the use of a BLOSUM62 scoring matrix with GAP open penalty=10 and a GAP extension penalty=0.5.

U.S. Patent Application Publication No. 2008/0176783 provides a comparison of overall percent identity among several CE-7 enzymes having perhydrolase activity, illustrating the very low percent identity often observed between members having the conserved CE-7 signature motif. A BLASTP comparison among the CE-7 carbohydrate esterase family members is provided in Table 1. Even though the CEJ enzymes provided in Table 1 may have relatively low overall percent identity over their entire length, all of the members share the conserved CE-7 signature motifs as shown in Table 2.

TABLE 1

Percent Identity Between[b] Several CE-7 Enzymes Having Perhydrolase Activity and the Closest Match from GENBANK® nr Database

| | L. lactis | M. loti | G. stearo-thermophilus | B. subtilis ATCC 31954™ | Closest Match in Amino Acid Identity (BLASTP[a] of GENBANK® nr database) |
|---|---|---|---|---|---|
| Lactococcus. lactis (SEQ ID NO: 4) | 100 | 27 | 49 | 31 | 57% identity to an acetyl xylan esterase from Carnobacterium sp. AT7 GENBANK® Accession No. ZP_02184505 Direct Submission by Bartlett et al. |
| Mesorhizobium loti (SEQ ID NO: 6) | 27 | 100 | 32 | 34 | 55% identity to an acetyl xylan esterase from Streptomyces avermitilis MA-4680. GENBANK® Accession No. NP_822477 Ikeda et al., Nat. Biotechnol. 21 (5), 526-531 (2003) |
| Geobacillus stearothermophilus (SEQ ID NO: 8) | 49 | 32 | 100 | 35 | 54% identity to a xylan esterase from Thermoanaerobacterium sp. 'JW/SL YS485' GENBANK® Accession No. AAB68821 Lorenz, W. W. and Wiegel, J., J. Bacteriol. 179 (17), 5436-5441 (1997) |
| B. subtilis ATCC 31954™ (SEQ ID NO: 2) | 31 | 34 | 35 | 100 | 98% identity to a cephalosporin C deacetylase from Bacillus subtilis subsp. subtilis str. 168 GENBANK® Accession No. NP_388200 Kunst et al., Nature 390 (6657), 249-256 (1997) |
| T. Neapolitana (SEQ ID NO: 39) | 30 | 51 | 34 | 42 | 91% identify to an acetyl xylan esterase from Thermotoga sp. RQ2 GENBANK® Accession No. YP_001738905 |
| T. Maritima (SEQ ID NO: 40) | 29 | 52 | 35 | 41 | 97% identify to an acetyl xylan esterase from Thermotoga sp. RQ2 GENBANK® Accession No. YP_001738905 |
| B. pumilus (SEQ ID NO: 41) | 32 | 33 | 36 | 76 | 91% identify to an acetyl xylan esterase from B. pumilus ATCC® 7061 GENBANK® Accession No. ZP_03054555 |

[a] = BLASTP 2.2.21. Altschul et al., Nucleic Acids Res. 25: 3389-3402; Altschul et al. FEBS J. 272: 5101-5109.
[b] = blast2seq algorithm using BLOSUM62, gap open = 11, gap extension = 1, x_drop = 0, expect = 10, and wordsize = 3. Tatiana A. Tatusova, Thomas L. Madden (1999), FEMS Microbiol Lett. 174: 247-250

All of the CE-7 carbohydrate esterases having perhydrolase activity in Table 1 have the CE-7 signature motifs as illustrated in FIGS. 1A and 1B (underlined) and Table 2.

TABLE 2

Conserved motifs found within several CE-7 carbohydrate esterase enzymes having perhydrolysis activity.

| Perhydrolase Sequence | RGQ motif[a] (Residue #s) | GXSQG motif[a] (Residue #s) | Aspartic Acid Residue Used in Catalytic Triad | HE motif[a] (Residue #s) |
|---|---|---|---|---|
| SEQ ID NO: 2 | 118-120 | 179-183 | 269 | 298-299 |
| SEQ ID NO: 4 | 114-116 | 177-181 | 269 | 298-299 |
| SEQ ID NO: 6 | 118-120 | 184-188 | 272 | 301-302 |
| SEQ ID NO: 8 | 116-118 | 180-184 | 273 | 302-303 |
| SEQ ID NO: 39 | 118-120 | 186-190 | 274 | 303-304 |
| SEQ ID NO: 40 | 118-120 | 186-190 | 274 | 303-304 |
| SEQ ID NO: 41 | 118-120 | 179-183 | 269 | 298-299 |

[a] = Conserved motifs defined by Vincent et al., supra, used to define the signature motif. The "X" is GXSQG motif is typically Gly, Ala, or Asp.

The present examples illustrate the characteristic properties of the Lactococcus lactis perhydrolase (SEQ ID NO: 4) when compared to perhydrolases from Mesorhizobium loti perhydrolase (SEQ ID NO: 6), Geobacillus stearothermophilus perhydrolase (SEQ ID NO: 8), Bacillus subtilis (SEQ ID NO: 2), Thermotoga neapolitana (SEQ ID NO: 39), Thermotoga maritima (SEQ ID NO: 40), and Bacillus pumilus (SEQ ID NO: 41). More specifically, the L. lactis perhydrolase is characterized by the ability to rapidly generate a target peroxycarboxylic acid concentration that does not substantially increase 5 minutes, preferably one minute, after combining the reaction components. As illustrated in the examples, the rapid enzyme inactivation characteristic of the Lactococcus lactis perhydrolase is independent of a substantial drop in pH, wherein the pH of the reaction mixture remains in the range of 6.0 to about 9.0, preferably between 6.5 and 8.5, over the course of the enzyme catalyzed reaction. The desired concentration can be controlled by adjusting the amounts of the selected reaction components, so long as the enzyme catalyst comprises an enzyme having perhydrolysis activity with at least 95% amino acid identity to SEQ ID NO: 4. In one embodiment, the enzyme catalyst comprises an enzyme having perhydrolysis activity with the amino acid sequence SEQ ID NO: 4. In another embodiment, the reaction components are combined under conditions wherein the desired concentration is achieved within 5 minutes (as measured from the time the reaction components are combined whereby enzymatic perhydrolysis is initiated), preferably within 1 minute of combining the reaction components, wherein the peroxycarboxylic acid concentration does not substantially increase after the desired concentration is achieved.

CE-7 Enzymes Substantially Similar to the Lactococcus lactis Perhydrolase

One of skill in the art will recognize that the scope of the present invention includes CE-7 enzymes having perhydrolysis activity that are substantially similar to the Lactococcus lactis perhydrolase as provided by SEQ ID NO: 4. As used herein, "substantially similar" may refer to an enzyme having an amino acid sequence that is at least 95%, 96%, 97%, 98%, 99% or 100% identical to SEQ ID NO: 4 and comprises a CE-7 signature motif, wherein the resulting enzyme retains the characteristic functional properties of the perhydrolytic enzyme (i.e., high perhydrolytic activity followed by a loss in perhydrolytic activity that occurs independent of substantial drop in pH). In one embodiment, the present enzyme further comprises a CE-7 signature motif.

In one embodiment, the term "substantially similar" may be used to refer to nucleic acid molecules encoding amino acid sequences of CE-7 perhydrolases having at least 95%, 96%, 97%, 98%, 99% or 100% amino acid identify to SEQ ID NO: 4 and comprises a CE-7 signature motif. For example, it is well known in the art that alterations in a gene which result in the production of a chemically equivalent amino acid at a given site, but do not affect the functional properties of the encoded protein are common. For the purposes of the present invention substitutions are defined as exchanges within one of the following five groups:
1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, and Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

Each of the proposed modifications is well within the routine skill in the art, as is determination of retention of the characteristic biological activity of the encoded products. In one embodiment, substantially similar nucleic acid sequences are defined by their ability to hybridize, under highly stringent conditions (0.1×SSC, 0.1% SDS, 65° C. and washed with 2×SSC, 0.1% SDS followed by 0.1×SSC, 0.1% SDS, 65° C.) with the complementary sequence of SEQ ID NO: 3.

In one aspect, suitable the nucleic acid molecule encode a polypeptide having perhydrolysis activity, wherein said polypeptide has an amino acid sequence that is at least 95% identical to SEQ ID NO: 4 and has a CE-7 signature motif. Suitable nucleic acid molecules of the present invention encode a polypeptide having about 300 to about 340 amino acids, preferably about 310 to about 330 amino acids, and most preferably about 312 amino acids in length.

As used herein, a "substantial drop in pH" or "substantial change in pH" refers to a drop in pH of more than about 1 over the course of the enzyme catalyzed reaction. It is understood that the pH of the reaction mixture over the course of the reaction will not drop below about 6.0 and will preferably be maintained between about 6.0 to about 9.0, more preferably about 6.5 to about 8.5, even more preferably about 7.0 to about 8.5, and most preferably about 7.0 to about 8.0.

As used herein, "over the course of the reaction" refers to the time period measured from initially combining reaction components to form the reaction mixture (to initiate enzymatic perhydrolysis using the present catalyst) until a point in time wherein the enzyme catalyst no longer exhibits perhydrolytic activity. The loss in perhydrolytic activity may be determined or inferred by a peroxycarboxylic acid concentration in the reaction mixture that no longer significantly increases once the desired target concentration (or concentration range) is achieved.

Suitable Reaction Conditions for the Enzyme-Catalyzed Preparation of Peroxycarboxylic Acids from Carboxylic Acid Esters and Hydrogen Peroxide A process is provided to produce an aqueous mixture comprising at least one peroxycarboxylic acid by reacting carboxylic acid esters and an inorganic peroxide (such as hydrogen peroxide, sodium perborate or sodium percarbonate) in the presence of an enzyme catalyst having perhydrolysis activity, wherein the enzyme catalyst comprises an enzyme having a CE-7 signature motif and at least 95% amino acid identity to SEQ ID NO: 4 and retains the characteristic properties of the *L. lactis* perhydrolase, namely perhydrolase activity capable of rapidly producing peroxycarboxylic acid in the reaction mixture within five minutes, preferably within one minute, that does not substantially increase over at least the next 30 minutes (or other time point defined by the preferred embodiments).

In one embodiment, suitable substrates include esters provided by the following formula:

[X]$_m$R$_5$ wherein X=an ester group of the formula R$_6$C(O)O
R$_6$=C1 to C7 linear, branched or cyclic hydrocarbyl moiety, optionally substituted with hydroxyl groups or C1 to C4 alkoxy groups, wherein R$_6$ optionally comprises one or more ether linkages for R$_6$=C2 to C7;
R$_5$=a C1 to C6 linear, branched, or cyclic hydrocarbyl moiety optionally substituted with hydroxyl groups; wherein each carbon atom in R$_5$ individually comprises no more than one hydroxyl group or no more than one ester group; wherein R$_5$ optionally comprises one or more ether linkages;
m=1 to the number of carbon atoms in R$_5$; and
wherein said esters have solubility in water of at least 5 ppm at 25° C.

In another embodiment, suitable substrates include glycerides of the formula:

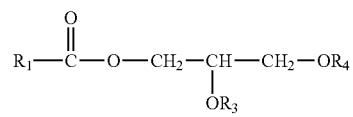

wherein R$_1$=C1 to C7 straight chain or branched chain alkyl optionally substituted with a hydroxyl or a C1 to C4 alkoxy group and R$_3$ and R$_4$ are individually H or R$_1$C(O).

In another embodiment, R$_6$ is C1 to C7 linear hydrocarbyl moiety, optionally substituted with hydroxyl groups or C1 to C4 alkoxy groups, optionally comprising one or more ether linkages. In a further preferred embodiment, R$_6$ is C2 to C7 linear hydrocarbyl moiety, optionally substituted with hydroxyl groups, and/or optionally comprising one or more ether linkages.

Suitable substrates also include acetylated saccharides selected from the group consisting of acetylated mono-, di-, and polysaccharides. In another embodiment, the acetylated saccharides are selected from the group consisting of acetylated xylan, fragments of acetylated xylan, acetylated xylose (such as xylose tetraacetate), acetylated glucose (such as glucose pentaacetate), β-D-ribofuranose-1,2,3,5-tetraacetate, tri-O-acetyl-D-galactal, tri-O-acetyl-D-glucal, and acetylated cellulose. In a preferred embodiment, the acetylated saccharide is selected from the group consisting of β-D-ribofuranose-1,2,3,5-tetraacetate, tri-O-acetyl-D-galactal, tri-O-acetyl-D-glucal, and acetylated cellulose.

In another embodiment, suitable substrates are selected from the group consisting of: monoacetin; diacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-glucal; monoesters or diesters of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,6-pentanediol, 1,2-hexanediol, 2,5-hexanediol, 1,6-hexanediol; and mixtures thereof. In a further embodiment, the suitable substrate comprises propylene glycol diacetate (PGDA), ethylene glycol diacetate (EDGA), or a mixture thereof.

In another embodiment, the carboxylic acid ester is selected from the group consisting of monoacetin, diacetin, triacetin, and combinations thereof. In another embodiment, the substrate is a C1 to C6 polyol comprising one or more ester groups. In a preferred embodiment, one or more of the hydroxyl groups on the C1 to C6 polyol are substituted with one or more acetoxy groups (such as 1,3-propanediol diacetate, 1,4-butanediol diacetate, etc.).

In another embodiment, suitable substrates are selected from the group consisting of ethyl acetate, methyl lactate, ethyl lactate, methyl glycolate, ethyl glycolate, methyl methoxyacetate, ethyl methoxyacetate, methyl 3-hydroxybutyrate, ethyl 3-hydroxybutyrate, triethyl 2-acetyl citrate, glucose pentaacetate, gluconolactone, glycerides (mono-, di-, and triglycerides) such as monoacetin, diacetin, triacetin, monopropionin, dipropionin (glyceryl dipropionate), tripropionin (1,2,3-tripropionylglycerol), monobutyrin, dibutyrin (glyceryl dibutyrate), tributyrin (1,2,3-tributyrylglycerol), acetylated saccharides, and mixtures thereof.

In a further embodiment, suitable substrates are selected from the group consisting of monoacetin, diacetin, triacetin, monopropionin, dipropionin, tripropionin, monobutyrin, dibutyrin, tributyrin, ethyl acetate, and ethyl lactate. In yet another aspect, the substrate is selected from the group consisting of diacetin, triacetin, ethyl acetate, and ethyl lactate.

The carboxylic acid ester is present in the reaction mixture at a concentration sufficient to produce the desired concentration of peroxycarboxylic acid upon enzyme-catalyzed perhydrolysis. The carboxylic acid ester need not be completely soluble in the reaction mixture, but has sufficient solubility to permit conversion of the ester by the perhydrolase catalyst to the corresponding peroxycarboxylic acid. The carboxylic acid ester is present in the reaction mixture at a concentration of 0.0005 wt % to 40 wt % of the reaction mixture, preferably at a concentration of 0.1 wt % to 20 wt % of the reaction mixture, and more preferably at a concentration of 0.5 wt % to 10 wt % of the reaction mixture. The wt % of carboxylic acid ester may optionally be greater than the solubility limit of the carboxylic acid ester, such that the concentration of the carboxylic acid ester is at least 0.0005 wt % in the reaction mixture that is comprised of water, enzyme catalyst, and source of peroxide, where the remainder of the carboxylic acid ester remains as a second separate phase of a two-phase aqueous/organic reaction mixture. Not all of the added carboxylic acid ester must immediately dissolve in the aqueous reaction mixture, and after an initial mixing of all reaction components, additional continuous or discontinuous mixing is optional.

The peroxycarboxylic acids produced by the present reaction components may vary depending upon the selected substrates, so long as the present enzyme catalyst is used. In one embodiment, the peroxycarboxylic acid produced is peracetic acid, perpropionic acid, perbutyric acid, perlactic acid, perglycolic acid, permethoxyacetic acid, per-β-hydroxybutyric acid, or mixtures thereof.

The peroxygen source may include, but is not limited to, hydrogen peroxide, hydrogen peroxide adducts (e.g., urea-hydrogen peroxide adduct (carbamide peroxide)), perborate salts and percarbonate salts. The concentration of peroxygen compound in the reaction mixture may range from 0.0033 wt % to about 50 wt %, preferably from 0.033 wt % to about 40 wt %, more preferably from 0.33 wt % to about 30 wt %.

Many perhydrolase catalysts (whole cells, permeabilized whole cells, and partially purified whole cell extracts) have been reported to have catalase activity (EC 1.11.1.6). Catalases catalyze the conversion of hydrogen peroxide into oxygen and water. In one aspect, the enzyme catalyst having perhydrolase activity lacks catalase activity. In another aspect, a catalase inhibitor is added to the reaction mixture. Examples of catalase inhibitors include, but are not limited to, sodium azide and hydroxylamine sulfate. One of skill in the art can adjust the concentration of catalase inhibitor as needed. The concentration of the catalase inhibitor typically ranges from 0.1 mM to about 1 M; preferably about 1 mM to about 50 mM; more preferably from about 1 mM to about 20 mM. In one aspect, sodium azide concentration typically ranges from about 20 mM to about 60 mM while hydroxylamine sulfate is concentration is typically about 0.5 mM to about 30 mM, preferably about 10 mM.

The catalase activity in a host cell can be down-regulated or eliminated by disrupting expression of the gene(s) responsible for the catalase activity using well known techniques including, but not limited to, transposon mutagenesis, RNA antisense expression, targeted mutagenesis, and random mutagenesis. In a preferred embodiment, the gene(s) encoding the endogenous catalase activity are down-regulated or disrupted (i.e. knocked-out). As used herein, a "disrupted" gene is one where the activity and/or function of the protein encoded by the modified gene is no longer present. Means to disrupt a gene are well-known in the art and may include, but are not limited to, insertions, deletions, or mutations to the gene so long as the activity and/or function of the corresponding protein is no longer present. In a further preferred embodiment, the production host is an *E. coli* production host comprising a disrupted catalase gene selected from the group consisting of katG and katE (see U.S. Patent Application Publication No. 2008/0176783 to DiCosimo at al., hereby incorporated by reference). In another embodiment, the production host is an *E. coli* strain comprising a down-regulation and/or disruption in both katG and a katE catalase genes. An *E. coli* strain comprising a double-knockout of katG and katE has been prepared and is described herein as *E. coli* strain KLP18 (Example 3).

The concentration of the catalyst in the aqueous reaction mixture depends on the specific catalytic activity of the catalyst, and is chosen to obtain the desired rate of reaction. The weight of catalyst in perhydrolysis reactions typically ranges from 0.0005 mg to 10 mg per mL of total reaction volume, preferably from 0.010 mg to 2.0 mg per mL. The catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. The use of immobilized catalysts permits the recovery and reuse of the catalyst in subsequent reactions. The enzyme catalyst may be in the form of whole microbial cells, permeabilized microbial cells, microbial cell extracts, partially-purified or purified enzymes, and mixtures thereof.

In one aspect, the concentration of peroxycarboxylic acid generated by the combination of chemical perhydrolysis and enzymatic perhydrolysis of the carboxylic acid ester is sufficient to provide an effective concentration of peroxycarboxylic acid for bleaching or disinfection at a desired pH. In another aspect, the present methods provide combinations of enzymes and enzyme substrates to produce the desired effective concentration of peroxycarboxylic acid, where, in the absence of added enzyme, there is a significantly lower concentration of peroxycarboxylic acid produced. Although there may be some chemical perhydrolysis of the enzyme substrate by direct chemical reaction of inorganic peroxide with the enzyme substrate, there may not be a sufficient concentration of peroxycarboxylic acid generated to provide an effective concentration of peroxycarboxylic acid in the desired applications, and a significant increase in total peroxycarboxylic acid concentration is achieved by the addition of an appropriate perhydrolase catalyst to the reaction mixture.

The concentration of peroxycarboxylic acid generated (e.g. peracetic acid) by the enzymatic perhydrolysis is at least about 2 ppm, preferably at least 20 ppm, preferably at least 100 ppm, more preferably at least about 200 ppm peroxycarboxylic acid, more preferably at least 300 ppm, more preferably at least 500 ppm, more preferably at least 700 ppm, more preferably at least about 1000 ppm peroxycarboxylic acid, most preferably at least 2000 ppm peroxycarboxylic acid within 5 minutes more preferably within 1 minute of initiating the enzymatic perhydrolysis reaction.

The product mixture comprising the peroxycarboxylic acid may be optionally diluted with a diluent comprising water, or a solution predominantly comprised of water, to produce a mixture with the desired lower target concentration of peroxycarboxylic acid. In one aspect, the reaction time required to produce the desired concentration (or concentration range) of peroxycarboxylic acid is about 5 minutes or less, more preferably about 1 minute or less.

In other aspects, the surface or inanimate object contaminated with a concentration of a biological contaminant(s) is contacted with the peroxycarboxylic acid formed in accordance with the processes described herein within about 1 minute to about 168 hours of combining said reaction components, or within about 1 minute to about 48 hours, or within about 1 minute to 2 hours of combining said reaction components, or any such time interval therein.

In another aspect, the peroxycarboxylic acid formed in accordance with the processes describe herein is used in a laundry care application wherein the peroxycarboxylic acid is contacted with a textile to provide a benefit, such as disinfecting, bleaching, destaining, deodorizing or a combination thereof. The peroxycarboxylic acid may be used in a variety of laundry care products including, but not limited to, textile pre-wash treatments, laundry detergents, stain removers, bleaching compositions, deodorizing compositions, and rinsing agents. In one embodiment, the present process to produce a peroxycarboxylic acid for a target surface is conducted in situ.

The temperature of the reaction is chosen to control both the reaction rate and the stability of the enzyme catalyst activity. The temperature of the reaction may range from just above the freezing point of the reaction mixture (approximately 0° C.) to about 75° C., with a preferred range of reaction temperature of from about 5° C. to about 55° C.

The pH of the reaction mixture while enzymatically producing peroxycarboxylic acid is maintained at a pH ranging from about 6.0 to about 9.0, preferably about 6.5 to about 8.5, and yet even more preferably about 6.5 to about 7.5. In one embodiment, the pH of the reaction mixture ranges from about 6.5 to about 8.5 for at least 30 minutes after combining the reaction components. The pH of the reaction mixture may be controlled by the addition or incorporation of a suitable buffer, including, but not limited to, phosphate, pyrophosphate, bicarbonate, acetate, or citrate. In one embodiment, the buffer is selected from a phosphate buffer and a bicarbonate buffer. The concentration of buffer, when employed, is typically from 0.1 mM to 1.0 M, preferably from 1 mM to 300 mM, most preferably from 10 mM to 100 mM.

In another aspect, the enzymatic perhydrolysis reaction mixture may contain an organic solvent that acts as a dispersant to enhance the rate of dissolution of the carboxylic acid ester in the reaction mixture. Such solvents include, but are not limited to, propylene glycol methyl ether, acetone, cyclohexanone, diethylene glycol butyl ether, tripropylene glycol methyl ether, diethylene glycol methyl ether, propylene glycol butyl ether, dipropylene glycol methyl ether, cyclohexanol, benzyl alcohol, isopropanol, ethanol, propylene glycol, and mixtures thereof.

In another aspect, the enzymatic perhydrolysis product may contain additional components that provide desirable functionality. These additional components include, but are not limited to, buffers, detergent builders, thickening agents, emulsifiers, surfactants, wetting agents, corrosion inhibitors (e.g., benzotriazole), enzyme stabilizers, and peroxide stabilizers (e.g., metal ion chelating agents). Many of the additional components are well known in the detergent industry (see for example U.S. Pat. No. 5,932,532; hereby incorporated by reference). Examples of emulsifiers include, but are not limited to, polyvinyl alcohol or polyvinylpyrrolidone. Examples of thickening agents include, but are not limited to, LAPONITE® RD, corn starch, PVP, CARBOWAX®, CARBOPOL®, CABOSIL®, polysorbate 20, PVA, and lecithin. Examples of buffering systems include, but are not limited to, sodium phosphate monobasic/sodium phosphate dibasic; sulfamic acid/triethanolamine; citric acid/triethanolamine; tartaric acid/triethanolamine; succinic acid/triethanolamine; and acetic acid/triethanolamine. Examples of surfactants include, but are not limited to, a) non-ionic surfactants such as block copolymers of ethylene oxide or propylene oxide, ethoxylated or propoxylated linear and branched primary and secondary alcohols, and aliphatic phosphine oxides b) cationic surfactants such as quaternary ammonium compounds, particularly quaternary ammonium compounds having a C8-C20 alkyl group bound to a nitrogen atom additionally bound to three C1-C2 alkyl groups, c) anionic surfactants such as alkane carboxylic acids (e.g., C8-C20 fatty acids), alkyl phosphonates, alkane sulfonates (e.g., sodium dodecylsulphate "SDS") or linear or branched alkyl benzene sulfonates, alkene sulfonates and d) amphoteric and zwitterionic surfactants such as aminocarboxylic acids, aminodicarboxylic acids, alkylbetaines, and mixtures thereof. Additional components may include fragrances, dyes, stabilizers of hydrogen peroxide (e.g., metal chelators such as 1-hydroxyethylidene-1,1-diphosphonic acid (DEQUEST® 2010, Solutia Inc., St. Louis, Mo. and ethylenediaminetetraacetic acid (EDTA)), TURPINAL® SL, DEQUEST® 0520, DEQUEST® 0531, stabilizers of enzyme activity (e.g., polyethyleneglycol (PEG)), and detergent builders.

In another aspect, the enzymatic perhydrolysis product may be pre-mixed to generate the desired concentration of peroxycarboxylic acid prior to contacting the surface or inanimate object to be disinfected and/or bleached.

In another aspect, the enzymatic perhydrolysis product is not pre-mixed to generate the desired concentration of peroxycarboxylic acid prior to contacting the surface or inanimate object to be disinfected, but instead, the components of the reaction mixture that generate the desired concentration of percarboxylic acid are contacted with the surface or inanimate object to be disinfected, generating the desired concentration of peroxycarboxylic acid. In some embodiments, the components of the reaction mixture combine or mix at the locus. In some embodiments, the reaction components are delivered or applied to the locus and subsequently mix or combine to generate the desired concentration of peroxycarboxylic acid.

Production of Peroxycarboxylic Acids Using a Perhydrolase Catalyst

The peroxycarboxylic acids, once produced, are quite reactive and may decrease in concentration over extended periods of time, depending on variables that include, but are not limited to, temperature and pH. As such, it may be desirable to keep the various reaction components separated, especially for liquid formulations. In one aspect, the hydrogen peroxide source is separate from either the substrate or the perhydrolase catalyst, preferably from both. This can be accomplished using a variety of techniques including, but not limited to, the use of multicompartment chambered dispensers (U.S. Pat. No. 4,585,150) and at the time of use physically combining the perhydrolase catalyst with an inorganic peroxide and the present substrates to initiate the aqueous enzymatic perhydrolysis reaction. The perhydrolase catalyst may optionally be immobilized within the body of reaction chamber or separated (e.g., filtered, etc.) from the reaction product comprising the peroxycarboxylic acid prior to contacting the surface and/or object targeted for treatment. The perhydrolase catalyst may be in a liquid matrix or in a solid form (e.g., powdered, tablet) or embedded within a solid matrix that is subsequently mixed with the substrates to initiate the enzymatic perhydrolysis reaction. In a further aspect, the perhydrolase catalyst may be contained within a dissolvable or porous pouch that may be added to the aqueous substrate matrix to initiate enzymatic perhydrolysis. In an additional further aspect, a powder comprising the enzyme catalyst is suspended in the substrate (e.g., triacetin), and at time of use is mixed with a source of peroxygen in water.

Method for Determining the Concentration of Peroxycarboxylic Acid and Hydrogen Peroxide.

A variety of analytical methods can be used in the present method to analyze the reactants and products including, but not limited to, titration, high performance liquid chromatography (H PLC), gas chromatography (GC), mass spectroscopy (MS), capillary electrophoresis (CE), the analytical procedure described by U. Karst et al., (*Anal. Chem.*, 69(17): 3623-3627 (1997)), and the 2,2'-azino-bis(3-ethylbenzothazoline)-6-sulfonate (ABTS) assay (S. Minning, et al., *Analytica Chimica Acta* 378:293-298 (1999) and WO 2004/058961 A1) as described in U.S. Patent Application Publication No. 2008/0176783.

Determination of Minimum Biocidal Concentration of Peroxycarboxylic Acids

The method described by J. Gabrielson, et al. (*J. Microbiol. Methods* 50: 63-73 (2002)) can be employed for determination of the Minimum Biocidal Concentration (MBC) of peroxycarboxylic acids, or of hydrogen peroxide and enzyme substrates. The assay method is based on XTT reduction inhibition, where XTT ((2,3-bis[2-methoxy-4-nitro-5-sulfophenyl]-5-[(phenylamino)carbonyl]-2H-tetrazolium, inner salt, monosodium salt) is a redox dye that indicates microbial respiratory activity by a change in optical density (OD) measured at 490 nm or 450 nm. However, there are a variety of other methods available for testing the activity of disinfectants and antiseptics including, but not limited to, viable plate counts, direct microscopic counts, dry weight, turbidity measurements, absorbance, and bioluminescence (see, for example Brock, Semour S., *Disinfection, Sterilization, and Preservation*, 5th edition, Lippincott Williams & Wilkins, Philadelphia, Pa., USA; 2001).

Uses of Enzymatically Prepared Peroxycarboxylic Acid Compositions

The enzyme catalyst-generated peroxycarboxylic acid produced according to the present method can be used in a variety of hard surface/inanimate object applications for reduction of concentrations of biological contaminants, such as decontamination of medical instruments (e.g., endoscopes), textiles (e.g., garments, carpets), food preparation surfaces, food storage and food-packaging equipment, materials used for the packaging of food products, chicken hatcheries and grow-out facilities, animal enclosures, and spent process waters that have microbial and/or virucidal activity. The enzyme-generated peroxycarboxylic acids may be used in formulations designed to inactivate prions (e.g. certain proteases) to additionally provide biocidal activity. In a preferred aspect, the present peroxycarboxylic acid compositions are particularly useful as a disinfecting agent for non-autoclavable medical instruments and food packaging equipment. As the peroxycarboxylic acid-containing formulation may be prepared using GRAS or food-grade components (enzyme, enzyme substrate, hydrogen peroxide, and buffer), the enzyme-generated peroxycarboxylic acid may also be used for decontamination of animal carcasses, meat, fruits and vegetables, or for decontamination of prepared foods. The enzyme-generated peroxycarboxylic acid may be incorporated into a product whose final form is a powder, liquid, gel, film, solid or aerosol. The enzyme-generated peroxycarboxylic acid may be diluted to a concentration that still provides an efficacious decontamination.

The compositions comprising an efficacious concentration of peroxycarboxylic acid can be used to disinfect surfaces and/or objects contaminated (or suspected of being contaminated) with biological contaminants by contacting the surface or object with the products produced by the present processes. As used herein, "contacting" refers to placing a disinfecting composition comprising an effective concentration of peroxycarboxylic acid in contact with the surface or inanimate object suspected of contamination with a biological contaminant for a period of time sufficient to clean and disinfect. Contacting includes spraying, treating, immersing, flushing, pouring on or in, mixing, combining, painting, coating, applying, affixing to and otherwise communicating a peroxycarboxylic acid solution or composition comprising an efficacious concentration of peroxycarboxylic acid, or a solution or composition that forms an efficacious concentration of peroxycarboxylic acid, with the surface or inanimate object suspected of being contaminated with a concentration of a biological contaminant. The disinfectant compositions may be combined with a cleaning composition to provide both cleaning and disinfection. Alternatively, a cleaning agent (e.g., a surfactant or detergent) may be incorporated into the formulation to provide both cleaning and disinfection in a single composition.

The compositions comprising an efficacious concentration of peroxycarboxylic acid can also contain at least one additional antimicrobial agent, combinations of prion-degrading proteases, a virucide, a sporicide, or a biocide. Combinations of these agents with the peroxycarboxylic acid produced by the claimed processes can provide for increased and/or synergistic effects when used to clean and disinfect surfaces and/or objects contaminated (or suspected of being contaminated) with biological contaminants. Suitable antimicrobial agents include carboxylic esters (e.g., p-hydroxy alkyl benzoates and alkyl cinnamates), sulfonic acids (e.g., dodecylbenzene sulfonic acid), iodo-compounds or active halogen compounds (e.g., elemental halogens, halogen oxides (e.g., $NaOCl$, $HOCl$, $HOBr$, $ClO_2$), iodine, interhalides (e.g., iodine monochloride, iodine dichloride, iodine trichloride, iodine tetrachloride, bromine chloride, iodine monobromide, or iodine dibromide), polyhalides, hypochlorite salts, hypochlorous acid, hypobromite salts, hypobromous acid, chloro- and bromo-hydantoins, chlorine dioxide, and sodium chlorite), organic peroxides including benzoyl peroxide, alkyl benzoyl peroxides, ozone, singlet oxygen generators, and mixtures thereof, phenolic derivatives (such as o-phenyl phenol, o-benzyl-p-chlorophenol, tert-amyl phenol and $C_1$-$C_6$ alkyl hydroxy benzoates), quaternary ammonium compounds (such as alkyldimethylbenzyl ammonium chloride, dialkyldimethyl ammonium chloride and mixtures thereof), and mixtures of such antimicrobial agents, in an amount sufficient to provide the desired degree of microbial protection. Effective amounts of antimicrobial agents include about 0.001 wt % to about 60 wt % antimicrobial agent, about 0.01 wt % to about 15 wt % antimicrobial agent, or about 0.08 wt % to about 2.5 wt % antimicrobial agent.

In one aspect, the peroxycarboxylic acids formed by the present process can be used to reduce the concentration of viable biological contaminants (such as a viable microbial population) when applied on and/or at a locus. As used herein, a "locus" comprises part or all of a target surface suitable for disinfecting or bleaching. Target surfaces include all surfaces that can potentially be contaminated with biological contaminants. Non-limiting examples include equipment surfaces found in the food or beverage industry (such as tanks, conveyors, floors, drains, coolers, freezers, equipment surfaces, walls, valves, belts, pipes, drains, joints, crevasses, combinations thereof, and the like); building surfaces (such as walls, floors and windows); non-food-industry related pipes and drains, including water treatment facilities, pools and spas, and fermentation tanks; hospital or veterinary surfaces (such as walls, floors, beds, equipment, (such as endoscopes) clothing worn in hospital/veterinary or other healthcare settings, including clothing, scrubs, shoes, and other hospital or veterinary surfaces); restaurant surfaces; bathroom surfaces; toilets; clothes and shoes; surfaces of barns or stables for livestock, such as poultry, cattle, dairy cows, goats, horses and pigs; hatcheries for poultry or for shrimp; and pharmaceutical or biopharmaceutical surfaces (e.g., pharmaceutical or biopharmaceutical manufacturing equipment, pharmaceutical or biopharmaceutical ingredients, pharmaceutical or biopharmaceutical excipients). Additional hard surfaces also include food products, such as beef, poultry, pork, vegetables, fruits, seafood, combinations thereof, and the like. The locus can also include water absorbent materials such as infected linens or other textiles. The locus also includes harvested plants or plant products including seeds, corms, tubers, fruit, and vegetables, growing plants, and especially crop growing plants, including cereals, leaf vegetables and salad crops, root vegetables, legumes, berried fruits, citrus fruits and hard fruits.

Non-limiting examples of hard surface materials are metals (e.g., steel, stainless steel, chrome, titanium, iron, copper, brass, aluminum, and alloys thereof), minerals (e.g., concrete), polymers and plastics (e.g., polyolefins, such as polyethylene, polypropylene, polystyrene, poly(meth)acrylate, polyacrylonitrile, polybutadiene, poly(acrylonitrile, butadiene, styrene), poly(acrylonitrile, butadiene), acrylonitrile butadiene; polyesters such as polyethylene terephthalate; and polyamides such as nylon). Additional surfaces include brick, tile, ceramic, porcelain, wood, vinyl, linoleum, and carpet.

The peroxycarboxylic acids formed by the present process may be used to provide a benefit to a textile including, but not limited to, bleaching, destaining, and deodorizing. The peroxycarboxylic acids formed by the present process may be used in any number of laundry care products including, but not limited to, textile pre-wash treatments, laundry detergents, stain removers, bleaching compositions, deodorizing compositions, and rinsing agents.

Recombinant Microbial Expression

The genes and gene products of the instant sequence(s) may be produced in heterologous host cells, particularly in the cells of microbial hosts. Preferred heterologous host cells for expression of the instant genes and nucleic acid molecules are microbial hosts that can be found within the fungal or bacterial families and which grow over a wide range of temperature, pH values, and solvent tolerances. For example, it is contemplated that any of bacteria, yeast, and filamentous fungi may suitably host the expression of the present nucleic acid molecules. The perhydrolase may be expressed intracellularly, extracellularly, or a combination of both intracellularly and extracellularly, where extracellular expression renders recovery of the desired protein from a fermentation product more facile than methods for recovery of protein produced by intracellular expression. Transcription, translation and the protein biosynthetic apparatus remain invariant relative to the cellular feedstock used to generate cellular biomass; functional genes will be expressed regardless. Examples of host strains include, but are not limited to, bacterial, fungal or yeast species such as *Aspergillus, Trichoderma, Saccharomyces, Pichia, Phaffia, Kluyveromyces, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anaebaena, Thiobacillus, Methanobacterium, Klebsiella*, and *Myxococcus*. In one embodiment, bacterial host strains include *Escherichia, Bacillus*, and *Pseudomonas*. In a preferred embodiment, the bacterial host cell is *Escherichia coli*.

Industrial Production

A variety of culture methodologies may be applied to produce the perhydrolase catalyst. For example, large-scale production of a specific gene product overexpressed from a recombinant microbial host may be produced by both batch and continuous culture methodologies. Batch and fed-batch culturing methods are common and well known in the art and examples may be found in Thomas D. Brock in *Biotechnology: A Textbook of Industrial Microbiology*, Second Edition, Sinauer Associates, inc., Sunderland, Mass. (1989) and Deshpande, Mukund V., *Appl. Biochem. Biotechnol.*, 36:227 (1992).

Commercial production of the desired perhydrolase catalyst may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added and valuable products, by-products or waste products are continuously removed from the cell mass. Cell immobilization may be performed using a wide range of solid supports composed of natural and/or synthetic materials.

Recovery of the desired perhydrolase catalysts from a batch or fed batch fermentation, or continuous culture, may be accomplished by any of the methods that are known to those skilled in the art. For example, when the enzyme catalyst is produced intracellularly, the cell paste is separated from the culture medium by centrifugation or membrane filtration, optionally washed with water or an aqueous buffer at a desired pH, then a suspension of the cell paste in an aqueous buffer at a desired pH is homogenized to produce a cell extract containing the desired enzyme catalyst. The cell extract may optionally be filtered through an appropriate filter aid such as celite or silica to remove cell debris prior to a heat-treatment step to precipitate undesired protein from the enzyme catalyst solution. The solution containing the desired enzyme catalyst may then be separated from the precipitated cell debris and protein by membrane filtration or centrifugation, and the resulting partially-purified enzyme catalyst solution concentrated by additional membrane filtration, then optionally mixed with an appropriate carrier (for example, maltodextrin, phosphate buffer, citrate buffer, or mixtures thereof) and spray-dried to produce a solid powder comprising the desired enzyme catalyst.

When an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope be limited to the specific values recited when defining a range.

General Methods

The following examples are provided to demonstrate preferred embodiments. It should be appreciated by those of skill in the art that the techniques disclosed in the examples which follow represent techniques discovered by the inventor to function well in the practice of the methods disclosed herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the presently disclosed methods.

All reagents and materials were obtained from DIFCO Laboratories (Detroit, Mich.), GIBCO/BRL (Gaithersburg, Md.), TCI America (Portland, Oreg.), Roche Diagnostics Corporation (Indianapolis, Ind.) or Sigma-Aldrich Chemical Company (St. Louis, Mo.), unless otherwise specified.

The following abbreviations in the specification correspond to units of measure, techniques, properties, or compounds as follows: "sec" or "s" means second(s), "min" means minute(s), "h" or "hr" means hour(s), "µL" means microliter(s), "mL" means milliliter(s), "L" means liter(s), "mM" means millimolar, "M" means molar, "mmol" means millimole(s), "ppm" means part(s) per million, "wt" means weight, "wt %" means weight percent, "g" means gram(s), "µg" means microgram(s), "ng" means nanogram(s), "g" means gravity, "HPLC" means high performance liquid chromatography, "dd $H_2O$" means distilled and deionized water, "dcw" means dry cell weight, "ATCC" or "ATCC®" means the American Type Culture Collection (Manassas, Va.), "U" means unit(s) of perhydrolase activity, "rpm" means revolution(s) per minute, and "EDTA" means ethylenediaminetetraacetic acid.

HPLC Method:
Supelco Discovery C8 column (10-cm×4.0-mm, 5 µm) (cat. #569422-U) w/precolumn Supelco Supelguard Discovery C8 (Sigma-Aldrich; cat #59590-U); 10 microliter injection volume; gradient method with $CH_3CN$ (Sigma-Aldrich; #270717) and deionized $H_2O$ at 1.0 mL/min and ambient temperature:

| Time (min:sec) | % $CH_3CN$ |
|---|---|
| 0:00 | 40 |
| 3:00 | 40 |
| 3:10 | 100 |
| 4:00 | 100 |
| 4:10 | 40 |
| 7:00 (stop) | 40 |

Example 1

Construction of a katG Catalase Disrupted *E. coli* Strain

The kanamycin resistance gene (kan; SEQ ID NO: 9) was amplified from the plasmid pKD13 (SEQ ID NO: 10) by PCR (0.5 min at 94° C., 0.5 min at 55° C., 1 min at 70° C., 30 cycles) using primers identified as SEQ ID NO: 11 and SEQ ID NO: 12 to generate the PCR product identified as SEQ ID NO: 13. The katG nucleic acid sequence is provided as SEQ ID NO: 14 and the corresponding amino acid sequence is SEQ ID NO: 15. *E. coli* MG1655 (ATCC® 47076™) was transformed with the temperature-sensitive plasmid pKD46 (SEQ ID NO: 16), which contains the λ-Red recombinase genes (Datsenko and Wanner, 2000, *PNAS USA* 97:6640-6645), and selected on LB-amp plates for 24 h at 30° C. MG1655/pKD46 was transformed with 50-500 ng of the PCR product by electroporation (BioRad Gene Pulser, 0.2 cm cuvette, 2.5 kV, 200 W, 25 µF), and selected on LB-kan plates for 24 h at 37° C. Several colonies were streaked onto LB-kan plates and incubated overnight at 42° C. to cure the pKD46 plasmid. Colonies were checked to confirm a phenotype of kanR/ampS. Genomic DNA was isolated from several colonies using the PUREGENE® DNA purification system (Gentra Systems, Minneapolis, Minn.), and checked by PCR to confirm disruption of the katG gene using primers identified as SEQ ID NO: 17 and SEQ ID NO: 18. Several katG-disrupted strains were transformed with the temperature-sensitive plasmid pCP20 (SEQ ID NO: 19), which contains the FLP recombinase, used to excise the kan gene, and selected on LB-amp plates for 24 h at 37° C. Several colonies were streaked onto LB plates and incubated overnight at 42° C. to cure the pCP20 plasmid. Two colonies were checked to confirm a phenotype of kanS/ampS, and called MG1655 KatG1 and MG1655 KatG2.

Example 2

Construction of a katE Catalase Disrupted *E. coli* Strain

The kanamycin resistance gene (SEQ ID NO: 9) was amplified from the plasmid pKD13 (SEQ ID NO: 10) by PCR (0.5 min at 94° C., 0.5 min at 55° C., 1 min at 70° C., 30 cycles) using primers identified as SEQ ID NO: 20 and SEQ ID NO: 21 to generate the PCR product identified as SEQ ID NO: 22. The katE nucleic acid sequence is provided as SEQ ID NO: 23 and the corresponding amino acid sequence is SEQ ID NO: 24. *E. coli* MG1655 (ATCC® 47076™) was transformed with the temperature-sensitive plasmid pKD46 (SEQ ID NO: 16), which contains the λ-Red recombinase genes, and selected on LB-amp plates for 24 h at 30° C. MG1655/pKD46 was transformed with 50-500 ng of the PCR product by electroporation (BioRad Gene Pulser, 0.2 cm cuvette, 2.5 kV, 200 W, 25 μF), and selected on LB-kan plates for 24 h at 37° C. Several colonies were streaked onto LB-kan plates and incubated overnight at 42° C. to cure the pKD46 plasmid. Colonies were checked to confirm a phenotype of kanR/ampS. Genomic DNA was isolated from several colonies using the PUREGENE® DNA purification system (Gentra Systems, Minneapolis, Minn.), and checked by PCR to confirm disruption of the katE gene using primers identified as SEQ ID NO: 25 and SEQ ID NO: 26. Several katE-disrupted strains were transformed with the temperature-sensitive plasmid pCP20 (SEQ ID NO: 19), which contains the FLP recombinase, used to excise the kan gene, and selected on LB-amp plates for 24 h at 37° C. Several colonies were streaked onto LB plates and incubated overnight at 42° C. to cure the pCP20 plasmid. Two colonies were checked to confirm a phenotype of kanS/ampS, and called MG1655 KatE1 and MG1655 KatE2

Example 3

Construction of a katG Catalase and katE Catalase Disrupted *E. coli* Strain (KLP18)

The kanamycin resistance gene (SEQ ID NO: 9) was amplified from the plasmid pKD13 (SEQ ID NO: 10) by PCR (0.5 min at 94° C., 0.5 min at 55° C., 1 min at 70° C., 30 cycles) using primers identified as SEQ ID NO: 20 and SEQ ID NO: 21 to generate the PCR product identified as SEQ ID NO: 22. *E. coli* MG1655 KatG1 (EXAMPLE 1) was transformed with the temperature-sensitive plasmid pKD46 (SEQ ID NO: 16), which contains the λ-Red recombinase genes, and selected on LB-amp plates for 24 h at 30° C. MG1655 KatG1/pKD46 was transformed with 50-500 ng of the PCR product by electroporation (BioRad Gene Pulser, 0.2 cm cuvette, 2.5 kV, 200 W, 25 μF), and selected on LB-kan plates for 24 h at 37° C. Several colonies were streaked onto LB-kan plates and incubated overnight at 42° C. to cure the pKD46 plasmid. Colonies were checked to confirm a phenotype of kanR/ampS. Genomic DNA was isolated from several colonies using the PUREGENE® DNA purification system, and checked by PCR to confirm disruption of the katE gene using primers identified as SEQ ID NO: 25 and SEQ ID NO: 26. Several katE-disrupted strains (Δ katE) were transformed with the temperature-sensitive plasmid pCP20 (SEQ ID NO: 19), which contains the FLP recombinase, used to excise the kan gene, and selected on LB-amp plates for 24 h at 37° C. Several colonies were streaked onto LB plates and incubated overnight at 42° C. to cure the pCP20 plasmid. Two colonies were checked to confirm a phenotype of kanS/ampS, and called MG1655 KatG1KatE18.1 and MG1655 KatG1KatE23. MG1655 KatG1KatE18.1 is designated *E. coli* KLP18.

Example 4

Cloning and Expression of a Perhydrolase from *Lactococcus lactis*

The gene encoding acetyl xylan esterase from *Lactococcus lactis* as reported in GENBANK® (accession # ABX75634.1) was synthesized using codons optimized for expression in *Escherichia coli* (DNA 2.0, Menlo Park, Calif.). The gene was subsequently amplified by PCR (0.5 min at 94° C., 0.5 min at 55° C., 1 min at 70° C., 30 cycles) using primers identified as SEQ ID NO: 27 and SEQ ID NO: 28. The resulting nucleic acid product (SEQ ID NO: 29) was subcloned into pTrcHis2-TOPO® (Invitrogen, Carlsbad Calif.) to generate the plasmid identified as pSW229 (SEQ ID NO: 30). The plasmid pSW229 was used to transform *E. coli* KLP18 (double catalase knockout; Example 3) to generate the strain identified as KLP18/pSW229. KLP18/pSW229 was grown in LB media at 37 C with shaking up to $OD_{600\ nm}$=0.4-0.5, at which time IPTG was added to a final concentration of 1 mM, and incubation continued for 2-3 hrs. Cells were harvested by centrifugation and SDS-PAGE was performed to confirm expression of the perhydrolase at 10-20% of total soluble protein.

Example 5

Cloning and Expression of a Perhydrolase from *Mesorhizobium loti*

The gene encoding acetyl xylan esterase from *Mesorhizobium loti* as reported in GENBANK® (accession # BAB53179.1) was synthesized using codons optimized for expression in *E. coli* (DNA 2.0). The gene was subsequently amplified by PCR (0.5 min @ 94° C., 0.5 min @ 55° C., 1 min@ 70° C., 30 cycles) using primers identified as SEQ ID NO: 31 and SEQ ID NO: 32. The resulting nucleic acid product (SEQ ID NO: 33) was subcloned into pTrcHis2-TOPO® (Invitrogen) to generate the plasmid identified as pSW231 (SEQ ID NO: 34). The plasmid pSW231 was used to transform *E. coli* KLP18 (double catalase knockout; Example 3) to generate the strain identified as KLP18/pSW231. KLP18/pSW231 was grown in LB media at 37° C. with shaking up to $OD_{600\ nm}$=0.4-0.5, at which time IPTG was added to a final concentration of 1 mM, and incubation continued for 2-3 hrs. Cells were harvested by centrifugation and SDS-PAGE was performed to confirm expression of the perhydrolase at 10-20% of total soluble protein.

Example 6

Cloning and Expression of a Perhydrolase from *Geobacillus stearothermophilus*

The gene encoding acetyl xylan esterase from *Geobacillus stearothermophilus* as reported in GENBANK® (accession # AAF70202.1) was synthesized using codons optimized for expression in *E. coli* (DNA 2.0). The gene was subsequently amplified by PCR (0.5 min at 94° C., 0.5 min at 55° C., 1 min at 70° C., 30 cycles) using primers identified as SEQ ID NO: 35 and SEQ ID NO: 36. The resulting nucleic acid product (SEQ ID NO: 37) was subcloned into pTrcHis2-TOPO® (Invitrogen) to generate the plasmid identified as pSW236 (SEQ ID NO: 38). The plasmid pSW236 was used to transform *E. coli* KLP18 (double catalase knockout) to generate the strain identified as KLP18/pSW236. KLP18/pSW236 was grown in LB media at 37° C. with shaking up to $OD_{600\ nm}$=0.4-0.5, at which time IPTG was added to a final concentration of 1 mM, and incubation continued for 2-3 hrs. Cells were harvested by centrifugation and SDS-PAGE was performed to confirm expression of the perhydrolase at 10-20% of total soluble protein.

Example 7

*Lactococcus lactis* (Lla) Perhydrolase, KLP18/pSW229

The strain KLP18/pSW229 that expresses the perhydrolase of *Lactococcus lactis* (Lla) was prepared and grown in shake flask culture incorporating IPTG induction of perhydrolase expression (Example 4). An extract of the harvested cell paste was prepared by passing a 20 wt % cell suspension in 50 mM potassium phosphate buffer (pH 7.0) twice through a French pressure cell operated at 16,000 psi (~110.32 MPa). The extract was then centrifuged at 20,000×g (5° C.) to remove cell debris and subsequently all the extract was aliquoted prior to storage at −80° C. Two 250 μL aliquots of the clarified extract were then heated at either 65° C. or 75° C. for 20 minutes followed by cooling in an ice bath. The heat-treated extracts were then centrifuged at 14,000 rpm to remove the heat-precipitated protein. A BCA assay (Bicinchoninic Acid Kit for Protein Determination, Sigma catalog #BCA1-KT; Sigma Aldrich, St. Louis, Mo.) was then performed on the clarified, heat-treated extract following the manufacturer's instructions to determine the protein concentration before and after heat-treatment. The results are shown in Table 4 below.

TABLE 4

KLP18/pSW229 BCA Assay Results

| Sample | [Protein] mg/mL | % Recovery |
| --- | --- | --- |
| Pre-heat | 21.4 | 100 |
| 65° C. | 8.9 | 42 |
| 75° C. | 2.2 | 10.3 |

An SDS-PAGE was performed to assess the *Lactococcus lactis* perhydrolase as a percentage of total soluble protein. The protein loading for the pre-heated, 65° C. heat-treated, and the 75° C. heat-treated extracts was 15 μg/lane. The 65° C. heat-treated sample had an estimated purity of 85-90%. Heat-treatment at 75° C. for 20 minutes resulted in disappearance of perhydrolase protein from the clarified extract.

For determination of specific activity, reactions were run using triacetin (250 mM), hydrogen peroxide (1000 mM), phosphate buffer (50 mM, pH 7.2) and either 15 μg/mL of 65° C. clarified extract protein or 20 μg/mL of 75° C. heat-treated, clarified extract protein. The reactions were sampled at 1, 2, 3, 4, and 5 minutes followed by analysis using the Karst derivatization protocol (Karst et al., supra); aliquots (0.040 mL) of the reaction mixture were removed and mixed with 0.960 mL of 5 mM phosphoric acid in water; adjustment of the pH of the diluted sample to less than pH 4 immediately terminated the reaction. The resulting solution was filtered using an ULTRAFREE® MC-filter unit (30,000 Normal Molecular Weight Limit (NMWL), Millipore cat #UFC3LKT 00) by centrifugation for 2 min at 12,000 rpm. An aliquot (0.100 mL) of the resulting filtrate was transferred to 1.5-mL screw cap HPLC vial (Agilent Technologies, Palo Alto, Calif.; #5182-0715) containing 0.300 mL of deionized water, then 0.100 mL of 20 mM MTS (methyl-p-tolyl-sulfide) in acetonitrile was added, the vials capped, and the contents briefly mixed prior to a 10 min incubation at ca. 25° C. in the absence of light. To each vial was then added 0.400 mL of acetonitrile and 0.100 mL of a solution of triphenylphosphine (TPP, 40 mM) in acetonitrile, the vials re-capped, and the resulting solution mixed and incubated at ca. 25° C. for 30 min in the absence of light. To each vial was then added 0.100 mL of 10 mM N,N-diethyl-m-toluamide (DEET; HPLC external standard) and the resulting solution analyzed by HPLC.

Control reactions were also performed without added perhydrolase to evaluate the relative rate of chemical perhydrolysis. The reaction containing protein that was heat-treated at 65° C. produced 1100 ppm PAA in 1 min, and no further PAA was produced at 2, 3, 4, or 5 min. The reaction containing the protein that was heat-treated at 75° C. produced no significant concentration of PAA relative to the control reaction without enzyme.

Example 8

*Mesorhizobium loti* Perhydrolase (Mlo; KLP18/pSW231)

The strain KLP18/pSW231 that expresses the perhydrolase of *Mesorhizobium loti* was prepared and grown in shake flask culture incorporating IPTG induction of perhydrolase expression (Example 5). A 20 wt % cell suspension was then prepared using 50 mM potassium phosphate buffer (pH 7.0) containing 1 mM dithiothreitol. The uniform cell suspension was then passed twice through a French pressure cell operated at 16,000 psi (~110.32 MPa). The crude extract was then centrifuged for 25 minutes at 20,000×g (5° C.) to remove cell debris. The extract was then aliquoted into several Eppendorf test tubes that each contained 250 μL of extract. Two of these extract samples were then heated at 65° C. or 75° C. for 20 minutes. Following each heat-treatment the heat-precipitated protein of each sample was removed following centrifugation at 14,000 rpm. A Bradford Assay (Sigma Aldrich, St. Louis, Mo.) was then performed to determine the protein concentration of pre- and post-heat treatment samples. The results are shown in Table 5.

TABLE 5

KLP18/pSW231 Bradford Assay Results

| Sample | [Protein] mg/mL | % protein recovery |
| --- | --- | --- |
| Pre-heat | 17.6 | 100 |
| Post-heat 65° C. | 3.2 | 18.2 |
| Post-heat 75° C. | 1.3 | 7.3 |

SDS-PAGE was performed to assess the degree of perhydrolase purification. The perhydrolase band that was identified as the *Mesorhizobium loti* perhydrolase disappeared following heat-treatment of extracts at either 65° C. or 75° C., indicating that the *Mesorhizobium loti* perhydrolase was denatured at these temperatures. SDS-PAGE of clarified, un-heated extract indicated a low level of perhydrolase expression (approximately 5% of total soluble protein). For determination of perhydrolase specific activity, reactions were run containing triacetin (250 mM), hydrogen peroxide (1000 mM), phosphate buffer (50 mM, pH 7.2), and clarified extract un-heated protein (100 μg/mL). The reaction (25° C.) was sampled every minute for five minutes. The samples were analyzed for peracetic acid (PAA) production using the Karst derivatization protocol (Karst et al., supra) followed by HPLC analysis. The specific activity was 3.9 U/mg.

A second shake-flask growth protocol was used for improved expression of Mlo perhydrolase. The protocol includes a seed stage in 125-mL disposable baffled flasks with 10 mL of medium, and a production stage in two 1-L baffled flasks with 250 mL of medium in each flask. The medium for the seed flask contained yeast extract (Difco, 5.0 g/L), $K_2HPO_4$ (10.0 g/L), $KH_2PO_4$ (7.0 g/L), sodium citrate dihydrate (1.0 g/L), $(NH_4)_2SO_4$ (4.0 g/L) and ferric ammonium citrate (0.10 g/L). The pH of the medium was adjusted to 6.8 and the medium sterilized by filtration through a 0.2-micron filter. Post sterilization additions included glucose 5 g/L, trace elements solution (5 mL/L), $MgSO_4$ (5 mM), and ampicillin (50 μg/mL). The trace elements solution contained citric acid monohydrate (10 g/L), MnSO$_4$ hydrate (2 g/L), NaCl (2 g/L), FeSO$_4$ heptahydrate (0.5 g/L), ZnSO$_4$ heptahydrate (0.2 g/L), CuSO$_4$ pentahydrate (0.02 g/L) and NaMoO$_4$ dihydrate (0.02 g/L). The seed flask was inoculated with 1 mL frozen stock and incubated to 7 OD$_{550}$. Seed and production flasks were incubated in incubator shaker at 37° C. and 300 rpm. The medium for the production flasks was the same as the seed flask except that the concentration of yeast extract was reduced to 2 g/L. Each production flask was seeded with 7 mL of seed culture. IPTG was added to 0.1 mM at about 3 OD$_{550}$, then incubation continued for 12 h, where growth proceeded to about 9 OD. The cells were harvested by centrifugation, and the cell pellet frozen for further processing at –80° C. An extract was prepared from this harvested cell paste as described above. Based on the SDS-PAGE gel, the perhydrolase was estimated to represent approximately 10% of total soluble clarified extract protein. The specific activity was determined using the Karst derivatization protocol (Karst et al., supra) followed by HPLC analysis, and the specific activity was 3.6 U/mg protein.

Example 9

*Geobacillus stearothermophilus* (Gst; KLP18/pSW236): Perhydrolase Evaluation

*Geobacillus stearothermophilus* (Gst; KLP18/pSW236) was grown and induced in shake flasks followed by extract preparation as described above (Example 7). A sample (250 μL) of the extract was then heated for 20 minutes at either 65° C. or 75° C. followed by centrifugation to remove heat-precipitated protein. SDS-PAGE was performed to estimate perhydrolase purity in heated and un-heated clarified extracts. Based on the SDS-PAGE gel, the perhydrolase was estimated to represent less than 5% of the soluble protein of unheated and heated extract (75° C.). The perhydrolase in the clarified extract heat-treated at 65° C. was estimated to represent 15-20% of total soluble protein.

Specific activity was determined following reactions (25° C.) containing TA (250 mM), hydrogen peroxide (1000 mM), potassium phosphate buffer (50 mM, pH 7.2), and 100 μg/mL of clarified, unheated or heat-treated (65° C.) extract protein. Five minute reactions were performed with 1 minute sampling followed by the Karst derivatization protocol (Karst et al., supra) and HPLC analysis. The specific activity was determined to be 4.4 U/mg unheated protein and 3.3 U/mg of heat-treated protein. If *Geobacillus stearothermophilus* perhydrolase was thermostable, the specific activity of the heat-treated protein would be expected to be higher than that of the unheated protein. The specific activity of the clarified, heat-treated extract protein was lower than that of the clarified, unheated extract protein, indicating that the perhydrolase was only moderately stable at 65° C.

Example 10

Peracetic Acid Production Using Perhydrolase from *Lactococcus lactis*

A cell extract of a transformant expressing perhydrolase from *Lactococcus lactis* (KLP18/pSW229) was prepared (Example 7). The crude extract was then centrifuged at 20,000×g and 5° C. to remove cellular debris, producing a clarified cell extract that was assayed for total soluble protein (Bicinchoninic Acid Kit for Protein Determination, Sigma-Aldrich, catalog #BCA1-KT). The clarified extract was heated for 20 min at 65° C., followed immediately by cooling in an ice/water bath. The resulting mixture was centrifuged to remove precipitated protein, and the clarified, heat-treated cell extract was collected and assayed for total soluble protein as before. SDS-PAGE of the clarified, heat-treated cell extract indicated that the perhydrolase was at least 85-90% pure. The clarified, heat-treated cell extract was assayed for total soluble protein as before, frozen in dry ice and stored at –80° C.

Reactions (2 mL total volume) containing triacetin, hydrogen peroxide and 50 μg/mL of total protein from a heat-treated, centrifuged cell extract (8.8 mg/mL) (prepared as described above) in 50 mM sodium phosphate buffer (pH 7.2) or 50 mM sodium bicarbonate buffer (pH 8.5) were run at 24° C. A control reaction for each reaction condition was run to determine the concentration of peracetic acid produced by chemical perhydrolysis of triacetin by hydrogen peroxide in the absence of added extract protein. The concentration of peracetic acid in the reaction mixtures was determined according to the method of Karst et al. as described in Example 7. The peracetic acid concentrations produced in 1 min, 5 min and 30 min in 50 mM sodium phosphate buffer (pH 7.2) are listed in Table 6, and in 50 mM sodium bicarbonate buffer (pH 8.5) are listed in Table 7. The concentration of peracetic acid produced by the *Lactococcus lactis* perhydrolase did not increase significantly after 5 to 30 minutes of reaction, whereas the concentration of peracetic acid produced under similar reaction conditions by the *M. loti, G. stearothermophilus, T. neapolitana, T. maritima, B. subtilis* and *B. pumilus* perhydrolases typically continued to increase after 5 min of reaction (see Examples 11-15, below).

TABLE 6

Dependence of peracetic acid (PAA) concentration on concentrations of triacetin (TA), hydrogen peroxide and total protein from a clarified, heat-treated (65° C.) cell extract prepared from a transformant expressing perhydrolase from *Lactococcus lactis* (*E. coli* KLP18/pSW229); phosphate buffer (50 mM, pH 7.2).

| total protein (μg/mL) | H$_2$O$_2$ (mM) | TA (mM) | PAA, 1 min (ppm) | pH 1 min | PAA, 5 min (ppm) | pH 5 min | PAA, 30 min (ppm) | pH, 30 min |
|---|---|---|---|---|---|---|---|---|
| 0 | 250 | 250 | 31 | 7.2 | 138 | 7.2 | 98 | 7.2 |
| 50 | 250 | 250 | 1307 | 7.0 | 1280 | 7.0 | 1336 | 7.0 |
| 0 | 250 | 100 | 57 | 7.2 | 70 | 7.2 | 189 | 7.2 |
| 50 | 250 | 100 | 968 | 7.0 | 1105 | 7.0 | 963 | 7.0 |
| 0 | 500 | 100 | 54 | 7.2 | 53 | 7.2 | 226 | 7.2 |
| 50 | 500 | 100 | 1137 | 7.0 | 1067 | 7.0 | 842 | 7.0 |
| 0 | 250 | 50 | 4 | 7.2 | 69 | 7.2 | 28 | 7.2 |
| 50 | 250 | 50 | 689 | 7.0 | 681 | 7.0 | 515 | 7.0 |
| 0 | 100 | 100 | 0 | 7.2 | 35 | 7.2 | 70 | 7.2 |
| 50 | 100 | 100 | 595 | 7.0 | 960 | 7.0 | 905 | 7.0 |
| 0 | 50 | 100 | 0 | 7.2 | 0 | 7.2 | 31 | 7.2 |
| 50 | 50 | 100 | 394 | 7.0 | 589 | 7.0 | 633 | 7.0 |

TABLE 7

Dependence of peracetic acid (PAA) concentration on concentrations of triacetin (TA), hydrogen peroxide and total protein from a clarified, heat-treated (65° C.) cell extract prepared from a transformant expressing perhydrolase from *Lactococcus lactis* (*E. coli* KLP18/pSW229); 50 mM sodium bicarbonate buffer (pH 8.5).

| total protein (μg/mL) | H$_2$O$_2$ (mM) | TA (mM) | PAA, 1 min (ppm) | pH 1 min | PAA, 5 min (ppm) | pH 5 min | PAA, 30 min (PPm) | pH, 30 min |
|---|---|---|---|---|---|---|---|---|
| 0 | 100 | 100 | 54 | 8.5 | 262 | 8.0 | 348 | 7.5 |
| 50 | 100 | 100 | 613 | 7.0 | 879 | 7.0 | 601 | 7.0 |

Example 11

Peracetic Acid Production Using Perhydrolase from *Mesorhizobium loti* (Comparative)

A cell extract of a transformant expressing perhydrolase from *Mesorhizobium loti* (KLP18/pSW231) was prepared as described in Example 8, using cells prepared by the shake-flask growth protocol for improved expression of Mlo perhydrolase. The clarified, un-heated cell extract was frozen in dry ice and stored at −80° C.

Reactions (2 mL total volume) containing triacetin, hydrogen peroxide and 500 μg/mL of total protein from a clarified, un-heated cell extract (22.8 mg/mL) (prepared as described above) in 50 mM sodium phosphate buffer (pH 7.2) were run at 24° C. A control reaction was run to determine the concentration of peracetic acid produced by chemical perhydrolysis of triacetin by hydrogen peroxide in the absence of added extract protein. The concentration of peracetic acid in the reaction mixtures was determined according to the method of Karst et al., supra. The peracetic acid concentrations produced in 1 min, 5 min and 30 min are listed in Table 8.

TABLE 8

Dependence of peracetic acid (PAA) concentration on concentrations of triacetin (TA), hydrogen peroxide and total protein from a clarified, un-heated cell extract prepared from a transformant expressing perhydrolase from *Mesorhizobium loti* (*E. coli* KLP18/pSW231); 50 mM sodium phosphate buffer (pH 7.2).

| total protein (μg/mL) | $H_2O_2$ (mM) | TA (mM) | PAA, 1 min (ppm) | pH 1 min | PAA, 5 min (ppm) | pH 5 min | PAA, 30 min (ppm) | pH, 30 min |
|---|---|---|---|---|---|---|---|---|
| 0 | 250 | 250 | 31 | 7.2 | 138 | 7.2 | 98 | 7.2 |
| 500 | 250 | 250 | 137 | 7.0 | 652 | 7.0 | 1664 | 7.0 |
| 0 | 250 | 100 | 57 | 7.2 | 70 | 7.2 | 189 | 7.2 |
| 500 | 250 | 100 | 90 | 7.0 | 535 | 7.0 | 1286 | 7.0 |
| 0 | 500 | 100 | 54 | 7.2 | 53 | 7.2 | 226 | 7.2 |
| 500 | 500 | 100 | 235 | 7.0 | 705 | 7.0 | 1627 | 7.0 |
| 0 | 250 | 50 | 4 | 7.2 | 69 | 7.2 | 28 | 7.2 |
| 500 | 250 | 50 | 71 | 7.0 | 269 | 7.0 | 1015 | 7.0 |
| 0 | 100 | 100 | 0 | 7.2 | 35 | 7.2 | 70 | 7.2 |
| 50 | 100 | 100 | 34 | 7.0 | 211 | 7.0 | 702 | 7.0 |
| 0 | 50 | 100 | 0 | 7.2 | 0 | 7.2 | 31 | 7.2 |
| 500 | 50 | 100 | 0 | 7.0 | 53 | 7.0 | 294 | 7.0 |

Example 12

Peracetic Acid Production Using Perhydrolase from *Geobacillus stearothermophilus* (Comparative)

A cell extract of a transformant expressing perhydrolase from *Geobacillus stearothermophilus* (KLP18/pSW236) was prepared as described in Example 9. The clarified, unheated cell extract was frozen in dry ice and stored at −80° C.

Reactions (2 mL total volume) containing triacetin, hydrogen peroxide and 500 μg/mL of total protein from a clarified, un-heated cell extract (21.4 mg/mL (prepared as described above) in 50 mM sodium phosphate buffer (pH 7.2) were run at 24° C. A control reaction for each reaction condition was run to determine the concentration of peracetic acid produced by chemical perhydrolysis of triacetin by hydrogen peroxide in the absence of added extract protein. The concentration of peracetic acid in the reaction mixtures was determined according to the method of Karst et al., supra. The peracetic acid concentrations produced in 1 min, 5 min and 30 min are listed in Table 9.

TABLE 9

Dependence of peracetic acid (PAA) concentration on concentrations of triacetin (TA), hydrogen peroxide and total protein from a clarified, un-heated cell extract prepared from transformant expressing perhydrolase from *Geobacillus stearothermophilus* (*E. coli* KLP18/pSW236); 50 mM sodium phosphate buffer (pH 7.2).

| total protein (μg/mL) | $H_2O_2$ (mM) | TA (mM) | PAA, 1 min (ppm) | pH 1 min | PAA, 5 min (ppm) | pH 5 min | PAA, 30 min (ppm) | pH, 30 min |
|---|---|---|---|---|---|---|---|---|
| 0 | 250 | 250 | 31 | 7.2 | 138 | 7.2 | 98 | 7.2 |
| 500 | 250 | 250 | 82 | 7.0 | 252 | 7.0 | 702 | 7.0 |
| 0 | 250 | 100 | 57 | 7.2 | 70 | 7.2 | 189 | 7.2 |
| 500 | 250 | 100 | 0 | 7.0 | 85 | 7.0 | 398 | 7.0 |
| 0 | 500 | 100 | 54 | 7.2 | 53 | 7.2 | 226 | 7.2 |
| 500 | 500 | 100 | 82 | 7.0 | 108 | 7.0 | 348 | 7.0 |
| 0 | 250 | 50 | 4 | 7.2 | 69 | 7.2 | 28 | 7.2 |
| 500 | 250 | 50 | 0 | 7.0 | 0 | 7.0 | 249 | 7.0 |
| 0 | 100 | 100 | 0 | 7.2 | 35 | 7.2 | 70 | 7.2 |
| 50 | 100 | 100 | 35 | 7.0 | 67 | 7.0 | 201 | 7.0 |
| 0 | 50 | 100 | 0 | 7.2 | 0 | 7.2 | 31 | 7.2 |
| 500 | 50 | 100 | 162 | 7.0 | 174 | 7.0 | 51 | 7.0 |

Example 13

Peracetic Acid Production by *Thermotoga neapolitana* Perhydrolase (Comparative)

A cell extract of an *E. coli* transformant expressing perhydrolase from *Thermotoga neapolitana* (KLP18/pSW196) was prepared by passing a suspension of cell paste (20 wt % wet cell weight) in 50 mM potassium phosphate buffer (pH 7.0) containing dithiothreitol (1 mM) twice through a French press having a working pressure of 16,000 psi (~110 MPa). The crude extract was then centrifuged at 20,000×g to remove cellular debris, producing a clarified cell extract that was assayed for total soluble protein (Bicinchoninic Acid Kit for Protein Determination, Sigma-Aldrich). The clarified extract was heated for 20 min at 75° C., followed immediately by cooling in an ice/water bath. The resulting mixture was centrifuged to remove precipitated protein, and the clarified, heat-treated cell extract collected and assayed for total soluble protein as before. SOS-PAGE of the clarified, heat-treated cell extract indicated that the perhydrolase was at least 90% pure. The clarified, heat-treated cell extract was frozen in dry ice and stored at −80° C.

Reactions (10 mL total volume) containing triacetin, hydrogen peroxide and 50 μg/mL of clarified, heat-treated cell extract (prepared as described above) were run at 25° C. using 25 mM bicarbonate buffer (initial reaction pH ca. 8.1). A control reaction for each reaction condition was run to determine the concentration of peracetic acid produced by chemical perhydrolysis of triacetin by hydrogen peroxide in the absence of added extract protein. Determination of the concentration of peracetic acid in the reaction mixtures was performed according to the method described by Karst et al., supra. The peracetic acid concentrations produced in 1 min, 5 min and 30 min when using either 250 mM or 100 mM hydrogen peroxide are listed in Table 10.

TABLE 10

Dependence of peracetic acid (PAA) concentration on reaction time in 25 mM bicarbonate buffer (initial reaction pH ca. 8.1) using 50 μg/mL of E. coli KLP18/pSW196 heat-treated extract total protein containing *Thermotoga neapolitana* perhydrolase.

| heated extract total protein (μg protein/mL) | triacetin (mM) | H₂O₂ (mM) | PAA (ppm), 1 min | pH, 1 min | PAA (ppm), 5 min | pH, 5 min | PAA (ppm), 30 min | pH, 30 min |
|---|---|---|---|---|---|---|---|---|
| 0  | 100 | 250 | 139  | 8.0 | 385  | 7.5 | 610  | 7.2 |
| 50 | 100 | 250 | 1037 | 6.8 | 2655 | 6.0 | 3503 | 5.8 |
| 0  | 100 | 100 | 74   | 8.0 | 220  | 7.8 | 383  | 7.5 |
| 50 | 100 | 100 | 497  | 7.5 | 1319 | 6.5 | 2095 | 6.0 |

Example 14

Peracetic Acid Production by *Thermotoga maritima* MSB8 Perhydrolase (Comparative)

A cell extract of a transformant expressing perhydrolase from *Thermotoga maritima* MSB8 (KLP18/pSW207) was prepared by passing a suspension of cell paste (20 wt % wet cell weight) in 0.05 M potassium phosphate buffer (pH 7.0) containing dithiothreitol (1 mM) twice through a French press having a working pressure of 16,000 psi (~110 MPa). The crude extract was then centrifuged at 20,000×g to remove cellular debris, producing a clarified cell extract that was assayed for total soluble protein (Bicinchoninic Acid Kit for Protein Determination, Sigma-Aldrich). The clarified extract was heated for 20 min at 75° C., followed immediately by cooling in an ice/water bath. The resulting mixture was centrifuged to remove precipitated protein, and the clarified, heat-treated cell extract collected and assayed for total soluble protein as before. SDS-PAGE of the clarified, heat-treated cell extract indicated that the perhydrolase was at least 85-90% pure. The clarified, heat-treated cell extract was frozen in dry ice and stored at −80° C.

Reactions (2 mL total volume) containing triacetin, hydrogen peroxide and clarified, heat-treated cell extract (prepared as described above) were run at 25° C. using 25 mM sodium bicarbonate buffer (initial pH ca. 8.1). A control reaction for each reaction condition was run to determine the concentration of peracetic acid produced by chemical perhydrolysis of triacetin by hydrogen peroxide in the absence of added extract protein. Determination of the concentration of peracetic acid in the reaction mixtures was performed according to the method described by Karst et al., supra. The peracetic acid concentrations produced in 1 min, 5 min and 30 min using either 250 mM or 100 mM hydrogen peroxide are listed in Table 11.

Example 15

Peracetic Acid Production by Perhydrolase (Comparative)

A cell extract of a transformant expressing perhydrolase from *Bacillus pumilus* PS213 (KLP18/pSW195), *Thermotoga maritima* MSB8 (KLP18/pSW207), *Thermotoga neapolitana* (KLP18/pSW196), or *Bacillus subtilis* ATCC 31954™ (KLP18/pSW194) was prepared by passing a suspension of cell paste (20 wt % wet cell weight) in 0.05 M potassium phosphate buffer (pH 7.0) containing dithiothreitol (1 mM) twice through a French press having a working pressure of 16,000 psi (~110 MPa). The crude extract was then centrifuged at 20,000×g to remove cellular debris, producing a clarified cell extract that was assayed for total soluble protein (Bicinchoninic Acid Kit for Protein Determination, Sigma-Aldrich). The supernatant was frozen in dry ice and stored at −80° C.

Reactions (10 mL total volume) containing triacetin, hydrogen peroxide and centrifuged cell extract supernatant (prepared as described above) in 50 mM sodium citrate buffer (initial pH 7.2 or 6.5) were run at 25° C. A control reaction for each reaction condition was run to determine the concentration of peracetic acid produced by chemical perhydrolysis of triacetin by hydrogen peroxide in the absence of added extract protein (data not shown). Determination of the concentration of peracetic acid in the reaction mixtures was performed according to the method described by Karst at al., supra. The peracetic acid concentrations produced in 1 min, 5 min and 30 min are listed in Table 13.

TABLE 11

Dependence of peracetic acid (PAA) concentration on reaction time in 25 mM bicarbonate buffer (initial reaction pH = 8.1) using 50 μg/mL of E. coli KLP18/pSW207 heat-treated extract total protein containing *Thermotoga maritima* MSB8 perhydrolase.

| heated extract total protein (μg protein/mL) | triacetin (mM) | H₂O₂ (mM) | PAA (ppm), 1 min | pH, 1 min | PAA (ppm), 5 min | pH, 5 min | PAA (ppm), 30 min | pH, 30 min |
|---|---|---|---|---|---|---|---|---|
| 0  | 100 | 250 | 144 | 8.0 | 324  | 8.0 | 759  | 7.2 |
| 50 | 100 | 250 | 848 | 7.0 | 2342 | 6.5 | 3251 | 6.0 |
| 0  | 100 | 100 | 95  | 8.0 | 223  | 8.0 | 456  | 7.5 |
| 50 | 100 | 100 | 465 | 7.5 | 1369 | 6.8 | 2217 | 6.0 |

TABLE 13

Dependence of peracetic acid (PAA) concentration on initial reaction pH in sodium citrate buffer (50 mM, initial pH of 7.2 or 6.5) at 25° C. using 50 μg/mL of extract total protein from *E. coli* KLP18/pSW195 (*Bacillus pumilus* PS213 perhydrolase), *E. coli* KLP18/pSW207 (*Thermotoga maritima* MSB8 perhydrolase), *E. coli* KLP18/pSW196 (*Thermotoga neapolitana* perhydrolase), or *E. coli* KLP18/pSW194 (*Bacillus subtilis* ATCC 31954 ™ perhydrolase).

| perhydrolase | initial pH | triacetin (mM) | $H_2O_2$ (mM) | PAA, 1 min (ppm) | PAA, 5 min (ppm) | PAA, 30 min (ppm) |
|---|---|---|---|---|---|---|
| *B. pumilus* PS213 | 7.2 | 100 | 250 | 465 | 1170 | 2525 |
| *B. pumilus* PS213 | 6.5 | 100 | 250 | 281 | 652 | 1984 |
| *B. pumilus* PS213 | 7.2 | 100 | 100 | 160 | 322 | 1010 |
| *B. pumilus* PS213 | 6.5 | 100 | 100 | 170 | 310 | 830 |
| *T. neapolitana* | 7.2 | 100 | 250 | 1790 | 2860 | 3820 |
| *T. neapolitana* | 6.5 | 100 | 250 | 434 | 1260 | 2016 |
| *T. neapolitana* | 7.2 | 100 | 100 | 798 | 1748 | 2500 |
| *T. neapolitana* | 6.5 | 100 | 100 | 221 | 607 | 1925 |
| *T. maritima* MSB8 | 7.2 | 100 | 250 | 635 | 1725 | 3565 |
| *T. maritima* MSB8 | 6.5 | 100 | 250 | 95 | 742 | 2446 |
| *T. maritima* MSB8 | 7.2 | 100 | 100 | 210 | 610 | 1995 |
| *T. maritima* MSB8 | 6.5 | 100 | 100 | 53 | 279 | 1540 |
| *B. subtilis* ATCC 31954 | 7.2 | 100 | 250 | 2430 | 2820 | 4400 |
| *B. subtilis* ATCC 31954 | 6.5 | 100 | 250 | 1725 | 2570 | 3712 |
| *B. subtilis* ATCC 31954 | 7.2 | 100 | 100 | 1040 | 1240 | 2395 |
| *B. subtilis* ATCC 31954 | 6.5 | 100 | 100 | 691 | 1286 | 1880 |

What is claimed is:

1. A process for producing a target concentration of peroxycarboxylic acid comprising:
   (a) selecting a set of reaction components comprising:
      (1) at least one substrate selected from the group consisting of:
         (i) esters having the structure $[X]_m R_5$ wherein
         X = an ester group of the formula $R_5$—C(O)O;
         $R_6$ = C1 to C7 linear, branched or cyclic hydrocarbyl moiety, optionally substituted with hydroxyl groups or C1 to C4 alkoxy groups, wherein $R_6$ optionally comprises one or more ether linkages for $R_6$ = C2 to C7;
         $R_5$ = a C1 to C6 linear, branched, or cyclic hydrocarbyl moiety optionally substituted with hydroxyl groups; wherein each carbon atom in $R_5$ individually comprises no more than one hydroxyl group or no more than one ester group;
         wherein $R_5$ optionally comprises one or more ether linkages;
         m = 1 to the number of carbon atoms in $R_5$; and
         wherein said esters have solubility in water of at least 5 ppm at 25° C.;
         (ii) glycerides having the structure

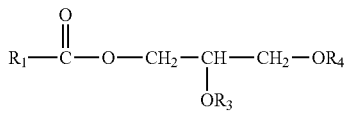

wherein $R_1$ = $C_1$ to $C_7$ straight chain or branched chain alkyl optionally substituted with an hydroxyl or a C1 to C4 alkoxy group and $R_3$ and $R_4$ are individually H or $R_1$C(O); and (iii) acetylated saccharides selected from the group consisting of acetylated monosaccharides, acetylated disaccharides, and acetylated polysaccharides;
      (2) a source of peroxygen; and
      (3) an enzyme catalyst having perhydrolysis activity, wherein said enzyme catalyst comprises an enzyme having a signature motif that aligns with a reference sequence SEQ ID NO:2 using CLUSTALW, said signature motif comprising:
         (i) an RGQ motif at amino acid positions 118-120 of SEQ ID NO:2;
         (ii) a GXSQG motif at amino acid positions 179-183 of SEQ ID NO:2; and
         (iii) an HE motif at amino acid positions 298-299 of SEQ ID NO:2;
         wherein said enzyme has at least 95% amino acid identity to SEQ ID NO:4; and
   (b) combining the reaction components under aqueous reactions to form a reaction mixture; whereby reaction products are formed comprising enzymatically-produced peroxycarboxylic acid; wherein
      (1) the pH of the reaction mixture remains in the range of from about 6.0 to about 9.0; and
      (2) the concentration of peroxycarboxylic acid produced one minute after combining the reaction components is not exceeded by more than 100% at a reaction time equal to or greater than five minutes after combining the reaction components.

2. The process of claim 1 wherein the concentration of peroxycarboxylic acid produced one minute after combining the reaction components is not exceeded by more than 100% at a reaction time equal to or greater than 30 minutes after combining the reaction components.

3. The process of claim 1 wherein the concentration of peroxycarboxylic acid produced one minute after combining the reaction components is not exceeded by more than 50% at a reaction time equal to or greater than five minutes after combining the reaction components.

4. The process of claim 3 wherein the concentration of peroxycarboxylic acid produced one minute after combining the reaction components is not exceeded by more than 20% at a reaction time equal to or greater than five minutes after combining the reaction components.

5. The process of claim 1 wherein the total amount of peroxycarboxylic acid produced by the process is not limited by the amount of substrate or the amount of peroxygen in the reaction mixture.

6. The process of claim 1 wherein the pH of the reaction mixture ranges from about 6.5 to about 8.5.

7. The process of claim 6 wherein the pH of the reaction mixture ranges from about 7.0 to about 8.0.

8. The process of claim 1 wherein the reaction mixture comprises at least one buffer.

9. The process of claim 8 wherein the at least one buffer is selected from the group consisting of sodium bicarbonate, potassium bicarbonate, mixtures of sodium bicarbonate and potassium bicarbonate, sodium phosphate, potassium phosphate, and mixtures of sodium phosphate and potassium phosphate.

10. The process of claim 1 wherein the substrate is selected from the group consisting of: monoacetin; diacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-glucal; monoesters or diesters of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,6-pentanediol; 1,2-hexanediol; 2,5-hexanediol; 1,6-hexanediol; propylene glycol diacetate; ethylene glycol diacetate; and mixtures thereof.

11. The process of claim 1 wherein the peroxycarboxylic acid produced is peracetic acid, perpropionic acid, perbutyric acid, perlactic acid, perglycolic acid, permethoxyacetic acid, per-β-hydroxybutyric acid, or mixtures thereof.

12. The process of claim 1 wherein the enzyme catalyst is in the form of a microbial cell, a permeabilized microbial cell, a microbial cell extract, a partially purified enzyme, or a purified enzyme.

13. The process of claim 1 wherein the enzyme catalyst lacks catalase activity.

14. The process of claim 1 further comprising the step of: (c) contacting a surface or inanimate object with the peroxycarboxylic acid produced in step (b) whereby said surface or said inanimate object is disinfected, destained, deodorized or bleached.

15. The process of claim 1 further comprising the step of: (c) contacting a textile with peroxycarboxylic acid produced in step (b), whereby the textile receives a benefit.

16. The process of claim 15 wherein the benefit is selected from the group consisting of a disinfecting, bleaching, destaining, deodorizing, and any combination thereof.

17. A process for producing a target concentration of peroxycarboxylic acid comprising:
(a) selecting a set of reaction components comprising:
(1) at least one substrate selected from the group consisting of:
(i) esters having the structure $$[X]_m R_5$$

wherein
X=an ester group of the formula $R_6$—C(O)O;
$R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;
$R_5$=a C1 to C6 linear, branched, or cyclic hydrocarbyl moiety optionally substituted with hydroxyl groups; wherein each carbon atom in $R_5$ individually comprises no more than one hydroxyl group or no more than one ester group;
wherein $R_5$ optionally comprises one or more ether linkages;
m=1 to the number of carbon atoms in $R_5$; and wherein said esters have solubility in water of at least 5 ppm at 25° C.;
(ii) glycerides having the structure

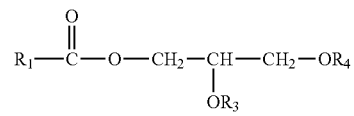

wherein $R_1$=$C_1$ to $C_7$ straight chain or branched chain alkyl optionally substituted with an hydroxyl or a C1 to C4 alkoxy group and $R_3$ and $R_4$ are individually H or $R_1$C(O); and
(iii) acetylated saccharides selected from the group consisting of acetylated monosaccharides, acetylated disaccharides, and acetylated polysaccharides;
(2) a source of peroxygen; and
(3) an enzyme catalyst having perhydrolysis activity, wherein said enzyme catalyst comprises an enzyme having a signature motif that aligns with a reference sequence SEQ ID NO:2 using CLUSTALW, said signature motif comprising:
(i) an RGQ motif at amino acid positions 118-120 of SEQ ID NO:2;
(ii) a GXSQG motif at amino acid positions 179-183 of SEQ ID NO:2; and
(iii) an HE motif at amino acid positions 298-299 of SEQ ID NO:2;
wherein said enzyme has at least 95% amino acid identity to SEQ ID NO:4; and
(b) combining the selected set of reaction components under aqueous reaction conditions to form a reaction mixture; whereby reaction products are formed comprising enzymatically-produced peroxycarboxylic acid; wherein
(1) the pH of the aqueous reaction mixture remains in the range of from about 6.0 to about 9.0; and
(2) the concentration of peroxycarboxylic acid produced five minutes after combining the reaction components is not exceeded by more than 100% at a reaction time equal to or greater than 30 minutes after combining the reaction components.

18. The process of claim 17 wherein concentration of peroxycarboxylic acid produced five minutes after combining the reaction components is not exceeded by more than 50% at a reaction time equal to or greater than 30 minutes after combining the reaction components.

19. The process of claim 18 wherein the concentration of peroxycarboxylic acid produced five minutes after combining the reaction components is not exceeded by more than 20% at a reaction time equal to or greater than 30 minutes after combining the reaction components.

20. A composition comprising:
(a) a set of reaction components comprising:
(1) at least one substrate selected from the group consisting of:

(i) esters having the structure $[X]_m R_5$ wherein

X=an ester group of the formula $R_6$—C(O)O;

$R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;

$R_5$=a C1 to C6 linear, branched, or cyclic hydrocarbyl moiety optionally substituted with hydroxyl groups; wherein each carbon atom in $R_5$ individually comprises no more than one hydroxyl group or no more than one ester group;

wherein $R_5$ optionally comprises one or more ether linkages;

m=1 to the number of carbon atoms in $R_5$; and wherein said esters have solubility in water of at least 5 ppm at 25° C.;

(ii) glycerides having the structure

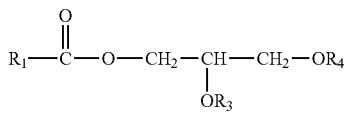

wherein $R_1$=$C_1$ to $C_7$ straight chain or branched chain alkyl optionally substituted with an hydroxyl or a C1 to C4 alkoxy group and $R_3$ and $R_4$ are individually H or $R_1$C(O); and (iii) acetylated saccharides selected from the group consisting of acetylated monosaccharides, acetylated disaccharides, and acetylated polysaccharides;

(2) a source of peroxygen; and (3) an enzyme catalyst having perhydrolysis activity, wherein said enzyme catalyst comprises an enzyme having a signature motif that aligns with a reference sequence SEQ ID NO:2 using CLUSTALW, said signature motif comprising:

(i) an RGQ motif at amino acid positions 118-120 of SEQ ID NO:2;

(ii) a GXSQG motif at amino acid positions 179-183 of SEQ ID NO:2; and (iii) an HE motif at amino acid positions 298-299 of SEQ ID NO:2;

wherein said enzyme also has at least 95% amino acid identity to SEQ ID NO:4; and (b) at least one peroxycarboxylic acid formed upon combining the set of reaction components of (a).

21. The composition of claim 20 wherein the enzyme catalyst comprises an enzyme having amino acid sequence SEQ ID NO:4.

22. A kit comprising:

(a) a first compartment comprising (1) an enzyme catalyst comprising an enzyme having at least 95% amino acid identity to SEQ ID NO: 4;

(2) at least one substrate selected from the group consisting of:

(i) esters having the structure $[X]_m R_5$ wherein

X=an ester group of the formula $R_5$—C(O)O;

$R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;

$R_5$=a C1 to C6 linear, branched, or cyclic hydrocarbyl moiety optionally substituted with hydroxyl groups; wherein each carbon atom in $R_5$ individually comprises no more than one hydroxyl group or no more than one ester group;

wherein $R_5$ optionally comprises one or more ether linkages;

m=1 to the number of carbon atoms in $R_5$; and wherein said esters have solubility in water of at least 5 ppm at 25° C.;

(ii) glycerides having the structure

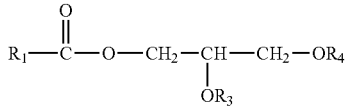

wherein $R_1$=$C_1$ to $C_7$ straight chain or branched chain alkyl optionally substituted with an hydroxyl or a C1 to C4 alkoxy group and $R_3$ and $R_4$ are individually H or $R_1$C(O); and (iii) acetylated saccharides selected from the group consisting of acetylated monosaccharides, acetylated disaccharides, and acetylated polysaccharides; and (3) an optional buffer; and (b) a second compartment comprising (1) a source of peroxygen;

(2) a peroxide stabilizer; and (3) an optional buffer.

* * * * *

SEQUENCE LISTING

<160> NUMBER OF SEQ ID NOS: 41

<210> SEQ ID NO 1
<211> LENGTH: 957
<212> TYPE: DNA
<213> ORGANISM: Bacillus subtilis

<400> SEQUENCE: 1

```
atgcaactat tcgatctgcc gctcgaccaa ttgcaaacat ataagcctga aaaaacagca      60
ccgaaagatt tttctgagtt ttggaaattg tctttggagg aacttgcaaa agtccaagca     120
gaacctgatc tacagccggt tgactatcct gctgacggag taaaagtgta ccgtctcaca     180
tataaaagct tcggaaacgc ccgcattacc ggatggtacg cggtgcctga caagcaaggc     240
ccgcatccgg cgatcgtgaa atatcatggc tacaatgcaa gctatgatgg tgagattcat     300
gaaatggtaa actgggcact ccatggctac gccgcattcg gcatgcttgt ccgcggccag     360
cagagcagcg aggatacgag tatttcactg cacggtcatg ctttgggctg gatgacgaaa     420
ggaattcttg ataaagatac atactattac cgcggtgttt atttggacgc cgtccgcgcg     480
cttgaggtca tcagcagctt cgacgaggtt gacgaaacaa ggatcggtgt gacaggagga     540
agccaaggcg gaggtttaac cattgccgca gcagcgctgt cagacattcc aaaagccgcg     600
gttgccgatt atccttattt aagcaacttc gaacgggcca ttgatgtggc gcttgaacag     660
ccgtaccttg aaatcaattc cttcttcaga agaaatggca gcccggaaac agaagtgcag     720
gcgatgaaga cactttcata tttcgatatt atgaatctcg ctgaccgagt gaaggtgcct     780
gtcctgatgt caatcggcct gattgacaag gtcacgccgc cgtccaccgt gtttgccgcc     840
tacaatcatt tggaaacaga gaaagagctg aaggtgtacc gctacttcgg acatgagtat     900
atccctgctt ttcaaacgga aaaacttgct ttctttaagc agcatcttaa aggctga      957
```

<210> SEQ ID NO 2
<211> LENGTH: 318
<212> TYPE: PRT
<213> ORGANISM: Bacillus subtilis

<400> SEQUENCE: 2

```
Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Gln Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Ser Ser Glu Asp Thr Ser Ile
        115                 120                 125

Ser Leu His Gly His Ala Leu Gly Trp Met Thr Lys Gly Ile Leu Asp
    130                 135                 140

Lys Asp Thr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
    195                 200                 205

Asn Phe Glu Arg Ala Ile Asp Val Ala Leu Glu Gln Pro Tyr Leu Glu
210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
    275                 280                 285

Glu Leu Lys Val Tyr Arg Tyr Phe Gly His Glu Tyr Ile Pro Ala Phe
290                 295                 300

Gln Thr Glu Lys Leu Ala Phe Phe Lys Gln His Leu Lys Gly
305                 310                 315

<210> SEQ ID NO 3
<211> LENGTH: 939
<212> TYPE: DNA
<213> ORGANISM: Lactococcus lactis

<400> SEQUENCE: 3
atgacaaaaa taacaattg gcaagattat caaggaagtt cacttaaacc agaggatttt     60
gataaatttt gggatgaaaa aattaatttg gtttcaaatc atcaatttga atttgaatta    120
atagaaaaaa tcttttcctc taaggtagtt aactttttatc atttgtggtt tacagctatt    180
gatggagcta aaattcatgc tcagttaatt gttcccaaga atttgaaaga gaaatacca     240 gccatcttac aatttcatgg ttatcattgc gatagtgggg attgggtcga taaaataggg    300
atagttgccg aagggaatgt agttcttgcg cttgattgtc gaggacaagg tggtttaagt    360
```

```
caagataata ttcaaactat ggggatgaca atgaagggac tcattgttcg aggaattgat    420
gaagggtatg aaaatctcta ttacgttcgc caatttatgg acttaataac tgcaaccaaa    480
attttatccg agtttgattt tgttgatgaa acaaatataa gtgcacaagg tgcttctcaa    540
ggtggagcgc ttgccgttgc ttgcgccgca ctttctcctc ttataaaaaa ggtgactgcc    600
acttacccct ttctttcaga ttatcgcaaa gcttatgagc ttggtgccga ggaatctgct    660
ttcgaagaac ttccatattg gtttcagttt aaagatccac ttcatctaag agaagactgg    720
ttttttaatc agttggaata cattgatatt caaaatttag caccaagaat taaggctgag    780
gtcatttgga tcctaggcgg caaagatact gttgttcctc cgattacgca aatggcggct    840
tacaataaaa tacaaagtaa aaaatctctc tatgtcttac ctgaatacgg ccatgaatat    900
cttcctaaaa ttagcgactg gttaagagag aatcaataa                           939

<210> SEQ ID NO 4
<211> LENGTH: 312
<212> TYPE: PRT
<213> ORGANISM: Lactococcus lactis

<400> SEQUENCE: 4

Met Thr Lys Ile Asn Asn Trp Gln Asp Tyr Gln Gly Ser Ser Leu Lys
1               5                   10                  15

Pro Glu Asp Phe Asp Lys Phe Trp Asp Glu Lys Ile Asn Leu Val Ser
                20                  25                  30

Asn His Gln Phe Glu Phe Glu Leu Ile Glu Lys Asn Leu Ser Ser Lys
            35                  40                  45

Val Val Asn Phe Tyr His Leu Trp Phe Thr Ala Ile Asp Gly Ala Lys
        50                  55                  60

Ile His Ala Gln Leu Ile Val Pro Lys Asn Leu Lys Glu Lys Tyr Pro
65                  70                  75                  80

Ala Ile Leu Gln Phe His Gly Tyr His Cys Asp Ser Gly Asp Trp Val
                85                  90                  95

Asp Lys Ile Gly Ile Val Ala Glu Gly Asn Val Val Leu Ala Leu Asp
            100                 105                 110

Cys Arg Gly Gln Gly Gly Leu Ser Gln Asp Asn Ile Gln Thr Met Gly
        115                 120                 125

Met Thr Met Lys Gly Leu Ile Val Arg Gly Ile Asp Glu Gly Tyr Glu
130                 135                 140

Asn Leu Tyr Tyr Val Arg Gln Phe Met Asp Leu Ile Thr Ala Thr Lys
145                 150                 155                 160

Ile Leu Ser Glu Phe Asp Phe Val Asp Glu Thr Asn Ile Ser Ala Gln
                165                 170                 175

Gly Ala Ser Gln Gly Gly Ala Leu Ala Val Ala Cys Ala Ala Leu Ser
            180                 185                 190

Pro Leu Ile Lys Lys Val Thr Ala Thr Tyr Pro Phe Leu Ser Asp Tyr
        195                 200                 205

Arg Lys Ala Tyr Glu Leu Gly Ala Glu Glu Ser Ala Phe Glu Glu Leu
210                 215                 220

Pro Tyr Trp Phe Gln Phe Lys Asp Pro Leu His Leu Arg Glu Asp Trp
225                 230                 235                 240

Phe Phe Asn Gln Leu Glu Tyr Ile Asp Ile Gln Asn Leu Ala Pro Arg
                245                 250                 255

Ile Lys Ala Glu Val Ile Trp Ile Leu Gly Gly Lys Asp Thr Val Val
            260                 265                 270

Pro Pro Ile Thr Gln Met Ala Ala Tyr Asn Lys Ile Gln Ser Lys Lys
```

```
                            275                 280                 285
Ser Leu Tyr Val Leu Pro Glu Tyr Gly His Glu Tyr Leu Pro Lys Ile
    290                 295                 300

Ser Asp Trp Leu Arg Glu Asn Gln
305                 310

<210> SEQ ID NO 5
<211> LENGTH: 972
<212> TYPE: DNA
<213> ORGANISM: Mesorhizobium loti

<400> SEQUENCE: 5
atgccgttcc cggatctgat ccagcccgaa ctgggcgctt atgtcagcag tgtcggcatg      60
ccggacgact tgcccaatt ctggacgtcg accatcgccg aggctcgcca ggccggcggt      120
gaggtcagta tcgtgcaggc gcagacgaca ctgaaggcgg tccagtcctt cgatgtcacg      180
tttccaggat acggcggtca tccaatcaaa ggatggctga tcttgccgac gcaccacaag      240
gggcggcttc ccctcgtcgt gcagtatatc ggctatggcg gcggccgcgg cttggcgcat      300
gagcaactgc attgggcggc gtcaggcttt gcctatttcc gaatggatac acgcgggcag      360
ggaagcgact ggagcgtcgg tgagaccgcc gatcccgtcg gctcgacctc gtccattccc      420
ggctttatga cgcgtggcgt gctggacaag aatgactact attaccggcg cctgttcacc      480
gatgccgtga gggcgataga tgctctgctc ggactggact tcgtcgatcc cgaacgcatc      540
gcggtttgcg gtgacagtca gggaggcggt atttcgctcg ccgttggcgg catcgacccg      600
cgcgtcaagg ccgtaatgcc cgacgttcca tttctgtgcg actttccgcg cgctgtgcag      660
actgccgtgc gcgatcccta tttggaaatc gttcgctttc tggcccagca tcgcgaaaag      720
aaggcggcag tctttgaaac gctcaactat ttcgactgcg tcaacttcgc ccggcggtcc      780
aaggcgccgg cgctgttttc ggtggccctg atggacgaag tctgcccgcc ctctaccgtg      840
tatggcgcat tcaatgccta tgcaggcgaa aagaccatca cagagtacga attcaacaat      900
catgaaggcg ggcaaggcta tcaagagcgc aacagatga cgtggctcag caggctgttc      960
ggtgtcggct ga                                                         972

<210> SEQ ID NO 6
<211> LENGTH: 323
<212> TYPE: PRT
<213> ORGANISM: Mesorhizobium loit

<400> SEQUENCE: 6

Met Pro Phe Pro Asp Leu Ile Gln Pro Glu Leu Gly Ala Tyr Val Ser
1               5                   10                  15

Ser Val Gly Met Pro Asp Asp Phe Ala Gln Phe Trp Thr Ser Thr Ile
            20                  25                  30

Ala Glu Ala Arg Gln Ala Gly Gly Glu Val Ser Ile Val Gln Ala Gln
        35                  40                  45

Thr Thr Leu Lys Ala Val Gln Ser Phe Asp Val Thr Phe Pro Gly Tyr
    50                  55                  60

Gly Gly His Pro Ile Lys Gly Trp Leu Ile Leu Pro Thr His His Lys
65                  70                  75                  80

Gly Arg Leu Pro Leu Val Val Gln Tyr Ile Gly Tyr Gly Gly Gly Arg
                85                  90                  95

Gly Leu Ala His Glu Gln Leu His Trp Ala Ala Ser Gly Phe Ala Tyr
            100                 105                 110

Phe Arg Met Asp Thr Arg Gly Gln Gly Ser Asp Trp Ser Val Gly Glu
```

```
                115                 120                 125
Thr Ala Asp Pro Val Gly Ser Thr Ser Ser Ile Pro Gly Phe Met Thr
130                 135                 140

Arg Gly Val Leu Asp Lys Asn Asp Tyr Tyr Arg Arg Leu Phe Thr
145                 150                 155                 160

Asp Ala Val Arg Ala Ile Asp Ala Leu Leu Gly Leu Asp Phe Val Asp
                165                 170                 175

Pro Glu Arg Ile Ala Val Cys Gly Asp Ser Gln Gly Gly Ile Ser
                180                 185                 190

Leu Ala Val Gly Gly Ile Asp Pro Arg Val Lys Ala Val Met Pro Asp
                195                 200                 205

Val Pro Phe Leu Cys Asp Phe Pro Arg Ala Val Gln Thr Ala Val Arg
    210                 215                 220

Asp Pro Tyr Leu Glu Ile Val Arg Phe Leu Ala Gln His Arg Glu Lys
225                 230                 235                 240

Lys Ala Ala Val Phe Glu Thr Leu Asn Tyr Phe Asp Cys Val Asn Phe
                245                 250                 255

Ala Arg Arg Ser Lys Ala Pro Ala Leu Phe Ser Val Ala Leu Met Asp
                260                 265                 270

Glu Val Cys Pro Pro Ser Thr Val Tyr Gly Ala Phe Asn Ala Tyr Ala
                275                 280                 285

Gly Glu Lys Thr Ile Thr Glu Tyr Glu Phe Asn Asn His Glu Gly Gly
                290                 295                 300

Gln Gly Tyr Gln Glu Arg Gln Gln Met Thr Trp Leu Ser Arg Leu Phe
305                 310                 315                 320

Gly Val Gly
```

<210> SEQ ID NO 7
<211> LENGTH: 990
<212> TYPE: DNA
<213> ORGANISM: Geobacillus stearothermophilus

<400> SEQUENCE: 7

```
atgttcgata tgccgttagc acaattacag aaatacatgg ggacaaatcc gaagccggct    60
gattttgctg acttttggag tcgagcgttg gaggaattat ctgcccaatc gttgcattat   120
gagctgattc cggcaacatt tcaaacgaca gtggcgagtt gctaccattt gtatttcacg   180
ggagtcggcg ggctagagt ccattgtcag ttagtaaaac cgagagagca gaagcagaaa   240
gccccggggt tggtatggtt tcatggctac catacgaata gcggcgattg ggtcgataaa   300
ctggcatatg ctgcggcagg ttttactgta ttggcgatgg attgccgcgg ccaaggagga   360
aaatcagagg ataatttgca agtgaaaggc ccaacattga aggccatat tattcgcgga   420
attgaggatc caaatcctca tcatctttat tatcgaaatg ttttttttaga tacagttcag   480
gcggtaagaa tttatgctc tatggatcat attgatcgtg aacgaattgg tgtatatggc   540
gcttcccaag gaggagcgtt ggcattagcg tgtgctgctc tggaaccatc ggtggtgaaa   600
aaagcggttg tgctctatcc attttatcg gattataagc gggcgcaaga gttggatatg   660
aaaaatacccg cgtatgagga aattcattat tattttcgat ttttagatcc cacacatgag   720
cgggaagaag aagtatttta caaactaggc tatattgata ttcaactctt agccgatcgg   780
atttgtgccg atgttttatg ggctgttgcg ctagaagacc atatttgtcc cccgtccaca   840
caatttgctg tttataataa aattaagtca aaaaaagaca tggttttgtt ttacgagtat   900
ggtcatgagt atttaccgac tatgggagac cgtgcttatc tgttttttttg cccgatcttc   960
```
tttccaatcc aaaagagaaa cgttaagtaa                                             990

<210> SEQ ID NO 8
<211> LENGTH: 329
<212> TYPE: PRT
<213> ORGANISM: Geobacillus stearothermophilus

<400> SEQUENCE: 8

```
Met Phe Asp Met Pro Leu Ala Gln Leu Gln Lys Tyr Met Gly Thr Asn
1               5                   10                  15

Pro Lys Pro Ala Asp Phe Ala Asp Phe Trp Ser Arg Ala Leu Glu Glu
            20                  25                  30

Leu Ser Ala Gln Ser Leu His Tyr Glu Leu Ile Pro Ala Thr Phe Gln
        35                  40                  45

Thr Thr Val Ala Ser Cys Tyr His Leu Tyr Phe Thr Gly Val Gly Gly
    50                  55                  60

Ala Arg Val His Cys Gln Leu Val Lys Pro Arg Glu Gln Lys Gln Lys
65                  70                  75                  80

Gly Pro Gly Leu Val Trp Phe His Gly Tyr His Thr Asn Ser Gly Asp
                85                  90                  95

Trp Val Asp Lys Leu Ala Tyr Ala Ala Ala Gly Phe Thr Val Leu Ala
            100                 105                 110

Met Asp Cys Arg Gly Gln Gly Gly Lys Ser Glu Asp Asn Leu Gln Val
        115                 120                 125

Lys Gly Pro Thr Leu Lys Gly His Ile Ile Arg Gly Ile Glu Asp Pro
    130                 135                 140

Asn Pro His His Leu Tyr Tyr Arg Asn Val Phe Leu Asp Thr Val Gln
145                 150                 155                 160

Ala Val Arg Ile Leu Cys Ser Met Asp His Ile Asp Arg Glu Arg Ile
                165                 170                 175

Gly Val Tyr Gly Ala Ser Gln Gly Gly Ala Leu Ala Leu Ala Cys Ala
            180                 185                 190

Ala Leu Glu Pro Ser Val Val Lys Lys Ala Val Val Leu Tyr Pro Phe
        195                 200                 205

Leu Ser Asp Tyr Lys Arg Ala Gln Glu Leu Asp Met Lys Asn Thr Ala
    210                 215                 220

Tyr Glu Glu Ile His Tyr Tyr Phe Arg Phe Leu Asp Pro Thr His Glu
225                 230                 235                 240

Arg Glu Glu Glu Val Phe Tyr Lys Leu Gly Tyr Ile Asp Ile Gln Leu
                245                 250                 255

Leu Ala Asp Arg Ile Cys Ala Asp Val Leu Trp Ala Val Ala Leu Glu
            260                 265                 270

Asp His Ile Cys Pro Pro Ser Thr Gln Phe Ala Val Tyr Asn Lys Ile
        275                 280                 285

Lys Ser Lys Lys Asp Met Val Leu Phe Tyr Glu Tyr Gly His Glu Tyr
    290                 295                 300

Leu Pro Thr Met Gly Asp Arg Ala Tyr Leu Phe Phe Cys Pro Ile Phe
305                 310                 315                 320

Phe Pro Ile Gln Lys Arg Asn Val Lys
                325
```

<210> SEQ ID NO 9
<211> LENGTH: 795
<212> TYPE: DNA
<213> ORGANISM: artificial sequence
<220> FEATURE:
<223> OTHER INFORMATION: synthetic construct -continued

<400> SEQUENCE: 9

```
atgattgaac aagatggatt gcacgcaggt tctccggccg cttgggtgga gaggctattc      60
ggctatgact gggcacaaca gacaatcggc tgctctgatg ccgccgtgtt ccggctgtca     120
gcgcagggc gcccggttct ttttgtcaag accgacctgt ccggtgccct gaatgaactg     180
caggacgagg cagcgcggct atcgtggctg gccacgacgg gcgttccttg cgcagctgtg     240
ctcgacgttg tcactgaagc gggaagggac tggctgctat tgggcgaagt gccggggcag     300
gatctcctgt catctcacct tgctcctgcc gagaaagtat ccatcatggc tgatgcaatg     360
cggcggctgc atacgcttga tccggctacc tgcccattcg accaccaagc gaaacatcgc     420
atcgagcgag cacgtactcg gatggaagcc ggtcttgtcg atcaggatga tctggacgaa     480
gagcatcagg ggctcgcgcc agccgaactg ttcgccaggc tcaaggcgcg catgcccgac     540
ggcgaggatc tcgtcgtgac ccatggcgat gcctgcttgc cgaatatcat ggtggaaaat     600
ggccgctttt ctggattcat cgactgtggc cggctgggtg tggcggaccg ctatcaggac     660
atagcgttgg ctacccgtga tattgctgaa gagcttggcg gcgaatgggc tgaccgcttc     720
ctcgtgcttt acggtatcgc cgctcccgat tcgcagcgca tcgccttcta tcgccttctt     780
gacgagttct tctaa                                                     795
```

<210> SEQ ID NO 10
<211> LENGTH: 3434
<212> TYPE: DNA
<213> ORGANISM: artificial sequence
<220> FEATURE:
<223> OTHER INFORMATION: Plasmid pKD13

<400> SEQUENCE: 10

```
agattgcagc attacacgtc ttgagcgatt gtgtaggctg gagctgcttc gaagttccta      60
tactttctag agaataggaa cttcggaata ggaacttcaa gatcccctta ttagaagaac     120
tcgtcaagaa ggcgatagaa ggcgatgcgc tgcgaatcgg gagcggcgat accgtaaagc     180
acgaggaagc ggtcagccca ttcgccgcca agctcttcag caatatcacg ggtagccaac     240
gctatgtcct gatagcggtc cgccacaccc agccggccac agtcgatgaa tccagaaaag     300
cggccatttt ccaccatgat attcggcaag caggcatcgc catgggtcac gacgagatcc     360
tcgccgtcgg catgcgcgc cttgagcctg gcgaacagtt cggctggcgc gagccctga     420
tgctcttcgt ccagatcatc ctgatcgaca agaccggctt ccatccgagt acgtgctcgc     480
tcgatgcgat gtttcgcttg gtggtcgaat gggcaggtag ccggatcaag cgtatgcagc     540
cgccgcattg catcagccat gatggatact ttctcggcag gagcaaggtg agatgacagg     600
agatcctgcc ccggcacttc gcccaatagc agccagtccc ttcccgcttc agtgacaacg     660
tcgagcacag ctgcgcaagg aacgcccgtc gtggccagcc acgatagccg cgctgcctcg     720
tcctgcagtt cattcagggc accggacagg tcggtcttga caaaaagaac cgggcgcccc     780
tgcgctgaca gccggaacac ggcggcatca gagcagccga ttgtctgttg tgcccagtca     840
tagccgaata gcctctccac ccaagcggcc ggagaacctg cgtgcaatcc atcttgttca     900
atcatgcgaa acgatcctca tcctgtctct tgatcagatc ttgatcccct gcgccatcag     960
atccttggcg gcaagaaagc catccagttt actttgcagg gcttcccaac cttaccagag    1020
ggcgccccag ctggcaattc cggttcgctt gctgtcccata aaaccgccca gtctagctat    1080
cgccatgtaa gcccactgca agctacctgc tttctctttg cgcttgcgtt ttcccttgtc    1140
cagatagccc agtagctgac attcatccgg ggtcagcacc gtttctgcgg actggctttc    1200
```

```
tacgtgttcc gcttccttta gcagcccttg cgccctgagt gcttgcggca gcgtgagctt    1260
caaaagcgct ctgaagttcc tatactttct agagaatagg aacttcgaac tgcaggtcga    1320
cggatccccg gaattaattc tcatgtttga cagcttatca ctgatcagtg aattaatggc    1380
gatgacgcat cctcacgata tatccgggt aggcgcaatc actttcgtct ctactccgtt    1440
acaaagcgag gctgggtatt tcccggcctt tctgttatcc gaaatccact gaaagcacag    1500
cggctggctg aggagataaa taataaacga ggggctgtat gcacaaagca tcttctgttg    1560
agttaagaac gagtatcgag atggcacata gccttgctca aattggaatc aggtttgtgc    1620
caataccagt agaaacagac gaagaagcta gctttgcact ggattgcgag gctttgccat    1680
ggctaattcc catgtcagcc gttaagtgtt cctgtgtcac tgaaaattgc tttgagaggc    1740
tctaagggct tctcagtgcg ttacatccct ggcttgttgt ccacaaccgt taaaccttaa    1800
aagctttaaa agccttatat attcttttt ttcttataaa acttaaaacc ttagaggcta    1860
tttaagttgc tgatttatat taattttatt gttcaaacat gagagcttag tacgtgaaac    1920
atgagagctt agtacgttag ccatgagagc ttagtacgtt agccatgagg gtttagttcg    1980
ttaaacatga gagcttagta cgttaaacat gagagcttag tacgtgaaac atgagagctt    2040
agtacgtact atcaacaggt tgaactgcgg atcttgcggc cgcaaaaatt aaaaatgaag    2100
ttttaaatca atctaaagta tatatgagta aacttggtct gacagttacc aatgcttaat    2160
cagtgaggca cctatctcag cgatctgtct atttcgttca tccatagttg cctgactccc    2220
cgtcgtgtag ataactacga tacgggaggg cttaccatct ggccccagtg ctgcaatgat    2280
accgcgagac ccacgctcac cggctccaga tttatcagca ataaaccagc cagccggaag    2340
ggccgagcgc agaagtggtc ctgcaacttt atccgcctcc atccagtcta ttaattgttg    2400
ccgggaagct agagtaagta gttcgccagt taatagtttg cgcaacgttg ttgccattgc    2460
tacaggcatc gtggtgtcac gctcgtcgtt tggtatggct tcattcagct ccggttccca    2520
acgatcaagg cgagttacat gatcccccat gttgtgcaaa aaagcggtta gctccttcgg    2580
tcctccgatc gttgtcagaa gtaagttggc cgcagtgtta tcactcatgg ttatggcagc    2640
actgcataat tctcttactg tcatgccatc cgtaagatgc ttttctgtga ctggtgagta    2700
ctcaaccaag tcattctgag aatagtgtat gcggcgaccg agttgctctt gcccggcgtc    2760
aatacgggat aataccgcgc cacatagcag aactttaaaa gtgctcatca ttggaaaacg    2820
ttcttcgggg cgaaaactct caaggatctt accgctgttg agatccagtt cgatgtaacc    2880
cactcgtgca cccaactgat cttcagcatc ttttactttc accagcgttt ctgggtgagc    2940
aaaaacagga aggcaaaatg ccgcaaaaaa gggaataagg gcgacacgga aatgttgaat    3000
actcatactc ttcctttttc aatattattg aagcatttat cagggttatt gtctcatgag    3060
cggatacata tttgaatgta tttagaaaaa taaacaaata ggggttccgc gcacatttcc    3120
ccgaaaagtg ccacctgcat cgatggcccc ccgatggtag tgtggggtct ccccatgcga    3180
gagtagggaa ctgccaggca tcaaataaaa cgaaaggctc agtcgaaaga ctgggccttt    3240
cgttttatct gttgtttgtc ggtgaacgct ctcctgagta ggacaaatcc gccgggagcg    3300
gatttgaacg ttgcgaagca acggcccgga gggtggcggg caggacgccc gccataaact    3360
gccaggcatc aaattaagca gaaggccatc ctgacggatg cctttttgc gtggccagtg    3420 ccaagcttgc atgc                                                      3434

<210> SEQ ID NO 11
<211> LENGTH: 80
```

```
<212> TYPE: DNA
<213> ORGANISM: artificial sequence
<220> FEATURE:
<223> OTHER INFORMATION: Primer

<400> SEQUENCE: 11
atgagcacgt cagacgatat ccataacacc acagccactg gcaaatgccc gttccatcag    60
gtgtaggctg gagctgcttc                                                80

<210> SEQ ID NO 12
<211> LENGTH: 82
<212> TYPE: DNA
<213> ORGANISM: artificial sequence
<220> FEATURE:
<223> OTHER INFORMATION: Primer

<400> SEQUENCE: 12
taacagcagg tcgaaacggt cgaggttcat cactttcacc catgccgcca cgaagtcttt    60
attccgggga tccgtcgacc tg                                             82

<210> SEQ ID NO 13
<211> LENGTH: 1424
<212> TYPE: DNA
<213> ORGANISM: artificial sequence
<220> FEATURE:
<223> OTHER INFORMATION: Synthetic construct

<400> SEQUENCE: 13
taacagcagg tcgaaacggt cgaggttcat cactttcacc catgccgcca cgaagtcttt    60
attccgggga tccgtcgacc tgcagttcga agttcctatt ctctagaaag tataggaact   120
tcagagcgct tttgaagctc acgctgccgc aagcactcag ggcgcaaggg ctgctaaagg   180
aagcggaaca cgtagaaagc cagtccgcag aaacggtgct gaccccggat gaatgtcagc   240
tactgggcta tctggacaag ggaaaacgca agcgcaaaga gaaagcaggt agcttgcagt   300
gggcttacat ggcgatagct agactgggcg gttttatgga cagcaagcga accggaattg   360
ccagctgggg cgccctctgg taaggttggg aagccctgca agtaaactg gatggctttc     420 ttgccgccaa ggatctgatg gcgcagggga tcaagatctg atcaagagac aggatgagga   480
tcgtttcgca tgattgaaca agatggattg cacgcaggtt ctccggccgc ttgggtggag   540
aggctattcg gctatgactg gcacaacag acaatcggct gctctgatgc cgccgtgttc    600
cggctgtcag cgcaggggcg cccggttctt tttgtcaaga ccgacctgtc cggtgccctg   660
aatgaactgc aggacgaggc agcgcggcta tcgtggctgg ccacgacggg cgttccttgc   720
gcagctgtgc tcgacgttgt cactgaagcg ggaagggact ggctgctatt gggcgaagtg   780
ccggggcagg atctcctgtc atctcacctt gctcctgccg agaaagtatc catcatggct   840
gatgcaatgc ggcggctgca tacgcttgat ccggctacct gcccattcga ccaccaagcg   900
aaacatcgca tcgagcgagc acgtactcgg atggaagccg gtcttgtcga tcaggatgat   960
ctggacgaag agcatcaggg gctcgcgcca gccgaactgt cgccaggct caaggcgcgc   1020 atgcccgacg gcgaggatct cgtcgtgacc catggcgatg cctgcttgcc gaatatcatg  1080
gtggaaaatg gccgcttttc tggattcatc gactgtggcc ggctgggtgt ggcggaccgc  1140
tatcaggaca tagcgttggc tacccgtgat attgctgaag agcttggcgg cgaatgggct  1200
gaccgcttcc tcgtgcttta cggtatcgcc gctcccgatt cgcagcgcat cgccttctat  1260
cgccttcttg acgagttctt ctaataaggg gatcttgaag ttcctattcc gaagttccta  1320
ttctctagaa agtataggaa cttcgaagca gctccagcct acacctgatg aacgggcat   1380
```
ttgccagtgg ctgtggtgtt atggatatcg tctgacgtgc tcat        1424

<210> SEQ ID NO 14
<211> LENGTH: 2181
<212> TYPE: DNA
<213> ORGANISM: Escherichia coli
<220> FEATURE:
<221> NAME/KEY: CDS
<222> LOCATION: (1)..(2181)

<400> SEQUENCE: 14

| | | | | | | | | | | | | | | | | |
|---|---|---|---|---|---|---|---|---|---|---|---|---|---|---|---|---|
| atg | agc | acg | tca | gac | gat | atc | cat | aac | acc | aca | gcc | act | ggc | aaa | tgc | 48 |
| Met | Ser | Thr | Ser | Asp | Asp | Ile | His | Asn | Thr | Thr | Ala | Thr | Gly | Lys | Cys | |
| 1 | | | | 5 | | | | | 10 | | | | | 15 | | |
| ccg | ttc | cat | cag | ggc | ggt | cac | gac | cag | agt | gcg | ggg | gcg | ggc | aca | acc | 96 |
| Pro | Phe | His | Gln | Gly | Gly | His | Asp | Gln | Ser | Ala | Gly | Ala | Gly | Thr | Thr | |
| | | | 20 | | | | | 25 | | | | | 30 | | | |
| act | cgc | gac | tgg | tgg | cca | aat | caa | ctt | cgt | gtt | gac | ctg | tta | aac | caa | 144 |
| Thr | Arg | Asp | Trp | Trp | Pro | Asn | Gln | Leu | Arg | Val | Asp | Leu | Leu | Asn | Gln | |
| | | 35 | | | | | 40 | | | | | 45 | | | | |
| cat | tct | aat | cgt | tct | aac | cca | ctg | ggt | gag | gac | ttt | gac | tac | cgc | aaa | 192 |
| His | Ser | Asn | Arg | Ser | Asn | Pro | Leu | Gly | Glu | Asp | Phe | Asp | Tyr | Arg | Lys | |
| | 50 | | | | | 55 | | | | | 60 | | | | | |
| gaa | ttc | agc | aaa | tta | gat | tac | tac | ggc | ctg | aaa | aaa | gat | ctg | aaa | gcc | 240 |
| Glu | Phe | Ser | Lys | Leu | Asp | Tyr | Tyr | Gly | Leu | Lys | Lys | Asp | Leu | Lys | Ala | |
| 65 | | | | | 70 | | | | | 75 | | | | | 80 | |
| ctg | ttg | aca | gaa | tct | caa | ccg | tgg | tgg | cca | gcc | gac | tgg | ggc | agt | tac | 288 |
| Leu | Leu | Thr | Glu | Ser | Gln | Pro | Trp | Trp | Pro | Ala | Asp | Trp | Gly | Ser | Tyr | |
| | | | | 85 | | | | | 90 | | | | | 95 | | |
| gcc | ggt | ctg | ttt | att | cgt | atg | gcc | tgg | cac | ggc | gcg | ggg | act | tac | cgt | 336 |
| Ala | Gly | Leu | Phe | Ile | Arg | Met | Ala | Trp | His | Gly | Ala | Gly | Thr | Tyr | Arg | |
| | | | 100 | | | | | 105 | | | | | 110 | | | |
| tca | atc | gat | gga | cgc | ggt | ggc | gcg | ggt | cgt | ggt | cag | caa | cgt | ttt | gca | 384 |
| Ser | Ile | Asp | Gly | Arg | Gly | Gly | Ala | Gly | Arg | Gly | Gln | Gln | Arg | Phe | Ala | |
| | | 115 | | | | | 120 | | | | | 125 | | | | |
| ccg | ctg | aac | tcc | tgg | ccg | gat | aac | gta | agc | ctc | gat | aaa | gcg | cgt | cgc | 432 |
| Pro | Leu | Asn | Ser | Trp | Pro | Asp | Asn | Val | Ser | Leu | Asp | Lys | Ala | Arg | Arg | |
| | 130 | | | | | 135 | | | | | 140 | | | | | |
| ctg | ttg | tgg | cca | atc | aaa | cag | aaa | tat | ggt | cag | aaa | atc | tcc | tgg | gcc | 480 |
| Leu | Leu | Trp | Pro | Ile | Lys | Gln | Lys | Tyr | Gly | Gln | Lys | Ile | Ser | Trp | Ala | |
| 145 | | | | | 150 | | | | | 155 | | | | | 160 | |
| gac | ctg | ttt | atc | ctc | gcg | ggt | aac | gtg | gcg | cta | gaa | aac | tcc | ggc | ttc | 528 |
| Asp | Leu | Phe | Ile | Leu | Ala | Gly | Asn | Val | Ala | Leu | Glu | Asn | Ser | Gly | Phe | |
| | | | | 165 | | | | | 170 | | | | | 175 | | |
| cgt | acc | ttc | ggt | ttt | ggt | gcc | ggt | cgt | gaa | gac | gtc | tgg | gaa | ccg | gat | 576 |
| Arg | Thr | Phe | Gly | Phe | Gly | Ala | Gly | Arg | Glu | Asp | Val | Trp | Glu | Pro | Asp | |
| | | | 180 | | | | | 185 | | | | | 190 | | | |
| ctg | gat | gtt | aac | tgg | ggt | gat | gaa | aaa | gcc | tgg | ctg | act | cac | cgt | cat | 624 |
| Leu | Asp | Val | Asn | Trp | Gly | Asp | Glu | Lys | Ala | Trp | Leu | Thr | His | Arg | His | |
| | | 195 | | | | | 200 | | | | | 205 | | | | |
| ccg | gaa | gcg | ctg | gcg | aaa | gca | ccg | ctg | ggt | gca | acc | gag | atg | ggt | ctg | 672 |
| Pro | Glu | Ala | Leu | Ala | Lys | Ala | Pro | Leu | Gly | Ala | Thr | Glu | Met | Gly | Leu | |
| | 210 | | | | | 215 | | | | | 220 | | | | | |
| att | tac | gtt | aac | ccg | gaa | ggc | ccg | gat | cac | agc | ggc | gaa | ccg | ctt | tct | 720 |
| Ile | Tyr | Val | Asn | Pro | Glu | Gly | Pro | Asp | His | Ser | Gly | Glu | Pro | Leu | Ser | |
| 225 | | | | | 230 | | | | | 235 | | | | | 240 | |
| gcg | gca | gca | gct | atc | cgc | gcg | acc | ttc | ggc | aac | atg | ggc | atg | aac | gac | 768 |
| Ala | Ala | Ala | Ala | Ile | Arg | Ala | Thr | Phe | Gly | Asn | Met | Gly | Met | Asn | Asp | |
| | | | | 245 | | | | | 250 | | | | | 255 | | |
| gaa | gaa | acc | gtg | gcg | ctg | att | gcg | ggt | ggt | cat | acg | ctg | ggt | aaa | acc | 816 |
| Glu | Glu | Thr | Val | Ala | Leu | Ile | Ala | Gly | Gly | His | Thr | Leu | Gly | Lys | Thr | |

-continued

```
                    260                 265                 270
cac ggt gcc ggt ccg aca tca aat gta ggt cct gat cca gaa gct gca    864
His Gly Ala Gly Pro Thr Ser Asn Val Gly Pro Asp Pro Glu Ala Ala
        275                 280                 285 ccg att gaa gaa caa ggt tta ggt tgg gcg agc act tac ggc agc ggc    912
Pro Ile Glu Glu Gln Gly Leu Gly Trp Ala Ser Thr Tyr Gly Ser Gly
    290                 295                 300 gtt ggc gca gat gcc att acc tct ggt ctg gaa gta gtc tgg acc cag    960
Val Gly Ala Asp Ala Ile Thr Ser Gly Leu Glu Val Val Trp Thr Gln
305                 310                 315                 320 acg ccg acc cag tgg agc aac tat ttc ttc gag aac ctg ttc aag tat   1008
Thr Pro Thr Gln Trp Ser Asn Tyr Phe Phe Glu Asn Leu Phe Lys Tyr
                325                 330                 335 gag tgg gta cag acc cgc agc ccg gct ggc gca atc cag ttc gaa gcg   1056
Glu Trp Val Gln Thr Arg Ser Pro Ala Gly Ala Ile Gln Phe Glu Ala
            340                 345                 350 gta gac gca ccg gaa att atc ccg gat ccg ttt gat ccg tcg aag aaa   1104
Val Asp Ala Pro Glu Ile Ile Pro Asp Pro Phe Asp Pro Ser Lys Lys
        355                 360                 365 cgt aaa ccg aca atg ctg gtg acc gac ctg acg ctg cgt ttt gat cct   1152
Arg Lys Pro Thr Met Leu Val Thr Asp Leu Thr Leu Arg Phe Asp Pro
370                 375                 380 gag ttc gag aag atc tct cgt cgt ttc ctc aac gat ccg cag gcg ttc   1200
Glu Phe Glu Lys Ile Ser Arg Arg Phe Leu Asn Asp Pro Gln Ala Phe
385                 390                 395                 400 aac gaa gcc ttt gcc cgt gcc tgg ttc aaa ctg acg cac agg gat atg   1248
Asn Glu Ala Phe Ala Arg Ala Trp Phe Lys Leu Thr His Arg Asp Met
                405                 410                 415 ggg ccg aaa tct cgc tac atc ggg ccg gaa gtg ccg aaa gaa gat ctg   1296
Gly Pro Lys Ser Arg Tyr Ile Gly Pro Glu Val Pro Lys Glu Asp Leu
            420                 425                 430 atc tgg caa gat ccg ctg ccg cag ccg atc tac aac ccg acc gag cag   1344
Ile Trp Gln Asp Pro Leu Pro Gln Pro Ile Tyr Asn Pro Thr Glu Gln
        435                 440                 445 gac att atc gat ctg aaa ttc gcg att gcg gat tct ggt ctg tct gtt   1392
Asp Ile Ile Asp Leu Lys Phe Ala Ile Ala Asp Ser Gly Leu Ser Val
450                 455                 460 agt gag ctg gta tcg gtg gcc tgg gca tct gct tct acc ttc cgt ggt   1440
Ser Glu Leu Val Ser Val Ala Trp Ala Ser Ala Ser Thr Phe Arg Gly
465                 470                 475                 480 ggc gac aaa cgc ggt ggt gcc aac ggt gcg cgt ctg gca tta atg ccg   1488
Gly Asp Lys Arg Gly Gly Ala Asn Gly Ala Arg Leu Ala Leu Met Pro
                485                 490                 495 cag cgc gac tgg gat gtg aac gcc gca gcc gtt cgt gct ctg cct gtt   1536
Gln Arg Asp Trp Asp Val Asn Ala Ala Ala Val Arg Ala Leu Pro Val
            500                 505                 510 ctg gag aaa atc cag aaa gag tct ggt aaa gcc tcg ctg gcg gat atc   1584
Leu Glu Lys Ile Gln Lys Glu Ser Gly Lys Ala Ser Leu Ala Asp Ile
        515                 520                 525 ata gtg ctg gct ggt gtg gtt ggt gtt gag aaa gcc gca agc gcc gca   1632
Ile Val Leu Ala Gly Val Val Gly Val Glu Lys Ala Ala Ser Ala Ala
530                 535                 540 ggt ttg agc att cat gta ccg ttt gcg ccg ggt cgc gtt gat gcg cgt   1680
Gly Leu Ser Ile His Val Pro Phe Ala Pro Gly Arg Val Asp Ala Arg
545                 550                 555                 560 cag gat cag act gac att gag atg ttt gag ctg ctg gag cca att gct   1728
Gln Asp Gln Thr Asp Ile Glu Met Phe Glu Leu Leu Glu Pro Ile Ala
                565                 570                 575 gac ggt ttc cgt aac tat cgc gct cgt ctg gac gtt tcc acc acc gag   1776
Asp Gly Phe Arg Asn Tyr Arg Ala Arg Leu Asp Val Ser Thr Thr Glu
```

```
                      580                   585                     590
tca ctg ctg atc gac aaa gca cag caa ctg acg ctg acc gcg ccg gaa    1824
Ser Leu Leu Ile Asp Lys Ala Gln Gln Leu Thr Leu Thr Ala Pro Glu
        595                 600                 605 atg act gcg ctg gtg ggc ggc atg cgt gta ctg ggt gcc aac ttc gat    1872
Met Thr Ala Leu Val Gly Gly Met Arg Val Leu Gly Ala Asn Phe Asp
610                 615                 620 ggc agc aaa aac ggc gtc ttc act gac cgc gtt ggc gta ttg agc aat    1920
Gly Ser Lys Asn Gly Val Phe Thr Asp Arg Val Gly Val Leu Ser Asn
625                 630                 635                 640 gac ttc ttc gtg aac ttg ctg gat atg cgt tac gag tgg aaa gcg acc    1968
Asp Phe Phe Val Asn Leu Leu Asp Met Arg Tyr Glu Trp Lys Ala Thr
                645                 650                 655 gac gaa tcg aaa gag ctg ttc gaa ggc cgt gac cgt gaa acc ggc gaa    2016
Asp Glu Ser Lys Glu Leu Phe Glu Gly Arg Asp Arg Glu Thr Gly Glu
            660                 665                 670 gtg aaa ttt acg gcc agc cgt gcg gat ctg gtg ttt ggt tct aac tcc    2064
Val Lys Phe Thr Ala Ser Arg Ala Asp Leu Val Phe Gly Ser Asn Ser
        675                 680                 685 gtc ctg cgt gcg gtg gcg gaa gtt tac gcc agt agc gat gcc cac gag    2112
Val Leu Arg Ala Val Ala Glu Val Tyr Ala Ser Ser Asp Ala His Glu
690                 695                 700 aag ttt gtt aaa gac ttc gtg gcg gca tgg gtg aaa gtg atg aac ctc    2160
Lys Phe Val Lys Asp Phe Val Ala Ala Trp Val Lys Val Met Asn Leu
705                 710                 715                 720 gac cgt ttc gac ctg ctg taa                                        2181
Asp Arg Phe Asp Leu Leu
                725

<210> SEQ ID NO 15
<211> LENGTH: 726
<212> TYPE: PRT
<213> ORGANISM: Escherichia coli

<400> SEQUENCE: 15

Met Ser Thr Ser Asp Asp Ile His Asn Thr Ala Thr Gly Lys Cys
1               5                   10                  15

Pro Phe His Gln Gly Gly His Asp Gln Ser Ala Gly Ala Gly Thr Thr
                20                  25                  30

Thr Arg Asp Trp Trp Pro Asn Gln Leu Arg Val Asp Leu Leu Asn Gln
        35                  40                  45

His Ser Asn Arg Ser Asn Pro Leu Gly Glu Asp Phe Asp Tyr Arg Lys
    50                  55                  60

Glu Phe Ser Lys Leu Asp Tyr Tyr Gly Leu Lys Lys Asp Leu Lys Ala
65                  70                  75                  80

Leu Leu Thr Glu Ser Gln Pro Trp Trp Pro Ala Asp Trp Gly Ser Tyr
                85                  90                  95

Ala Gly Leu Phe Ile Arg Met Ala Trp His Gly Ala Gly Thr Tyr Arg
            100                 105                 110

Ser Ile Asp Gly Arg Gly Gly Ala Gly Arg Gly Gln Gln Arg Phe Ala
        115                 120                 125

Pro Leu Asn Ser Trp Pro Asp Asn Val Ser Leu Asp Lys Ala Arg Arg
    130                 135                 140

Leu Leu Trp Pro Ile Lys Gln Lys Tyr Gly Gln Lys Ile Ser Trp Ala
145                 150                 155                 160

Asp Leu Phe Ile Leu Ala Gly Asn Val Ala Leu Glu Asn Ser Gly Phe
                165                 170                 175

Arg Thr Phe Gly Phe Gly Ala Gly Arg Glu Asp Val Trp Glu Pro Asp
```

```
            180                 185                 190
Leu Asp Val Asn Trp Gly Asp Glu Lys Ala Trp Leu Thr His Arg His
            195                 200                 205
Pro Glu Ala Leu Ala Lys Ala Pro Leu Gly Ala Thr Glu Met Gly Leu
            210                 215                 220
Ile Tyr Val Asn Pro Glu Gly Pro Asp His Ser Gly Glu Pro Leu Ser
225                 230                 235                 240
Ala Ala Ala Ala Ile Arg Ala Thr Phe Gly Asn Met Gly Met Asn Asp
            245                 250                 255
Glu Glu Thr Val Ala Leu Ile Ala Gly Gly His Thr Leu Gly Lys Thr
            260                 265                 270
His Gly Ala Gly Pro Thr Ser Asn Val Gly Pro Asp Pro Glu Ala Ala
            275                 280                 285
Pro Ile Glu Glu Gln Gly Leu Gly Trp Ala Ser Thr Tyr Gly Ser Gly
            290                 295                 300
Val Gly Ala Asp Ala Ile Thr Ser Gly Leu Glu Val Val Trp Thr Gln
305                 310                 315                 320
Thr Pro Thr Gln Trp Ser Asn Tyr Phe Phe Glu Asn Leu Phe Lys Tyr
            325                 330                 335
Glu Trp Val Gln Thr Arg Ser Pro Ala Gly Ala Ile Gln Phe Glu Ala
            340                 345                 350
Val Asp Ala Pro Glu Ile Ile Pro Asp Pro Phe Asp Pro Ser Lys Lys
            355                 360                 365
Arg Lys Pro Thr Met Leu Val Thr Asp Leu Thr Leu Arg Phe Asp Pro
            370                 375                 380
Glu Phe Glu Lys Ile Ser Arg Arg Phe Leu Asn Asp Pro Gln Ala Phe
385                 390                 395                 400
Asn Glu Ala Phe Ala Arg Ala Trp Phe Lys Leu Thr His Arg Asp Met
            405                 410                 415
Gly Pro Lys Ser Arg Tyr Ile Gly Pro Glu Val Pro Lys Glu Asp Leu
            420                 425                 430
Ile Trp Gln Asp Pro Leu Pro Gln Pro Ile Tyr Asn Pro Thr Glu Gln
            435                 440                 445
Asp Ile Ile Asp Leu Lys Phe Ala Ile Ala Asp Ser Gly Leu Ser Val
            450                 455                 460
Ser Glu Leu Val Ser Val Ala Trp Ala Ser Ala Ser Thr Phe Arg Gly
465                 470                 475                 480
Gly Asp Lys Arg Gly Gly Ala Asn Gly Ala Arg Leu Ala Leu Met Pro
            485                 490                 495
Gln Arg Asp Trp Asp Val Asn Ala Ala Ala Val Arg Ala Leu Pro Val
            500                 505                 510
Leu Glu Lys Ile Gln Lys Glu Ser Gly Lys Ala Ser Leu Ala Asp Ile
            515                 520                 525
Ile Val Leu Ala Gly Val Val Gly Val Glu Lys Ala Ala Ser Ala Ala
            530                 535                 540
Gly Leu Ser Ile His Val Pro Phe Ala Pro Gly Arg Val Asp Ala Arg
545                 550                 555                 560
Gln Asp Gln Thr Asp Ile Glu Met Phe Glu Leu Leu Glu Pro Ile Ala
            565                 570                 575
Asp Gly Phe Arg Asn Tyr Arg Ala Arg Leu Asp Val Ser Thr Thr Glu
            580                 585                 590
Ser Leu Leu Ile Asp Lys Ala Gln Gln Leu Thr Leu Thr Ala Pro Glu
            595                 600                 605
```

```
Met Thr Ala Leu Val Gly Gly Met Arg Val Leu Gly Ala Asn Phe Asp
            610                 615                 620

Gly Ser Lys Asn Gly Val Phe Thr Asp Arg Val Gly Val Leu Ser Asn
625                 630                 635                 640

Asp Phe Phe Val Asn Leu Leu Asp Met Arg Tyr Glu Trp Lys Ala Thr
                645                 650                 655

Asp Glu Ser Lys Glu Leu Phe Glu Gly Arg Asp Arg Glu Thr Gly Glu
            660                 665                 670

Val Lys Phe Thr Ala Ser Arg Ala Asp Leu Val Phe Gly Ser Asn Ser
        675                 680                 685

Val Leu Arg Ala Val Ala Glu Val Tyr Ala Ser Ser Asp Ala His Glu
    690                 695                 700

Lys Phe Val Lys Asp Phe Val Ala Ala Trp Val Lys Val Met Asn Leu
705                 710                 715                 720

Asp Arg Phe Asp Leu Leu
                725

<210> SEQ ID NO 16
<211> LENGTH: 6329
<212> TYPE: DNA
<213> ORGANISM: artificial sequence
<220> FEATURE:
<223> OTHER INFORMATION: Plasmid pKD46

<400> SEQUENCE: 16
catcgattta ttatgacaac ttgacggcta catcattcac tttttcttca caaccggcac      60
ggaactcgct cgggctggcc ccggtgcatt ttttaaatac ccgcgagaaa tagagttgat     120
cgtcaaaacc aacattgcga ccgacggtgg cgataggcat ccgggtggtg ctcaaaagca     180
gcttcgcctg gctgatacgt tggtcctcgc gccagcttaa gacgctaatc cctaactgct     240
ggcggaaaag atgtgacaga cgcgacggcg acaagcaaac atgctgtgcg acgctggcga     300
tatcaaaatt gctgtctgcc aggtgatcgc tgatgtactg acaagcctcg cgtacccgat     360
tatccatcgg tggatggagc gactcgttaa tcgcttccat cgccgcagt aacaattgct     420 caagcagatt tatcgccagc agctccgaat agcgcccttc ccttgcccg gcgttaatga     480 tttgcccaaa caggtcgctg aaatgcggct ggtgcgcttc atccgggcga agaaccccg     540 tattggcaaa tattgacggc cagttaagcc attcatgcca gtaggcgcgc ggacgaaagt     600
aaacccactg gtgataccat tcgcgagcct ccggatgacg accgtagtga tgaatctctc     660
ctggcgggaa cagcaaaata tcacccggtc ggcaaacaaa ttctcgtccc tgattttca     720 ccacccctg accgcgaatg gtgagattga aatataacc tttcattcc agcggtcggt     780 cgataaaaaa atcgagataa ccgttggcct caatcggcgt taaacccgcc accagatggg     840
cattaaacga gtatcccggc agcaggggat cattttgcgc ttcagccata cttttcatac     900
tcccgccatt cagagaagaa accaattgtc catattgcat cagacattgc cgtcactgcg     960
tcttttactg gctcttctcg ctaaccaaac cggtaacccc gcttattaaa agcattctgt    1020
aacaaagcgg gaccaaagcc atgacaaaaa cgcgtaacaa agtgtctat aatcacggca    1080 gaaaagtcca cattgattat ttgcacggcg tcacactttg ctatgccata gcatttttat    1140
ccataagatt agcggatcct acctgacgct tttatcgca actctctact gtttctccat    1200
acccgttttt ttgggaattc gagctctaag gaggttataa aaatggata ttaatactga    1260 aactgagatc aagcaaaagc attcactaac cccctttcct gttttcctaa tcagcccggc    1320
atttcgcggg cgatattttc acagctattt caggagttca gccatgaacg cttattacat    1380
```

```
tcaggatcgt cttgaggctc agagctgggc gcgtcactac cagcagctcg cccgtgaaga    1440
gaaagaggca gaactggcag acgacatgga aaaaggcctg ccccagcacc tgtttgaatc    1500
gctatgcatc gatcatttgc aacgccacgg ggccagcaaa aaatccatta cccgtgcgtt    1560
tgatgacgat gttgagtttc aggagcgcat ggcagaacac atccggtaca tggttgaaac    1620
cattgctcac caccaggttg atattgattc agaggtataa aacgaatgag tactgcactc    1680
gcaacgctgg ctgggaagct ggctgaacgt gtcggcatgg attctgtcga cccacaggaa    1740
ctgatcacca ctcttcgcca gacggcattt aaaggtgatg ccagcgatgc gcagttcatc    1800
gcattactga tcgttgccaa ccagtacggc cttaatccgt ggacgaaaga aatttacgcc    1860
tttcctgata agcagaatgg catcgttccg gtggtgggcg ttgatggctg gtcccgcatc    1920
atcaatgaaa accagcagtt tgatggcatg gactttgagc aggacaatga atcctgtaca    1980
tgccggattt accgcaagga ccgtaatcat ccgatctgcg ttaccgaatg gatggatgaa    2040
tgccgccgcg aaccattcaa aactcgcgaa ggcagagaaa tcacggggcc gtggcagtcg    2100
catcccaaac ggatgttacg tcataaagcc atgattcagt gtgcccgtct ggccttcgga    2160
tttgctggta tctatgacaa ggatgaagcc gagcgcattg tcgaaaatac tgcatacact    2220
gcagaacgtc agccggaacg cgacatcact ccggttaacg atgaaaccat gcaggagatt    2280
aacactctgc tgatcgccct ggataaaaca tgggatgacg acttattgcc gctctgttcc    2340
cagatatttc gccgcgacat tcgtgcatcg tcagaactga cacaggccga agcagtaaaa    2400
gctcttggat tcctgaaaca gaaagccgca gagcagaagg tggcagcatg acaccggaca    2460
ttatcctgca gcgtaccggg atcgatgtga gagctgtcga acaggggat gatgcgtggc    2520 acaaattacg gctcggcgtc atcaccgctt cagaagttca caacgtgata gcaaaacccc    2580
gctccggaaa gaagtggcct gacatgaaaa tgtcctactt ccacaccctg cttgctgagg    2640
tttgcaccgg tgtggctccg gaagttaacg ctaaagcact ggcctgggga aaacagtacg    2700
agaacgacgc cagaaccctg tttgaattca cttccggcgt gaatgttact gaatccccga    2760
tcatctatcg cgacgaaagt atgcgtaccg cctgctctcc cgatggttta tgcagtgacg    2820
gcaacggcct tgaactgaaa tgcccgttta cctcccggga tttcatgaag ttccggctcg    2880
gtggtttcga ggccataaag tcagcttaca tggcccaggt gcagtacagc atgtgggtga    2940
cgcgaaaaaa tgcctggtac tttgccaact atgacccgcg tatgaagcgt gaaggcctgc    3000
attatgtcgt gattgagcgg gatgaaaagt acatggcgag ttttgacgag atcgtgccgg    3060
agttcatcga aaaatggac gaggcactgg ctgaaattgg ttttgtattt ggggagcaat    3120
ggcgatgacg catcctcacg ataatatccg ggtaggcgca atcactttcg tctactccgt    3180
tacaaagcga ggctgggtat ttcccggcct ttctgttatc cgaaatccac tgaaagcaca    3240
gcggctggct gaggagataa ataataaacg aggggctgta tgcacaaagc atcttctgtt    3300
gagttaagaa cgagtatcga gatggcacat agccttgctc aaattggaat caggtttgtg    3360
ccaataccag tagaaacaga cgaagaatcc atgggtatgg acagttttcc ctttgatatg    3420
taacggtgaa cagttgttct acttttgttt gttagtcttg atgcttcact gatagataca    3480
agagccataa gaacctcaga tccttccgta tttagccagt atgttctcta gtgtggttcg    3540 ttgttttgc gtgagccatg agaacgaacc attgagatca tacttacttt gcatgtcact    3600
caaaaatttt gcctcaaaac tggtgagctg aattttgtgca gttaaagcat cgtgtagtgt    3660
ttttcttagt ccgttacgta ggtaggaatc tgatgtaatg gttgttggta ttttgtcacc    3720
attcattttt atctggttgt tctcaagttc ggttacgaga tccatttgtc tatctagttc    3780
```

```
aacttggaaa atcaacgtat cagtcgggcg gcctcgctta tcaaccacca atttcatatt   3840
gctgtaagtg tttaaatctt tacttattgg tttcaaaacc cattggttaa gccttttaaa   3900
ctcatggtag ttattttcaa gcattaacat gaacttaaat tcatcaaggc taatctctat   3960
atttgccttg tgagttttct tttgtgttag ttcttttaat aaccactcat aaatcctcat   4020
agagtatttg ttttcaaaag acttaacatg ttccagatta tattttatga attttttaa    4080
ctggaaaaga taaggcaata tctcttcact aaaaactaat tctaattttt cgcttgagaa   4140
cttggcatag tttgtccact ggaaaatctc aaagccttta accaaggat tcctgatttc    4200
cacagttctc gtcatcagct ctctggttgc tttagctaat acaccataag cattttccct   4260
actgatgttc atcatctgag cgtattggtt ataagtgaac gataccgtcc gttctttcct   4320
tgtagggttt tcaatcgtgg ggttgagtag tgccacacag cataaaatta gcttggtttc   4380
atgctccgtt aagtcatagc gactaatcgc tagttcattt gctttgaaaa caactaattc   4440
agacatacat ctcaattggt ctaggtgatt ttaatcacta taccaattga gatgggctag   4500
tcaatgataa ttactagtcc ttttcctttg agttgtgggt atctgtaaat tctgctagac   4560
ctttgctgga aaacttgtaa attctgctag accctctgta aattccgcta gacctttgtg   4620
tgttttttt gtttatattc aagtggttat aatttataga ataaagaaag aataaaaaaa    4680
gataaaaaga atagtcccca gccctgtgta taactcacta ctttagtcag ttccgcagta   4740
ttacaaaagg atgtcgcaaa cgctgtttgc tcctctacaa aacagacctt aaaaccctaa   4800
aggcttaagt agcaccctcg caagctcggt tgcggccgca atcgggcaaa tcgctgaata   4860
ttccttttgt ctccgaccat caggcacctg agtcgctgtc tttttcgtga cattcagttc   4920
gctgcgctca cggctctggc agtgaatggg ggtaaatggc actacaggcg ccttttatgg   4980
attcatgcaa ggaaactacc cataatacaa gaaaagcccg tcacgggctt tcagggcgt    5040
tttatggcgg gtctgctatg tggtgctatc tgactttttg ctgttcagca gttcctgccc   5100
tctgattttc cagtctgacc acttcggatt atcccgtgac aggtcattca gactggctaa   5160
tgcacccagt aaggcagcgg tatcatcaac ggggtctgac gctcagtgga acgaaaactc   5220
acgttaaggg attttggtca tgagattatc aaaaaggatc ttcacctaga tccttttaaa   5280
ttaaaaatga agttttaaat caatctaaag tatatatgag taaacttggt ctgacagtta   5340
ccaatgctta atcagtgagg cacctatctc agcgatctgt ctatttcgtt catccatagt   5400
tgcctgactc cccgtcgtgt agataactac gatacgggag ggcttaccat ctggccccag   5460
tgctgcaatg ataccgcgag acccacgctc accggctcca gatttatcag caataaacca   5520
gccagccgga agggccgagc gcagaagtgg tcctgcaact ttatccgcct ccatccagtc   5580
tattaattgt tgccgggaag ctagagtaag tagttcgcca gttaatagtt tgcgcaacgt   5640
tgttgccatt gctacaggca tcgtggtgtc acgctcgtcg tttggtatgg cttcattcag   5700
ctccggttcc caacgatcaa ggcgagttac atgatccccc atgttgtgca aaaaagcggt   5760
tagctccttc ggtcctccga tcgttgtcag aagtaagttg gccgcagtgt tatcactcat   5820
ggttatggca gcactgcata attctcttac tgtcatgcca tccgtaagat gcttttctgt   5880
gactggtgag tactcaacca agtcattctg agaatagtgt atgcggcgac cgagttgctc   5940
ttgcccggcg tcaatacggg ataataccgc gccacatagc agaactttaa aagtgctcat   6000
cattggaaaa cgttcttcgg ggcgaaaact ctcaaggatc ttaccgctgt tgagatccag   6060
ttcgatgtaa cccactcgtg cacccaactg atcttcagca tcttttactt tcaccagcgt   6120
ttctgggtga gcaaaaacag gaaggcaaaa tgccgcaaaa aagggaataa gggcgacacg   6180
```

-continued

| gaaatgttga atactcatac tcttcctttt tcaatattat tgaagcattt atcagggtta | 6240 |
| ttgtctcatg agcggataca tatttgaatg tatttagaaa aataaacaaa tagggggttcc | 6300 |
| gcgcacattt ccccgaaaag tgccacctg | 6329 |

<210> SEQ ID NO 17
<211> LENGTH: 25
<212> TYPE: DNA
<213> ORGANISM: artificial sequence
<220> FEATURE:
<223> OTHER INFORMATION: Primer

<400> SEQUENCE: 17

| aacaatatgt aagatctcaa ctatc | 25 |

<210> SEQ ID NO 18
<211> LENGTH: 25
<212> TYPE: DNA
<213> ORGANISM: artificial sequence
<220> FEATURE:
<223> OTHER INFORMATION: Primer

<400> SEQUENCE: 18

| cagacatgag agatccagtg tgtag | 25 |

<210> SEQ ID NO 19
<211> LENGTH: 9332
<212> TYPE: DNA
<213> ORGANISM: artificial sequence
<220> FEATURE:
<223> OTHER INFORMATION: Plasmid pCP20

<400> SEQUENCE: 19

| gagacacaac gtggctttgt tgaataaatc gaacttttgc tgagttgaag gatcagatca | 60 |
| cgcatcttcc cgacaacgca gaccgttccg tggcaaagca aaagttcaaa atcaccaact | 120 |
| ggtccaccta caacaaagct ctcatcaacc gtggctccct cactttctgg ctggatgatg | 180 |
| gggcgattca ggcctggtat gagtcagcaa caccttcttc acgaggcaga cctcagcgcc | 240 |
| acaggtgcgg ttgctggcgc taaccgtttt tatcaggctc tgggaggcag aataaatgat | 300 |
| catatcgtca attattacct ccacggggag agcctgagca aactggcctc aggcatttga | 360 |
| gaagcacacg gtcacactgc ttccggtagt caataaaccg gtaaaccagc aatagacata | 420 |
| agcggctatt taacgaccct gccctgaacc gacgaccggg tcgaatttgc tttcgaattt | 480 |
| ctgccattca tccgcttatt atcacttatt caggcgtagc aaccaggcgt ttaagggcac | 540 |
| caataactgc cttaaaaaaa ttacgccccg ccctgccact catcgcagta ctgttgtaat | 600 |
| tcattaagca ttctgccgac atggaagcca tcacaaacgg catgatgaac ctgaatcgcc | 660 |
| agcggcatca gcaccttgtc gccttgcgta taatatttgc ccatggtgaa aacggggggcg | 720 |
| aagaagttgt ccatattggc cacgtttaaa tcaaaactgg tgaaactcac ccagggattg | 780 |
| gctgagacga aaaacatatt ctcaataaac cctttaggga ataggccag ttttcaccg | 840 |
| taacacgcca tcttgcgca atatatgtgt agaaactgcc ggaaatcgtc gtggtattca | 900 |
| ctccagagcg atgaaaacgt ttcagtttgc tcatggaaaa cggtgtaaca agggtgaaca | 960 |
| ctatcccata tcaccagctc accgtctttc attgccatac ggaattccgg atgagcattc | 1020 |
| atcaggcggg caagaatgtg aataaaggcc ggataaaact tgtgcttatt tttctttacg | 1080 |
| gtctttaaaa aggccgtaat atccagctga acggtctggt tataggtaca ttgagcaact | 1140 |
| gactgaaatg cctcaaaatg ttctttacga tgccattggg atatatcaac ggtggtatat | 1200 |

```
ccagtgattt ttttctccat tttagcttcc ttagctcctg aaaatctcga taactcaaaa    1260
aatacgcccg gtagtgatct tatttcatta tggtgaaagt tggaacctct tacgtgccga    1320
tcaacgtctc attttcgcca aaagttggcc cagggcttcc cggtatcaac agggacacca    1380
ggatttattt attctgcgaa gtgatcttcc gtcacaggta tttattcggc gcaaagtgcg    1440
tcgggtgatg ctgccaactt actgatttag tgtatgatgg tgttttttgag gtgctccagt    1500 ggcttctgtt tctatcagct gtccctcctg ttcagctact gacggggtgg tgcgtaacgg    1560
caaaagcacc gccggacatc agcgcttgtt tcggcgtggg tatggtggca ggccccgtgg    1620 ccggggggact gttgggcgcc tgtagtgcca tttaccccca ttcactgcca gagccgtgag    1680
cgcagcgaac tgaatgtcac gaaaaagaca gcgactcagg tgcctgatgg tcggagacaa    1740
aaggaatatt cagcgatttg cccgagcttg cgagggtgct acttaagcct ttagggtttt    1800
aaggtctgtt ttgtagagga gcaaacagcg tttgcgacat ccttttgtaa tactgcggaa    1860
ctgactaaag tagtgagtta tacacagggc tgggatctat tcttttatc ttttttatt    1920 ctttctttat tctataaatt ataaccactt gaatataaac aaaaaaaaca cacaaaggtc    1980
tagcggaatt tacagagggt ctagcagaat ttacaagttt tccagcaaag gtctagcaga    2040
atttacagat acccacaact caaaggaaaa ggactagtaa ttatcattga ctagcccatc    2100
tcaattggta tagtgattaa aatcacctag accaattgag atgtatgtct gaattagttg    2160
ttttcaaagc aaatgaacta gcgattagtc gctatgactt aacggagcat gaaaccaagc    2220
taattttatg ctgtgtggca ctactcaacc ccacgattga aaaccctaca aggaaagaac    2280
ggacggtatc gttcacttat aaccaatacg ttcagatgat gaacatcagt agggaaaatg    2340
cttatggtgt attagctaaa gcaaccgag agctgatgac gagaactgtg gaaatcagga    2400
atcctttggt taaaggcttt gagattttcc agtggacaaa ctatgccaag ttctcaagcg    2460
aaaaattaga attagttttt agtgaagaga tattgcctta tcttttccag ttaaaaaaat    2520
tcataaaata taatctggaa catgttaagt cttttgaaaa caaatactct atgaggattt    2580
atgagtggtt attaaaagaa ctaacacaaa agaaaactca caaggcaaat atagagatta    2640
gccttgatga atttaagttc atgttaatgc ttgaaaataa ctaccatgag tttaaaggc    2700 ttaaccaatg ggttttgaaa ccaataagta aagatttaaa cacttacagc aatatgaaat    2760
tggtggttga taagcgaggc cgcccgactg atacgttgat tttccaagtt gaactagata    2820
gacaaatgga tctcgtaacc gaacttgaga caaccagat aaaaatgaat ggtgacaaaa    2880
taccaacaac cattacatca gattcctacc tacataacgg actaagaaaa acactacacg    2940
atgctttaac tgcaaaaatt cagctcacca gttttgaggc aaaattttg agtgacatgc    3000 aaagtaagta tgatctcaat ggttcgttct catggctcac gcaaaaacaa cgaaccacac    3060
tagagaacat actggctaaa tacggaagga tctgaggttc ttatggctct tgtatctatc    3120
agtgaagcat caagactaac aaacaaaagt agaacaactg ttcaccgtta catatcaaag    3180
ggaaaactgt ccatatgcac agatgaaaac ggtgtaaaaa agatagatac atcagagctt    3240
ttacgagttt ttggtgcatt taaagctgtt caccatgaac agatcgacaa tgtaacagat    3300
gaacagcatg taacacctaa tagaacaggt gaaaccagta aaacaaagca actagaacat    3360
gaaattgaac acctgagaca acttgttaca gctcaacagt cacacataga cagcctgaaa    3420
caggcgatgc tgcttatcga atcaaagctg ccgacaacac gggagccagt gacgcctccc    3480
gtggggaaaa aatcatggca attctggaag aaatagcgcc tgtttcgttt caggcaggtt    3540
atcagggagt gtcagcgtcc tgcggttctc cggggcgttc gggtcatgca gcccgtaatg    3600
```

```
gtgatttacc agcgtctgcc aggcatcaat tctaggcctg tctgcgcggt cgtagtacgg    3660
ctggaggcgt tttccggtct gtagctccat gttcggaatg acaaaattca gctcaagccg    3720
tcccttgtcc tggtgctcca cccacaggat gctgtactga ttttttttcga gaccgggcat   3780 cagtacacgc tcaaagctcg ccatcacttt ttcacgtcct cccggcggca gctccttctc    3840
cgcgaacgac agaacaccgg acgtgtattt cttcgcaaat ggcgtggcat cgatgagttc    3900
ccggacttct tccggattac cctgaagcac cgttgcgcct tcgcggttac gctccctccc    3960
cagcaggtaa tcaaccggac cactgccacc accttttccc ctggcatgaa atttaactat    4020
catcccgcgc ccctgttcc ctgacagcca gacgcagccg cgcagctca tccccgatgg      4080 ccatcagtgc ggccaccacc tgaacccggt caccggaaga ccactgcccg ctgttcacct    4140
tacgggctgt ctgattcagg ttatttccga tggcggccag ctgacgcagt aacggcggtg    4200
ccagtgtcgg cagttttccg aacgggcaa ccggctcccc caggcagacc cgccgcatcc     4260
ataccgccag ttgtttaccc tcacagcgtt caagtaaccg ggcatgttca tcatcagtaa    4320
cccgtattgt gagcatcctc tcgcgtttca tcggtatcat taccccatga acagaaatcc   4380
cccttacacg gaggcatcag tgactaaacg gggtctgacg ctcagtggaa cgaaaactca    4440
cgttaaggga ttttggtcat gagattatca aaaaggatct tcacctagat ccttttaaat   4500
taaaaatgaa gttttaaatc aatctaaagt atatatgagt aaacttggtc tgacagttac    4560
caatgcttaa tcagtgaggc acctatctca gcgatctgtc tatttcgttc atccatagtt    4620
gcctgactcc ccgtcgtgta gataactacg atacgggagg gcttaccatc tggccccagt    4680
gctgcaatga taccgcgaga cccacgctca ccggctccag atttatcagc aataaaccag    4740
ccagccggaa gggccgagcg cagaagtggt cctgcaactt tatccgcctc catccagtct    4800
attaattgtt gccgggaagc tagagtaagt agttcgccag ttaatagttt gcgcaacgtt    4860
gttgccattg ctgcaggcat cgtggtgtca cgctcgtcgt ttggtatggc ttcattcagc    4920
tccggttccc aacgatcaag gcgagttaca tgatccccca tgttgtgcaa aaaagcggtt    4980 agctcccttcg gtcctccgat cgttgtcaga agtaagttgg ccgcagtgtt atcactcatg   5040
gttatggcag cactgcataa ttctcttact gtcatgccat ccgtaagatg cttttctgtg    5100
actggtgagt actcaaccaa gtcattctga gaatagtgta tgcggcgacc gagttgctct    5160
tgcccggcgt caacacggga taataccgcg ccacatagca gaactttaaa agtgctcatc    5220
attggaaaac gttcttcggg gcgaaaactc tcaaggatct taccgctgtt gagatccagt    5280
tcgatgtaac ccactcgtgc acccaactga tcttcagcat cttttacttt caccagcgtt    5340
tctgggtgag caaaaacagg aaggcaaaat gccgcaaaaa agggaataag ggcgacacgg    5400
aaatgttgaa tactcatact cttcctttt caatattatt gaagcattta tcagggttat     5460
tgtctcatga gcggatacat atttgaatgt atttagaaaa ataaacaaat aggggttccg    5520
cgcacatttc cccgaaaagt gccacctgac gtctaagaaa ccattattat catgacatta    5580
acctataaaa ataggcgtat cacgaggccc tttcgtcttc aagaatttta taaaccgtgg    5640
agcgggcaat actgagctga tgagcaattt ccgttgcacc agtgcccttc tgatgaagcg    5700
tcagcacgac gttcctgtcc acggtacgcc tgcggccaaa tttgattcct ttcagctttg    5760
cttcctgtcg gccctcattc gtgcgctcta ggatcctcta cgccgacgc atcgtggccg     5820 gcatcaccgg cgctgaggtc tgcctcgtga agaaggtgtt gctgactcat accaggcctg    5880
aatcgcccca tcatccagcc agaaagtgag ggagccacgg ttgatgagag ctttgttgta    5940
ggtggaccag ttggtgattt tgaacttttg ctttgccacg gaacggtctg cgttgtcggg    6000
```

```
aagatgcgtg atctgatcct tcaactcagc aaaagttcga tttattcaac aaagccgccg   6060
tcccgtcaag tcagcgtaat gctctgccag tgttacaacc aattaaccaa ttctgattag   6120
aaaaactcat cgagcatcaa atgaaactgc aatttattca tatcaggatt atcaatacca   6180 tattttgaa aaagccgttt ctgtaatgaa ggagaaaact caccgaggca gttccatagg    6240
atggcaagat cctggtatcg gtctgcgatt ccgactcgtc aacatcaat acaacctatt    6300 aatttcccct cgtcaaaaat aaggttatca agtgagaaat caccatgagt gacgactgaa   6360
tccggtgaga atggcagaat aggaacttcg gaataggaac ttcaaagcgt ttccgaaaac   6420
gagcgcttcc gaaaatgcaa cgcgagctgc gcacatacag ctcactgttc acgtcgcacc   6480
tatatctgcg tgttgcctgt atatatat acatgagaag aacggcatag tgcgtgttta    6540
tgcttaaatg cgtacttata tgcgtctatt tatgtaggat gaaaggtagt ctagtacctc   6600
ctgtgatatt atcccattcc atgcggggta tcgtatgctt ccttcagcac tacccttttag  6660 ctgttctata tgctgccact cctcaattgg attagtctca tccttcaatg ctatcatttc   6720
ctttgatatt ggatcatatg catagtaccg agaaactagt gcgaagtagt gatcaggtat   6780
tgctgttatc tgatgagtat acgttgtcct ggccacggca gaagcacgct tatcgctcca   6840
atttcccaca acattagtca actccgttag gcccttcatt gaaagaaatg aggtcatcaa   6900
atgtcttcca atgtgagatt tgggccatt tttatagca aagattgaat aaggcgcatt     6960
tttcttcaaa gctttattgt acgatctgac taagttatct tttaataatt ggtattcctg   7020
tttattgctt gaagaattgc cggtcctatt tactcgtttt aggactggtt cagaattcct   7080
caaaaattca tccaaatata caagtggatc gatcctaccc cttgcgctaa agaagtatat   7140
gtgcctacta acgcttgtct ttgtctctgt cactaaacac tggattatta ctcccagata   7200
cttattttgg actaatttaa atgatttcgg atcaacgttc ttaatatcgc tgaatcttcc   7260
acaattgatg aaagtagcta ggaagaggaa ttggtataaa gttttttgtt ttgtaaatct   7320
cgaagtatac tcaaacgaat ttagtatttt ctcagtgatc tcccagatgc tttcacccts   7380
acttagaagt gctttaagca ttttttttact gtggctattt cccttatctg cttcttccga   7440
tgattcgaac tgtaattgca aactactac aatatcagtg atatcagatt gatgtttttg    7500
tccatagtaa ggaataattg taaattccca agcaggaatc aatttcttta atgaggcttc    7560
cagaattgtt gcttttttgcg tcttgtattt aaactggagt gatttattga caatatcgaa   7620
actcagcgaa ttgcttatga tagtattata gctcatgaat gtggctctct tgattgctgt    7680
tccgttatgt gtaatcatcc aacataaata ggttagttca gcagcacata atgctatttt    7740
ctcacctgaa ggtctttcaa accttttcac aaactgacga acaagcacct taggtggtgt    7800
tttacataat atatcaaatt gtggcataca acctccttag tacatgcaac cattatcacc    7860
gccagaggta aaatagtcaa cacgcacggt gttagatatt tatcccttgc ggtgatagat    7920
ttaacgtatg agcacaaaaa agaaaccatt aacacaagag cagcttgagg acgcacgtcg    7980
ccttaaagca atttatgaaa aaaagaaaaa tgaacttggc ttatcccagg aatctgtcgc    8040
agacaagatg gggatggggc agtcaggcgt tggtgcttta tttaatggca tcaatgcatt    8100
aaatgcttat aacgccgcat tgcttacaaa aattctcaaa gttagcgttg aagaatttag    8160
cccttcaatc gccagagaaa tctacgagat gtatgaagcg gttagtatgc agccgtcact    8220
tagaagtgag tatgagtacc ctgttttttc tcatgttcag gcagggatgt tctcacctaa    8280
gcttagaacc tttaccaaag gtgatgcgga gagatggga agcacaacca aaaaagccag     8340
tgattctgca ttctggcttg aggttgaagg taattccatg accgcaccaa caggctccaa    8400
```

```
gccaagcttt cctgacggaa tgttaattct cgttgaccct gagcaggctg ttgagccagg    8460
tgatttctgc atagccagac ttgggggtga tgagtttacc ttcaagaaac tgatcaggga    8520
tagcggtcag gtgtttttac aaccactaaa cccacagtac ccaatgatcc catgcaatga    8580
gagttgttcc gttgtgggga aagttatcgc tagtcagtgg cctgaagaga cgtttggctg    8640
atcggcaagg tgttctggtc ggcgcatagc tgataacaat tgagcaagaa tctgcatttc    8700
tttccagact tgttcaacag gccagccatt acgctcgtca tcaaaatcac tcgcatcaac    8760
caaaccgtta ttcattcgtg attgcgcctg agcgagacga aatacgcgat cgctgttaaa    8820
aggacaatta caaacaggaa tcgaatgcaa ccggcgcagg aacactgcca gcgcatcaac    8880
aatattttca cctgaatcag gatattcttc taatacctgg aatgctgttt cccggggat     8940 cgcagtggtg agtaaccatg catcatcagg agtacggata aaatgcttga tggtcggaag    9000
aggcataaat tccgtcagcc agtttagtct gaccatctca tctgtaacat cattggcaac    9060
gctacctttg ccatgtttca gaaacaactc tggcgcatcg gcttcccat acaatcgata     9120 gattgtcgca cctgattgcc cgacattatc gcagcccat ttatacccat ataaatcagc     9180
atccatgttg gaatttaatc gcggcctcga gcaagacgtt tcccgttgaa tatggctcat    9240
aacacccctt gtattactgt ttatgtaagc agacagtttt attgttcatg atgatatatt    9300
tttatcttgt gcaatgtaac atcagagatt tt                                  9332

<210> SEQ ID NO 20
<211> LENGTH: 80
<212> TYPE: DNA
<213> ORGANISM: artificial sequence
<220> FEATURE:
<223> OTHER INFORMATION: Primer

<400> SEQUENCE: 20
atgtcgcaac ataacgaaaa gaacccacat cagcaccagt caccactaca cgattccagc     60
gtgtaggctg gagctgcttc                                                 80

<210> SEQ ID NO 21
<211> LENGTH: 82
<212> TYPE: DNA
<213> ORGANISM: artificial sequence
<220> FEATURE:
<223> OTHER INFORMATION: Primer

<400> SEQUENCE: 21
ttacgccggg attttgtcaa tcttaggaat gcgtgaccac acgcggtgtg ctgtcatcag     60
attccgggga tccgtcgacc tg                                              82

<210> SEQ ID NO 22
<211> LENGTH: 1424
<212> TYPE: DNA
<213> ORGANISM: artificial sequence
<220> FEATURE:
<223> OTHER INFORMATION: Synthetic construct

<400> SEQUENCE: 22
ttacgccggg attttgtcaa tcttaggaat gcgtgaccac acgcggtgtg ctgtcatcag     60
attccgggga tccgtcgacc tgcagttcga agttcctatt ctctagaaag tataggaact    120
tcagagcgct tttgaagctc acgctgccgc aagcactcag ggcgcaaggg ctgctaaagg    180
aagcggaaca cgtagaaagc cagtccgcag aaacggtgct gacccggat gaatgtcagc     240 tactgggcta tctggacaag ggaaaacgca agcgcaaaga gaaagcaggt agcttgcagt    300
```

-continued

```
gggcttacat ggcgatagct agactgggcg gttttatgga cagcaagcga accggaattg    360
ccagctgggg cgccctctgg taaggttggg aagccctgca aagtaaactg gatggctttc    420
ttgccgccaa ggatctgatg gcgcagggga tcaagatctg atcaagagac aggatgagga    480
tcgtttcgca tgattgaaca agatggattg cacgcaggtt ctccggccgc ttgggtggag    540
aggctattcg gctatgactg ggcacaacag acaatcggct gctctgatgc cgccgtgttc    600
cggctgtcag cgcaggggcg cccggttctt tttgtcaaga ccgacctgtc cggtgccctg    660
aatgaactgc aggacgaggc agcgcggcta tcgtggctgg ccacgacggg cgttccttgc    720
gcagctgtgc tcgacgttgt cactgaagcg ggaagggact ggctgctatt gggcgaagtg    780
ccggggcagg atctcctgtc atctcacctt gctcctgccg agaaagtatc catcatggct    840
gatgcaatgc ggcggctgca tacgcttgat ccggctaccT gcccattcga ccaccaagcg    900
aaacatcgca tcgagcgagc acgtactcgg atggaagccg gtcttgtcga tcaggatgat    960
ctggacgaag agcatcaggg gctcgcgcca gccgaactgt tcgccaggct caaggcgcgc   1020
atgcccgacg gcgaggatct cgtcgtgacc catggcgatg cctgcttgcc gaatatcatg   1080
gtggaaaatg gccgcttttc tggattcatc gactgtggcc ggctgggtgt ggcggaccgc   1140
tatcaggaca tagcgttggc tacccgtgat attgctgaag agcttggcgg cgaatgggct   1200
gaccgcttcc tcgtgcttta cggtatcgcc gctcccgatt cgcagcgcat cgccttctat   1260
cgccttcttg acgagttctt ctaataaggg gatcttgaag ttcctattcc gaagttccta   1320
ttctctagaa agtataggaa cttcgaagca gctccagcct acacgctgga atcgtgtagt   1380
ggtgactggt gctgatgtgg gttctttccg ttatgttgcg acat                    1424
```

<210> SEQ ID NO 23
<211> LENGTH: 2262
<212> TYPE: DNA
<213> ORGANISM: Escherichia coli
<220> FEATURE:
<221> NAME/KEY: CDS
<222> LOCATION: (1)..(2262)

<400> SEQUENCE: 23

```
atg tcg caa cat aac gaa aag aac cca cat cag cac cag tca cca cta      48
Met Ser Gln His Asn Glu Lys Asn Pro His Gln His Gln Ser Pro Leu
1               5                   10                  15 cac gat tcc agc gaa gcg aaa ccg ggg atg gac tca ctg gca cct gag      96
His Asp Ser Ser Glu Ala Lys Pro Gly Met Asp Ser Leu Ala Pro Glu
                20                  25                  30 gac ggc tct cat cgt cca gcg gct gaa cca aca ccg cca ggt gca caa     144
Asp Gly Ser His Arg Pro Ala Ala Glu Pro Thr Pro Pro Gly Ala Gln
            35                  40                  45 cct acc gcc cca ggg agc ctg aaa gcc cct gat acg cgt aac gaa aaa     192
Pro Thr Ala Pro Gly Ser Leu Lys Ala Pro Asp Thr Arg Asn Glu Lys
        50                  55                  60 ctt aat tct ctg gaa gac gta cgc aaa ggc agt gaa aat tat gcg ctg     240
Leu Asn Ser Leu Glu Asp Val Arg Lys Gly Ser Glu Asn Tyr Ala Leu
65                  70                  75                  80 acc act aat cag ggc gtg cgc atc gcc gac gat caa aac tca ctg cgt     288
Thr Thr Asn Gln Gly Val Arg Ile Ala Asp Asp Gln Asn Ser Leu Arg
                85                  90                  95 gcc ggt agc cgt ggt cca acg ctg ctg gaa gat ttt att ctg cgc gag     336
Ala Gly Ser Arg Gly Pro Thr Leu Leu Glu Asp Phe Ile Leu Arg Glu
            100                 105                 110 aaa atc acc cac ttt gac cat gag cgc att ccg gaa cgt att gtt cat     384
Lys Ile Thr His Phe Asp His Glu Arg Ile Pro Glu Arg Ile Val His
        115                 120                 125
```

| | | |
|---|---|---|
| gca cgc gga tca gcc gct cac ggt tat ttc cag cca tat aaa agc tta<br>Ala Arg Gly Ser Ala Ala His Gly Tyr Phe Gln Pro Tyr Lys Ser Leu<br>130                        135                    140 | | 432 |
| agc gat att acc aaa gcg gat ttc ctc tca gat ccg aac aaa atc acc<br>Ser Asp Ile Thr Lys Ala Asp Phe Leu Ser Asp Pro Asn Lys Ile Thr<br>145                      150                  155                  160 | | 480 |
| cca gta ttt gta cgt ttc tct acc gtt cag ggt ggt gct ggc tct gct<br>Pro Val Phe Val Arg Phe Ser Thr Val Gln Gly Gly Ala Gly Ser Ala<br>              165                  170                  175 | | 528 |
| gat acc gtg cgt gat atc cgt ggc ttt gcc acc aag ttc tat acc gaa<br>Asp Thr Val Arg Asp Ile Arg Gly Phe Ala Thr Lys Phe Tyr Thr Glu<br>           180                  185                  190 | | 576 |
| gag ggt att ttt gac ctc gtt ggc aat aac acg cca atc ttc ttt atc<br>Glu Gly Ile Phe Asp Leu Val Gly Asn Asn Thr Pro Ile Phe Phe Ile<br>195                        200                  205 | | 624 |
| cag gat gcg cat aaa ttc ccc gat ttt gtt cat gcg gta aaa cca gaa<br>Gln Asp Ala His Lys Phe Pro Asp Phe Val His Ala Val Lys Pro Glu<br>           210                  215                  220 | | 672 |
| ccg cac tgg gca att cca caa ggg caa agt gcc cac gat act ttc tgg<br>Pro His Trp Ala Ile Pro Gln Gly Gln Ser Ala His Asp Thr Phe Trp<br>225                        230                  235                  240 | | 720 |
| gat tat gtt tct ctg caa cct gaa act ctg cac aac gtg atg tgg gcg<br>Asp Tyr Val Ser Leu Gln Pro Glu Thr Leu His Asn Val Met Trp Ala<br>                      245                  250                  255 | | 768 |
| atg tcg gat cgc ggc atc ccc cgc agt tac cgc acc atg gaa ggc ttc<br>Met Ser Asp Arg Gly Ile Pro Arg Ser Tyr Arg Thr Met Glu Gly Phe<br>           260                  265                  270 | | 816 |
| ggt att cac acc ttc cgc ctg att aat gcc gaa ggg aag gca acg ttt<br>Gly Ile His Thr Phe Arg Leu Ile Asn Ala Glu Gly Lys Ala Thr Phe<br>275                        280                  285 | | 864 |
| gta cgt ttc cac tgg aaa cca ctg gca ggt aaa gcc tca ctc gtt tgg<br>Val Arg Phe His Trp Lys Pro Leu Ala Gly Lys Ala Ser Leu Val Trp<br>           290                  295                  300 | | 912 |
| gat gaa gca caa aaa ctc acc gga cgt gac ccg gac ttc cac cgc cgc<br>Asp Glu Ala Gln Lys Leu Thr Gly Arg Asp Pro Asp Phe His Arg Arg<br>305                        310                  315                  320 | | 960 |
| gag ttg tgg gaa gcc att gaa gca ggc gat ttt ccg gaa tac gaa ctg<br>Glu Leu Trp Glu Ala Ile Glu Ala Gly Asp Phe Pro Glu Tyr Glu Leu<br>                      325                  330                  335 | | 1008 |
| ggc ttc cag ttg att cct gaa gaa gat gaa ttc aag ttc gac ttc gat<br>Gly Phe Gln Leu Ile Pro Glu Glu Asp Glu Phe Lys Phe Asp Phe Asp<br>           340                  345                  350 | | 1056 |
| ctt ctc gat cca acc aaa ctt atc ccg gaa gaa ctg gtg ccc gtt cag<br>Leu Leu Asp Pro Thr Lys Leu Ile Pro Glu Glu Leu Val Pro Val Gln<br>355                        360                  365 | | 1104 |
| cgt gtc ggc aaa atg gtg ctc aat cgc aac ccg gat aac ttc ttt gct<br>Arg Val Gly Lys Met Val Leu Asn Arg Asn Pro Asp Asn Phe Phe Ala<br>           370                  375                  380 | | 1152 |
| gaa aac gaa cag gcg gct ttc cat cct ggg cat atc gtg ccg gga ctg<br>Glu Asn Glu Gln Ala Ala Phe His Pro Gly His Ile Val Pro Gly Leu<br>385                        390                  395                  400 | | 1200 |
| gac ttc acc aac gat ccg ctg ttg cag gga cgt ttg ttc tcc tat acc<br>Asp Phe Thr Asn Asp Pro Leu Leu Gln Gly Arg Leu Phe Ser Tyr Thr<br>                      405                  410                  415 | | 1248 |
| gat aca caa atc agt cgt ctt ggt ggg ccg aat ttc cat gag att ccg<br>Asp Thr Gln Ile Ser Arg Leu Gly Gly Pro Asn Phe His Glu Ile Pro<br>           420                  425                  430 | | 1296 |
| att aac cgt ccg acc tgc cct tac cat aat ttc cag cgt gac ggc atg<br>Ile Asn Arg Pro Thr Cys Pro Tyr His Asn Phe Gln Arg Asp Gly Met<br>435                        440                  445 | | 1344 |

```
cat cgc atg ggg atc gac act aac ccg gcg aat tac gaa ccg aac tcg      1392
His Arg Met Gly Ile Asp Thr Asn Pro Ala Asn Tyr Glu Pro Asn Ser
    450                 455                 460 att aac gat aac tgg ccg cgc gaa aca ccg ccg ggg ccg aaa cgc ggc      1440
Ile Asn Asp Asn Trp Pro Arg Glu Thr Pro Pro Gly Pro Lys Arg Gly
465                 470                 475                 480 ggt ttt gaa tca tac cag gag cgc gtg gaa ggc aat aaa gtt cgc gag      1488
Gly Phe Glu Ser Tyr Gln Glu Arg Val Glu Gly Asn Lys Val Arg Glu
                485                 490                 495 cgc agc cca tcg ttt ggc gaa tat tat tcc cat ccg cgt ctg ttc tgg      1536
Arg Ser Pro Ser Phe Gly Glu Tyr Tyr Ser His Pro Arg Leu Phe Trp
            500                 505                 510 cta agt cag acg cca ttt gag cag cgc cat att gtc gat ggt ttc agt      1584
Leu Ser Gln Thr Pro Phe Glu Gln Arg His Ile Val Asp Gly Phe Ser
        515                 520                 525 ttt gag tta agc aaa gtc gtt cgt ccg tat att cgt gag cgc gtt gtt      1632
Phe Glu Leu Ser Lys Val Val Arg Pro Tyr Ile Arg Glu Arg Val Val
530                 535                 540 gac cag ctg gcg cat att gat ctc act ctg gcc cag gcg gtg gcg aaa      1680
Asp Gln Leu Ala His Ile Asp Leu Thr Leu Ala Gln Ala Val Ala Lys
545                 550                 555                 560 aat ctc ggt atc gaa ctg act gac gac cag ctg aat atc acc cca cct      1728
Asn Leu Gly Ile Glu Leu Thr Asp Asp Gln Leu Asn Ile Thr Pro Pro
                565                 570                 575 ccg gac gtc aac ggt ctg aaa aag gat cca tcc tta agt ttg tac gcc      1776
Pro Asp Val Asn Gly Leu Lys Lys Asp Pro Ser Leu Ser Leu Tyr Ala
            580                 585                 590 att cct gac ggt gat gtg aaa ggt cgc gtg gta gcg att tta ctt aat      1824
Ile Pro Asp Gly Asp Val Lys Gly Arg Val Val Ala Ile Leu Leu Asn
        595                 600                 605 gat gaa gtg aga tcg gca gac ctt ctg gcc att ctc aag gcg ctg aag      1872
Asp Glu Val Arg Ser Ala Asp Leu Leu Ala Ile Leu Lys Ala Leu Lys
610                 615                 620 gcc aaa ggc gtt cat gcc aaa ctg ctc tac tcc cga atg ggt gaa gtg      1920
Ala Lys Gly Val His Ala Lys Leu Leu Tyr Ser Arg Met Gly Glu Val
625                 630                 635                 640 act gcg gat gac ggt acg gtg ttg cct ata gcc gct acc ttt gcc ggt      1968
Thr Ala Asp Asp Gly Thr Val Leu Pro Ile Ala Ala Thr Phe Ala Gly
                645                 650                 655 gca cct tcg ctg acg gtc gat gcg gtc att gtc cct tgc ggc aat atc      2016
Ala Pro Ser Leu Thr Val Asp Ala Val Ile Val Pro Cys Gly Asn Ile
            660                 665                 670 gcg gat atc gct gac aac ggc gat gcc aac tac tac ctg atg gaa gcc      2064
Ala Asp Ile Ala Asp Asn Gly Asp Ala Asn Tyr Tyr Leu Met Glu Ala
        675                 680                 685 tac aaa cac ctt aaa ccg att gcg ctg gcg ggt gac gcg cgc aag ttt      2112
Tyr Lys His Leu Lys Pro Ile Ala Leu Ala Gly Asp Ala Arg Lys Phe
690                 695                 700 aaa gca aca atc aag atc gct gac cag ggt gaa gaa ggg att gtg gaa      2160
Lys Ala Thr Ile Lys Ile Ala Asp Gln Gly Glu Glu Gly Ile Val Glu
705                 710                 715                 720 gct gac agc gct gac ggt agt ttt atg gat gaa ctg cta acg ctg atg      2208
Ala Asp Ser Ala Asp Gly Ser Phe Met Asp Glu Leu Leu Thr Leu Met
                725                 730                 735 gca gca cac cgc gtg tgg tca cgc att cct aag att gac aaa att cct      2256
Ala Ala His Arg Val Trp Ser Arg Ile Pro Lys Ile Asp Lys Ile Pro
            740                 745                 750 gcc tga                                                               2262
Ala
```

<210> SEQ ID NO 24
<211> LENGTH: 753
<212> TYPE: PRT
<213> ORGANISM: Escherichia coli

<400> SEQUENCE: 24

| Met | Ser | Gln | His | Asn | Glu | Lys | Asn | Pro | His | Gln | Ser | Pro | Leu |
| 1 | | | | 5 | | | | | 10 | | | | 15 |

His Asp Ser Ser Glu Ala Lys Pro Gly Met Asp Ser Leu Ala Pro Glu
          20                  25                  30

Asp Gly Ser His Arg Pro Ala Glu Pro Thr Pro Pro Gly Ala Gln
              35                  40                  45

Pro Thr Ala Pro Gly Ser Leu Lys Ala Pro Asp Thr Arg Asn Glu Lys
 50                  55                  60

Leu Asn Ser Leu Glu Asp Val Arg Lys Gly Ser Glu Asn Tyr Ala Leu
 65                  70                  75                  80

Thr Thr Asn Gln Gly Val Arg Ile Ala Asp Asp Gln Asn Ser Leu Arg
                 85                  90                  95

Ala Gly Ser Arg Gly Pro Thr Leu Leu Glu Asp Phe Ile Leu Arg Glu
             100                 105                 110

Lys Ile Thr His Phe Asp His Glu Arg Ile Pro Glu Arg Ile Val His
         115                 120                 125

Ala Arg Gly Ser Ala Ala His Gly Tyr Phe Gln Pro Tyr Lys Ser Leu
     130                 135                 140

Ser Asp Ile Thr Lys Ala Asp Phe Leu Ser Asp Pro Asn Lys Ile Thr
145                 150                 155                 160

Pro Val Phe Val Arg Phe Ser Thr Val Gln Gly Gly Ala Gly Ser Ala
                165                 170                 175

Asp Thr Val Arg Asp Ile Arg Gly Phe Ala Thr Lys Phe Tyr Thr Glu
            180                 185                 190

Glu Gly Ile Phe Asp Leu Val Gly Asn Asn Thr Pro Ile Phe Phe Ile
        195                 200                 205

Gln Asp Ala His Lys Phe Pro Asp Phe Val His Ala Val Lys Pro Glu
    210                 215                 220

Pro His Trp Ala Ile Pro Gln Gly Gln Ser Ala His Asp Thr Phe Trp
225                 230                 235                 240

Asp Tyr Val Ser Leu Gln Pro Glu Thr Leu His Asn Val Met Trp Ala
                245                 250                 255

Met Ser Asp Arg Gly Ile Pro Arg Ser Tyr Arg Thr Met Glu Gly Phe
            260                 265                 270

Gly Ile His Thr Phe Arg Leu Ile Asn Ala Glu Gly Lys Ala Thr Phe
        275                 280                 285

Val Arg Phe His Trp Lys Pro Leu Ala Gly Lys Ala Ser Leu Val Trp
    290                 295                 300

Asp Glu Ala Gln Lys Leu Thr Gly Arg Asp Pro Asp Phe His Arg Arg
305                 310                 315                 320

Glu Leu Trp Glu Ala Ile Glu Ala Gly Asp Phe Pro Glu Tyr Glu Leu
                325                 330                 335

Gly Phe Gln Leu Ile Pro Glu Glu Asp Glu Phe Lys Phe Asp Phe Asp
            340                 345                 350

Leu Leu Asp Pro Thr Lys Leu Ile Pro Glu Glu Leu Val Pro Val Gln
        355                 360                 365

Arg Val Gly Lys Met Val Leu Asn Arg Asn Pro Asp Asn Phe Phe Ala
    370                 375                 380

Glu Asn Glu Gln Ala Ala Phe His Pro Gly His Ile Val Pro Gly Leu
385                 390                 395                 400

Asp Phe Thr Asn Asp Pro Leu Leu Gln Gly Arg Leu Phe Ser Tyr Thr
            405                 410                 415

Asp Thr Gln Ile Ser Arg Leu Gly Gly Pro Asn Phe His Glu Ile Pro
        420                 425                 430

Ile Asn Arg Pro Thr Cys Pro Tyr His Asn Phe Gln Arg Asp Gly Met
    435                 440                 445

His Arg Met Gly Ile Asp Thr Asn Pro Ala Asn Tyr Glu Pro Asn Ser
450                 455                 460

Ile Asn Asp Asn Trp Pro Arg Glu Thr Pro Gly Pro Lys Arg Gly
465                 470                 475                 480

Gly Phe Glu Ser Tyr Gln Glu Arg Val Glu Gly Asn Lys Val Arg Glu
                485                 490                 495

Arg Ser Pro Ser Phe Gly Glu Tyr Tyr Ser His Pro Arg Leu Phe Trp
            500                 505                 510

Leu Ser Gln Thr Pro Phe Glu Gln Arg His Ile Val Asp Gly Phe Ser
        515                 520                 525

Phe Glu Leu Ser Lys Val Val Arg Pro Tyr Ile Arg Glu Arg Val Val
530                 535                 540

Asp Gln Leu Ala His Ile Asp Leu Thr Leu Ala Gln Ala Val Ala Lys
545                 550                 555                 560

Asn Leu Gly Ile Glu Leu Thr Asp Asp Gln Leu Asn Ile Thr Pro Pro
                565                 570                 575

Pro Asp Val Asn Gly Leu Lys Lys Asp Pro Ser Leu Ser Leu Tyr Ala
            580                 585                 590

Ile Pro Asp Gly Asp Val Lys Gly Arg Val Val Ala Ile Leu Leu Asn
        595                 600                 605

Asp Glu Val Arg Ser Ala Asp Leu Leu Ala Ile Leu Lys Ala Leu Lys
    610                 615                 620

Ala Lys Gly Val His Ala Lys Leu Leu Tyr Ser Arg Met Gly Glu Val
625                 630                 635                 640

Thr Ala Asp Asp Gly Thr Val Leu Pro Ile Ala Ala Thr Phe Ala Gly
                645                 650                 655

Ala Pro Ser Leu Thr Val Asp Ala Val Ile Val Pro Cys Gly Asn Ile
            660                 665                 670

Ala Asp Ile Ala Asp Asn Gly Asp Ala Asn Tyr Tyr Leu Met Glu Ala
        675                 680                 685

Tyr Lys His Leu Lys Pro Ile Ala Leu Ala Gly Asp Ala Arg Lys Phe
    690                 695                 700

Lys Ala Thr Ile Lys Ile Ala Asp Gln Gly Glu Glu Gly Ile Val Glu
705                 710                 715                 720

Ala Asp Ser Ala Asp Gly Ser Phe Met Asp Glu Leu Leu Thr Leu Met
                725                 730                 735

Ala Ala His Arg Val Trp Ser Arg Ile Pro Lys Ile Asp Lys Ile Pro
            740                 745                 750

Ala

<210> SEQ ID NO 25
<211> LENGTH: 25
<212> TYPE: DNA
<213> ORGANISM: artificial sequence
<220> FEATURE:
<223> OTHER INFORMATION: Primer

<400> SEQUENCE: 25

```
gatctgactg gtggtctata gttag                                          25

<210> SEQ ID NO 26
<211> LENGTH: 25
<212> TYPE: DNA
<213> ORGANISM: artificial sequence
<220> FEATURE:
<223> OTHER INFORMATION: Primer

<400> SEQUENCE: 26
gtagttatca tgatgtgtaa gtaag                                          25

<210> SEQ ID NO 27
<211> LENGTH: 24
<212> TYPE: DNA
<213> ORGANISM: artificial sequence
<220> FEATURE:
<223> OTHER INFORMATION: primer

<400> SEQUENCE: 27
atgaccaaga tcaataactg gcag                                           24

<210> SEQ ID NO 28
<211> LENGTH: 25
<212> TYPE: DNA
<213> ORGANISM: artificial sequence
<220> FEATURE:
<223> OTHER INFORMATION: primer

<400> SEQUENCE: 28
ttactggttt tcacgcagcc agtcg                                          25

<210> SEQ ID NO 29
<211> LENGTH: 939
<212> TYPE: DNA
<213> ORGANISM: artificial sequence
<220> FEATURE:
<223> OTHER INFORMATION: synthetic construct

<400> SEQUENCE: 29
atgaccaaga tcaataactg gcaggattat cagggttcca gcctgaaacc tgaagatttc    60
gacaaattct gggacgagaa atcaacctg gttagcaatc accagttcga gtttgaattg    120
attgagaaga acctgagcag caaggtggtg aacttttacc acctgtggtt tacggctatc    180
gacggcgcga agattcacgc acaactgatt gttccgaaga atctgaaaga gaaataccccg    240 gcgatcctgc aatttcatgg ctatcactgt gactccggtg actgggttga caagattggt    300
attgttgccg aaggcaatgt ggttctggca ctggactgcc gtggtcaggg cggttttgagc   360 caagacaata tccaaaccat gggcatgacg atgaaaggtc tgattgtgcg tggtatcgat    420
gagggctatg agaatctgta ctatgtgcgc cagttcatgg acctgatcac ggctacgaag   480
attctgagcg agtttgactt cgttgacgaa accaatatct cggcacaagg cgcgtcgcag    540
ggtggcgcgt tggctgtggc gtgcgcggct ctgtctccgc tgattaagaa ggtgacggca    600
acgtacccgt tcttgagcga ttatcgcaag gcatatgagc tgggtgcgga agaaagcgcc    660
tttgaggagc tgccgtattg gtttcagttc aaagacccgc tgcacctgcg tgaagattgg    720
ttcttcaacc agctggagta tatcgacatt cagaatctgg ccctcgcat taaggcagag    780 gtgatttgga tcctgggtgg caaggatacc gtcgtcccgc cgattacgca aatggcagcg    840
tacaataaga tccagagcaa gaaaagccctg tatgttctgc cggagtatgg ccatgagtac    900
ttgccgaaga ttagcgactg gctgcgtgaa aaccagtaa                          939
```

<210> SEQ ID NO 30
<211> LENGTH: 5320
<212> TYPE: DNA
<213> ORGANISM: artificial sequence
<220> FEATURE:
<223> OTHER INFORMATION: plasmid

<400> SEQUENCE: 30

| | | | | | |
|---|---|---|---|---|---|
| gtttgacagc | ttatcatcga | ctgcacggtg | caccaatgct | tctggcgtca | ggcagccatc | 60 |
| ggaagctgtg | gtatggctgt | gcaggtcgta | aatcactgca | taattcgtgt | cgctcaaggc | 120 |
| gcactcccgt | tctggataat | gttttttgcg | ccgacatcat | aacggttctg | gcaaatattc | 180 |
| tgaaatgagc | tgttgacaat | taatcatccg | gctcgtataa | tgtgtggaat | tgtgagcgga | 240 |
| taacaatttc | acacaggaaa | cagcgccgct | gagaaaaagc | gaagcggcac | tgctctttaa | 300 |
| caatttatca | gacaatctgt | gtgggcactc | gaccggaatt | atcgattaac | tttattatta | 360 |
| aaaattaaag | aggtatatat | taatgtatcg | attaaataag | gaggaataaa | ccatggccct | 420 |
| tatgaccaag | atcaataact | ggcaggatta | tcagggttcc | agcctgaaac | ctgaagattt | 480 |
| cgacaaattc | tgggacgaga | aaatcaacct | ggttagcaat | caccagttcg | agtttgaatt | 540 |
| gattgagaag | aacctgagca | gcaaggtggt | gaacttttac | cacctgtggt | tacggctat | 600 |
| cgacggcgcg | aagattcacg | cacaactgat | tgttccgaag | aatctgaaag | agaaataccc | 660 |
| ggcgatcctg | caatttcatg | gctatcactg | tgactccggt | gactgggttg | acaagattgg | 720 |
| tattgttgcc | gaaggcaatg | tggttctggc | actggactgc | cgtggtcagg | gcggtttgag | 780 |
| ccaagacaat | atccaaacca | tgggcatgac | gatgaaaggt | ctgattgtgc | gtggtatcga | 840 |
| tgagggctat | gagaatctgt | actatgtgcg | ccagttcatg | gacctgatca | cggctacgaa | 900 |
| gattctgagc | gagtttgact | tcgttgacga | aaccaatatc | tcggcacaag | gcgcgtcgca | 960 |
| gggtggcgcg | ttggctgtgg | cgtgcgcggc | tctgtctccg | ctgattaaga | aggtgacggc | 1020 |
| aacgtacccg | ttcttgagcg | attatcgcaa | ggcatatgag | ctgggtgcgg | aagaaagcgc | 1080 |
| ctttgaggag | ctgccgtatt | ggtttcagtt | caaagacccg | ctgcacctgc | gtgaagattg | 1140 |
| gttcttcaac | cagctggagt | atatcgacat | tcagaatctg | gccctcgca | ttaaggcaga | 1200 |
| ggtgatttgg | atcctgggtg | gcaaggatac | cgtcgtcccg | ccgattacgc | aaatggcagc | 1260 |
| gtacaataag | atccagagca | agaaaagcct | gtatgttctg | ccggagtatg | gccatgagta | 1320 |
| cttgccgaag | attagcgact | ggctgcgtga | aaaccagtaa | aagggcgaat | tcgaagctta | 1380 |
| cgtagaacaa | aaactcatct | cagaagagga | tctgaatagc | gccgtcgacc | atcatcatca | 1440 |
| tcatcattga | gtttaaacgg | tctccagctt | ggctgttttg | gcggatgaga | gaagattttc | 1500 |
| agcctgatac | agattaaatc | agaacgcaga | agcggtctga | taaaacagaa | tttgcctggc | 1560 |
| ggcagtagcg | cggtggtccc | acctgacccc | atgccgaact | cagaagtgaa | acgccgtagc | 1620 |
| gccgatggta | gtgtggggtc | tccccatgcg | agagtaggga | actgccaggc | atcaaataaa | 1680 |
| acgaaaggct | cagtcgaaag | actgggcctt | tcgttttatc | tgttgtttgt | cggtgaacgc | 1740 |
| tctcctgagt | aggacaaatc | cgccgggagc | ggatttgaac | gttgcgaagc | aacggcccgg | 1800 |
| agggtggcgg | gcaggacgcc | cgccataaac | tgccaggcat | caaattaagc | agaaggccat | 1860 |
| cctgacggat | ggcctttttg | cgtttctaca | aactcttttt | gtttatttt | ctaaatacat | 1920 |
| tcaaatatgt | atccgctcat | gagacaataa | ccctgataaa | tgcttcaata | atattgaaaa | 1980 |
| aggaagagta | tgagtattca | acatttccgt | gtcgccctta | ttcccttttt | tgcggcattt | 2040 |
| tgccttcctg | tttttgctca | cccagaaacg | ctggtgaaag | taaaagatgc | tgaagatcag | 2100 |

```
ttgggtgcac gagtgggtta catcgaactg gatctcaaca gcggtaagat ccttgagagt   2160
tttcgccccg aagaacgttt tccaatgatg agcacttttta aagttctgct atgtggcgcg   2220
gtattatccc gtgttgacgc cgggcaagag caactcggtc gccgcataca ctattctcag   2280
aatgacttgg ttgagtactc accagtcaca gaaaagcatc ttacggatgg catgacagta   2340
agagaattat gcagtgctgc cataaccatg agtgataaca ctgcggccaa cttacttctg   2400
acaacgatcg gaggaccgaa ggagctaacc gcttttttgc acaacatggg ggatcatgta   2460
actcgccttg atcgttggga accggagctg aatgaagcca taccaaacga cgagcgtgac   2520
accacgatgc ctgtagcaat ggcaacaacg ttgcgcaaac tattaactgg cgaactactt   2580
actctagctt cccggcaaca attaatagac tggatggagg cggataaagt tgcaggacca   2640
cttctgcgct cggcccttcc ggctggctgg tttattgctg ataaatctgg agccggtgag   2700
cgtgggtctc gcggtatcat tgcagcactg gggccagatg gtaagccctc ccgtatcgta   2760
gttatctaca cgacggggag tcaggcaact atggatgaac gaaatagaca gatcgctgag   2820
ataggtgcct cactgattaa gcattggtaa ctgtcagacc aagtttactc atatatactt   2880
tagattgatt taaaacttca ttttttaattt aaaaggatct aggtgaagat cctttttgat   2940
aatctcatga ccaaaatccc ttaacgtgag ttttcgttcc actgagcgtc agaccccgta   3000
gaaaagatca aaggatcttc ttgagatcct ttttttctgc gcgtaatctg ctgcttgcaa   3060
acaaaaaaac caccgctacc agcggtggtt tgtttgccgg atcaagagct accaactctt   3120
tttccgaagg taactggctt cagcagagcg cagataccaa atactgtcct tctagtgtag   3180
ccgtagttag gccaccactt caagaactct gtagcaccgc ctacatacct cgctctgcta   3240
atcctgttac cagtggctgc tgccagtggc gataagtcgt gtcttaccgg gttggactca   3300
agacgatagt taccggataa ggcgcagcgg tcgggctgaa cggggggttc gtgcacacag   3360
cccagcttgg agcgaacgac ctacaccgaa ctgagatacc tacagcgtga gctatgagaa   3420
agcgccacgc ttcccgaagg gagaaaggcg gacaggtatc cggtaagcgg cagggtcgga   3480
acaggagagc gcacgaggga gcttccaggg ggaaacgcct ggtatcttta tagtcctgtc   3540
gggtttcgcc acctctgact tgagcgtcga ttttttgtgat gctcgtcagg ggggcggagc   3600
ctatggaaaa acgccagcaa cgcggccttt ttacggttcc tggccttttg ctggccttttt   3660 gctcacatgt tctttcctgc gttatcccct gattctgtgg ataaccgtat taccgccttt   3720
gagtgagctg ataccgctcg ccgcagccga acgaccgagc gcagcgagtc agtgagcgag   3780
gaagcggaag agcgcctgat gcggtatttt ctccttacgc atctgtgcgg tatttcacac   3840
cgcatatggt gcactctcag tacaatctgc tctgatgccg catagttaag ccagtataca   3900
ctccgctatc gctacgtgac tgggtcatgg ctgcgccccg acacccgcca acacccgctg   3960
acgcgccctg acgggcttgt ctgctcccgg catccgctta cagacaagct gtgaccgtct   4020
ccgggagctg catgtgtcag aggttttcac cgtcatcacc gaaacgcgcg aggcagcaga   4080
tcaattcgcg cgcgaaggcg aagcggcatg catttacgtt gacaccatcg aatggtgcaa   4140
aacctttcgc ggtatggcat gatagcgccc ggaagagagt caattcaggg tggtgaatgt   4200
gaaaccagta acgttatacg atgtcgcaga gtatgccggt gtctcttatc agaccgtttc   4260
ccgcgtggtg aaccaggcca gccacgtttc tgcgaaaacg cgggaaaaag tggaagcggc   4320
gatggcggag ctgaattaca ttcccaaccg cgtggcacaa caactggcgg gcaaacagtc   4380
gttgctgatt ggcgttgcca cctccagtct ggccctgcac gcgccgtcgc aaattgtcgc   4440
ggcgattaaa tctcgcgccg atcaactggg tgccagcgtg gtggtgtcga tggtagaacg   4500
```

```
aagcggcgtc gaagcctgta aagcggcggt gcacaatctt ctcgcgcaac gcgtcagtgg    4560
gctgatcatt aactatccgc tggatgacca ggatgccatt gctgtggaag ctgcctgcac    4620
taatgttccg gcgttatttc ttgatgtctc tgaccagaca cccatcaaca gtattatttt    4680
ctcccatgaa gacggtacgc gactgggcgt ggagcatctg gtcgcattgg gtcaccagca    4740
aatcgcgctg ttagcgggcc cattaagttc tgtctcggcg cgtctgcgtc tggctggctg    4800
gcataaatat ctcactcgca atcaaattca gccgatagcg gaacgggaag gcgactggag    4860
tgccatgtcc ggttttcaac aaaccatgca aatgctgaat gagggcatcg ttcccactgc    4920
gatgctggtt gccaacgatc agatggcgct gggcgcaatg cgcgccatta ccgagtccgg    4980
gctgcgcgtt ggtgcggata tctcggtagt gggatacgac gataccgaag acagctcatg    5040
ttatatcccg ccgtcaacca ccatcaaaca ggattttcgc ctgctggggc aaaccagcgt    5100
ggaccgcttg ctgcaactct ctcagggcca ggcggtgaag ggcaatcagc tgttgcccgt    5160
ctcactggtg aaaagaaaaa ccaccctggc gcccaatacg caaaccgcct ctccccgcgc    5220
gttggccgat tcattaatgc agctggcacg acaggtttcc cgactggaaa gcgggcagtg    5280
agcgcaacgc aattaatgtg agttagcgcg aattgatctg                         5320
```

<210> SEQ ID NO 31
<211> LENGTH: 27
<212> TYPE: DNA
<213> ORGANISM: artificial sequence
<220> FEATURE:
<223> OTHER INFORMATION: primer

<400> SEQUENCE: 31

```
atgccgttcc cggatctgat ccagccg                                         27
```

<210> SEQ ID NO 32
<211> LENGTH: 28
<212> TYPE: DNA
<213> ORGANISM: artificial sequence
<220> FEATURE:
<223> OTHER INFORMATION: primer

<400> SEQUENCE: 32

```
ttaacccaca ccgaacagac ggctcaac                                        28
```

<210> SEQ ID NO 33
<211> LENGTH: 972
<212> TYPE: DNA
<213> ORGANISM: artificial sequence
<220> FEATURE:
<223> OTHER INFORMATION: synthetic construct

<400> SEQUENCE: 33

```
atgccgttcc cggatctgat ccagccggaa ctgggcgcat acgtgagcag cgttggtatg      60
cctgatgact cgcgcaatt ctggacgagc acgattgctg aggcgcgtca agctggcggc     120
gaggtcagca tcgtccaggc ccaaaccacc ctgaaggctg ttcagagctt tgatgttacc    180
ttccctggct acgcggcca tccgatcaag ggctggttga tcctgccgac tcatcacaaa    240
ggtcgtctgc cgctggtggt gcaatacatc ggttatggtg cggccgtgg tttggcacat    300 gaacagctgc attgggccgc ctcgggcttt gcctatttcc gtatggatac ccgcggtcaa    360
ggttccgatt ggagcgtggg cgagactgcc gatccggtcg gtagcaccag cagcattccg    420
ggtttcatga cccgtggcgt tctggacaag aacgactatt actatcgtcg cttgtttacc    480
gacgcggttc gtgcgattga cgcgctgttg ggtctggact tgttgatcc ggagcgtatc    540
```

```
gcggtttgcg gtgactccca aggtggcggt attagcctgg cagttggcgg catcgacccg       600
cgtgtgaagg cggtgatgcc ggacgtcccg ttcttgtgtg actttccgcg tgcggtccag       660
accgcggtgc gtgatccgta tctggagatc gtccgtttcc tggctcagca ccgtgagaag       720
aaagcggcag tcttcgaaac cttgaactac tttgactgcg tcaatttcgc ccgtcgctcc       780
aaagccccgg cactgtttag cgtggccctg atggacgagg tttgccctcc aagcactgtc       840
tatggtgcgt ttaacgctta tgctggcgag aaaaccatta cggaatacga gtttaacaac       900
cacgagggcg gtcagggtta ccaggaacgt caacaaatga cctggttgag ccgtctgttc       960
ggtgtgggtt aa                                                           972

<210> SEQ ID NO 34
<211> LENGTH: 5353
<212> TYPE: DNA
<213> ORGANISM: artificial sequence
<220> FEATURE:
<223> OTHER INFORMATION: plasmid

<400> SEQUENCE: 34
gtttgacagc ttatcatcga ctgcacggtg caccaatgct tctggcgtca ggcagccatc        60
ggaagctgtg gtatggctgt gcaggtcgta aatcactgca taattcgtgt cgctcaaggc       120
gcactcccgt tctggataat gttttttgcg ccgacatcat aacggttctg gcaaatattc       180
tgaaatgagc tgttgacaat taatcatccg gctcgtataa tgtgtggaat tgtgagcgga       240
taacaatttc acacaggaaa cagcgccgct gagaaaaagc gaagcggcac tgctctttaa       300
caatttatca gacaatctgt gtgggcactc gaccggaatt atcgattaac tttattatta       360
aaaattaaag aggtatatat taatgtatcg attaaataag gaggaataaa ccatggccct       420
tatgccgttc ccggatctga tccagccgga actgggcgca tacgtgagca gcgttggtat       480
gcctgatgac ttcgcgcaat tctggacgag cacgattgct gaggcgcgtc aagctggcgg       540
cgaggtcagc atcgtccagg cccaaaccac cctgaaggct gttcagagct tgatgttac       600 cttccctggc tacggcggcc atccgatcaa gggctggttg atcctgccga ctcatcacaa       660
aggtcgtctg ccgctggtgg tgcaatacat cggttatggt ggcggccgtg gtttggcaca       720
tgaacagctg cattgggccg cctcgggctt tgcctatttc cgtatggata cccgcggtca       780
aggttccgat tggagcgtgg gcgagactgc cgatccggtc ggtagcacca gcagcattcc       840
gggtttcatg acccgtggcg ttctggacaa gaacgactat tactatcgtc gcttgtttac       900
cgacgcggtt cgtgcgattg acgcgctgtt gggtctggac tttgttgatc cggagcgtat       960 cgcggttgc ggtgactccc aaggtggcgg tattagcctg gcagttggcg gcatcgaccc      1020
gcgtgtgaag gcggtgatgc cggacgtccc gttcttgtgt gactttccgc gtgcggtcca      1080
gaccgcggtg cgtgatccgt atctggagat cgtccgtttc ctggctcagc accgtgagaa      1140
gaaagcggca gtcttcgaaa ccttgaacta ctttgactgc gtcaatttcg cccgtcgctc      1200
caaagccccg gcactgttta gcgtggccct gatggacgag gtttgccctc aagcactgt      1260 ctatggtgcg tttaacgctt atgctggcga gaaaaccatt acggaatacg agtttaacaa      1320
ccacgagggc ggtcagggtt accaggaacg tcaacaaatg acctggttga gccgtctgtt      1380
cggtgtgggt taaagggcg aattcgaagc ttacgtagaa caaaaactca tctcagaaga      1440
ggatctgaat agcgccgtcg accatcatca tcatcatcat tgagtttaaa cggtctccag      1500
cttggctgtt ttggcggatg agagaagatt ttcagcctga tacagattaa atcagaacgc      1560
agaagcggtc tgataaaaca gaatttgcct ggcggcagta gcgcggtggt cccacctgac      1620
```

```
cccatgccga actcagaagt gaaacgccgt agcgccgatg gtagtgtggg gtctccccat    1680
gcgagagtag ggaactgcca ggcatcaaat aaaacgaaag gctcagtcga aagactgggc    1740
ctttcgtttt atctgttgtt tgtcggtgaa cgctctcctg agtaggacaa atccgccggg    1800
agcggatttg aacgttgcga agcaacggcc cggagggtgg cgggcaggac gcccgccata    1860
aactgccagg catcaaatta agcagaaggc catcctgacg gatggccttt ttgcgtttct    1920
acaaactctt tttgtttatt tttctaaata cattcaaata tgtatccgct catgagacaa    1980
taaccctgat aaatgcttca ataatattga aaaggaaga gtatgagtat tcaacatttc     2040
cgtgtcgccc ttattccctt ttttgcggca ttttgccttc ctgttttgc tcacccagaa     2100
acgctggtga agtaaaaga tgctgaagat cagttgggtg cacgagtggg ttacatcgaa     2160
ctggatctca acagcggtaa gatccttgag agttttcgcc ccgaagaacg ttttccaatg    2220
atgagcactt ttaaagttct gctatgtggc gcggtattat cccgtgttga cgccgggcaa    2280
gagcaactcg gtcgccgcat acactattct cagaatgact tggttgagta ctcaccagtc    2340
acagaaaagc atcttacgga tggcatgaca gtaagagaat tatgcagtgc tgccataacc    2400
atgagtgata acactgcggc caacttactt ctgacaacga tcggaggacc gaaggagcta    2460
accgctttt tgcacaacat gggggatcat gtaactcgcc ttgatcgttg ggaaccggag     2520
ctgaatgaag ccataccaaa cgacgagcgt gacaccacga tgcctgtagc aatggcaaca    2580
acgttgcgca aactattaac tggcgaacta cttactctag cttcccggca acaattaata    2640
gactggatgg aggcggataa agttgcagga ccacttctgc gctcggccct tccggctggc    2700
tggtttattg ctgataaatc tggagccggt gagcgtgggt ctcgcggtat cattgcagca    2760
ctggggccag atggtaagcc ctcccgtatc gtagttatct acacgacggg gagtcaggca    2820
actatggatg aacgaaatag acagatcgct gagataggtg cctcactgat taagcattgg    2880
taactgtcag accaagttta ctcatatata ctttagattg atttaaaact tcattttaa     2940
tttaaaagga tctaggtgaa gatccttttt gataatctca tgaccaaaat cccttaacgt    3000
gagttttcgt tccactgagc gtcagacccc gtagaaaaga tcaaaggatc ttcttgagat    3060
cctttttttc tgcgcgtaat ctgctgcttg caaacaaaaa aaccaccgct accagcggtg    3120
gtttgtttgc cggatcaaga gctaccaact ctttttccga aggtaactgg cttcagcaga    3180
gcgcagatac caaatactgt ccttctagtg tagccgtagt taggccacca cttcaagaac    3240
tctgtagcac cgcctacata cctcgctctg ctaatcctgt taccagtggc tgctgccagt    3300
ggcgataagt cgtgtcttac cgggttggac tcaagacgat agttaccgga taaggcgcag    3360
cggtcgggct gaacggggg ttcgtgcaca cagcccagct tggagcgaac gacctacacc     3420
gaactgagat acctacagcg tgagctatga gaaagcgcca cgcttcccga agggagaaag    3480
gcggacaggt atccggtaag cggcagggtc ggaacaggag agcgcacgag ggagcttcca    3540
gggggaaacg cctggtatct ttatagtcct gtcgggtttc gccacctctg acttgagcgt    3600
cgatttttgt gatgctcgtc agggggggcgg agcctatgga aaaacgccag caacgcggcc    3660
tttttacggt tcctggcctt ttgctggcct tttgctcaca tgttctttcc tgcgttatcc    3720
cctgattctg tggataaccg tattaccgcc tttgagtgag ctgataccgc tcgccgcagc    3780
cgaacgaccg agcgcagcga gtcagtgagc gaggaagcgg aagagcgcct gatgcggtat    3840
tttctcctta cgcatctgtg cggtatttca caccgcatat ggtgcactct cagtacaatc    3900
tgctctgatg ccgcatagtt aagccagtat acactccgct atcgctacgt gactgggtca    3960
tggctgcgcc ccgacacccg ccaacacccg ctgacgcgcc ctgacgggct tgtctgctcc    4020
```

```
cggcatccgc ttacagacaa gctgtgaccg tctccgggag ctgcatgtgt cagaggtttt   4080
caccgtcatc accgaaacgc gcgaggcagc agatcaattc gcgcgcgaag gcgaagcggc   4140
atgcatttac gttgacacca tcgaatggtg caaaacctttt cgcggtatgg catgatagcg  4200
cccggaagag agtcaattca gggtggtgaa tgtgaaacca gtaacgttat acgatgtcgc   4260
agagtatgcc ggtgtctctt atcagaccgt ttcccgcgtg gtgaaccagg ccagccacgt   4320
ttctgcgaaa acgcgggaaa aagtggaagc ggcgatggcg gagctgaatt acattcccaa   4380
ccgcgtggca caacaactgg cgggcaaaca gtcgttgctg attggcgttg ccacctccag   4440
tctggccctg cacgcgccgt cgcaaattgt cgcggcgatt aaatctcgcg ccgatcaact   4500
gggtgccagc gtggtggtgt cgatggtaga acgaagcggc gtcgaagcct gtaaagcggc   4560
ggtgcacaat cttctcgcgc aacgcgtcag tgggctgatc attaactatc cgctggatga   4620
ccaggatgcc attgctgtgg aagctgcctg cactaatgtt ccggcgttat tcttgatgt    4680 ctctgaccag acacccatca acagtattat tttctcccat gaagacggta cgcgactggg   4740
cgtggagcat ctggtcgcat gggtcacca gcaaatcgcg ctgttagcgg cccattaag    4800 ttctgtctcg gcgcgtctgc gtctggctgg ctggcataaa tatctcactc gcaatcaaat   4860
tcagccgata gcggaacggg aaggcgactg gagtgccatg tccggttttc aacaaaccat   4920
gcaaatgctg aatgagggca tcgttcccac tgccgatgctg gttgccaacg atcagatggc  4980
gctgggcgca atgcgcgcca ttaccgagtc cgggctgcgc gttggtgcgg atatctcggt   5040
agtgggatac gacgataccg aagacagctc atgttatatc ccgccgtcaa ccaccatcaa   5100
acaggatttt cgcctgctgg ggcaaaccag cgtggaccgc ttgctgcaac tctctcaggg   5160
ccaggcggtg aagggcaatc agctgttgcc cgtctcactg gtgaaaagaa aaaccaccct   5220
ggcgcccaat acgcaaaccg cctctccccg cgcgttggcc gattcattaa tgcagctggc   5280
acgacaggtt tcccgactgg aaagcgggca gtgagcgcaa cgcaattaat gtgagttagc   5340
gcgaattgat ctg                                                     5353
```

<210> SEQ ID NO 35
<211> LENGTH: 27
<212> TYPE: DNA
<213> ORGANISM: artificial sequence
<220> FEATURE:
<223> OTHER INFORMATION: primer

<400> SEQUENCE: 35
atgtttgata tgccgctggc ccagttg                                        27

<210> SEQ ID NO 36
<211> LENGTH: 26
<212> TYPE: DNA
<213> ORGANISM: artificial sequence
<220> FEATURE:
<223> OTHER INFORMATION: primer

<400> SEQUENCE: 36
ttatttgaca ttgcgctttt gaatcg                                         26

<210> SEQ ID NO 37
<211> LENGTH: 990
<212> TYPE: DNA
<213> ORGANISM: artificial sequence
<220> FEATURE:
<223> OTHER INFORMATION: synthetic construct

<400> SEQUENCE: 37

```
atgtttgata tgccgctggc ccagttgcag aaatacatgg gtacgaaccc taaaccggca      60
gattttgcag acttttggag ccgtgctctg gaggagctga gcgcccagtc gctgcactac     120
gagctgatcc cagcgacgtt ccagactacc gtcgcaagct gctaccacct gtactttacg     180
ggtgttggcg gtgcacgcgt tcactgtcaa ctggtgaaac cgcgcgagca aaaacagaaa     240
ggtccgggcc tggtgtggtt tcatggctat cataccaata gcggtgactg ggtcgacaag     300
ctggcatacg cggcagcagg cttcaccgtt ttggcgatgg actgccgtgg tcaaggtggt     360
aagagcgagg ataatctgca agtgaaaggc ccgaccctga agggccatat cattcgtggt     420
atcgaggacc cgaatccgca tcatttgtat taccgtaacg tgtttctgga cactgtccaa     480
gctgtccgta ttctgtgttc catggatcac atcgatcgtg aacgcatcgg tgtgtatggc     540
gctagccagg gtggtgccct ggcgctggcg tgtgcggcgc tggagccgtc tgtcgttaag     600
aaagccgttg ttctgtaccc attcctgagc gactataagc gtgcgcaaga gctggacatg     660
aaaaacacgg cgtatgaaga atccactac tatttccgtt cctggatcc gacccacgaa     720 cgcgaggaag aggttttcta taagctgggc tacattgaca tccagctgct ggcggatcgt     780
atctgcgcga cgtgctgtg ggccgttgct ctggaagatc acatttgccc tccaagcacc     840
cagttcgcgg tgtataacaa gattaagtcc aagaaagata tggtgttgtt ctacgaatac     900
ggtcatgaat acctgccgac catgggcgat cgcgcctatt tgttcttctg tccgatttc      960 tttccgattc aaaagcgcaa tgtcaaataa                                       990
```

<210> SEQ ID NO 38  
<211> LENGTH: 5371  
<212> TYPE: DNA  
<213> ORGANISM: artificial sequence  
<220> FEATURE:  
<223> OTHER INFORMATION: plasmid

<400> SEQUENCE: 38

```
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatggccct     420
tatgtttgat atgccgctgg cccagttgca gaaatacatg ggtacgaacc ctaaaccggc     480
agattttgca gacttttgga gccgtgctct ggaggagctg agcgcccagt cgctgcacta     540
cgagctgatc ccagcgacgt tccagactac gtcgcaagc tgctaccacc tgtactttac     600
gggtgttggc ggtgcacgcg ttcactgtca actggtgaaa ccgcgcgagc aaaaacagaa     660
aggtccgggc ctggtgtggt tcatggcta tcataccaat agcggtgact gggtcgacaa     720
gctggcatac gcggcagcag gcttcaccgt tttggcgatg gactgccgtg gtcaaggtgg     780
taagagcgag gataatctgc aagtgaaagg cccgaccctg aagggccata tcattcgtgg     840
tatcgaggac ccgaatccgc atcatttgta ttaccgtaac gtgtttctgg acactgtcca     900
agctgtccgt attctgtgtt ccatggatca catcgatcgt gaacgcatcg gtgtgtatgg     960
cgctagccag ggtggtgccc tggcgctggc gtgtgcggcg ctggagccgt ctgtcgttaa    1020
gaaagccgtt gttctgtacc cattcctgag cgactataag cgtgcgcaag agctggacat    1080
```

```
gaaaaacacg gcgtatgaag aaatccacta ctatttccgt ttcctggatc cgacccacga   1140
acgcgaggaa gaggttttct ataagctggg ctacattgac atccagctgc tggcggatcg   1200
tatctgcgcg gacgtgctgt gggccgttgc tctggaagat cacatttgcc ctccaagcac   1260
ccagttcgcg gtgtataaca agattaagtc caagaaagat atggtgttgt tctacgaata   1320
cggtcatgaa tacctgccga ccatgggcga tcgcgcctat ttgttcttct gtccgatttt   1380 cttttccgatt caaaagcgca atgtcaaata aaagggcgaa ttcgaagctt acgtagaaca   1440
aaaactcatc tcagaagagg atctgaatag cgccgtcgac catcatcatc atcatcattg   1500
agtttaaacg gtctccagct tggctgtttt ggcggatgag agaagatttt cagcctgata   1560
cagattaaat cagaacgcag aagcggtctg ataaaacaga atttgcctgg cggcagtagc   1620
gcggtggtcc cacctgaccc catgccgaac tcagaagtga acgccgtag cgccgatggt   1680 agtgtggggt ctccccatgc gagagtaggg aactgccagg catcaaataa aacgaaaggc   1740
tcagtcgaaa gactgggcct ttcgttttat ctgttgtttg tcggtgaacg ctctcctgag   1800
taggacaaat ccgccgggag cggatttgaa cgttgcgaag caacggcccg gagggtggcg   1860
ggcaggacgc ccgccataaa ctgccaggca tcaaattaag cagaaggcca tcctgacgga   1920
tggccttttt gcgttctac aaactctttt tgtttatttt tctaaataca ttcaaatatg   1980
tatccgctca tgagacaata accctgataa atgcttcaat aatattgaaa aggaagagt   2040 atgagtattc aacatttccg tgtcgccctt attcccttttt ttgcggcatt ttgccttcct   2100 gttttttgctc acccagaaac gctggtgaaa gtaaaagatg ctgaagatca gttgggtgca   2160
cgagtgggtt acatcgaact ggatctcaac agcggtaaga tccttgagag ttttcgcccc   2220
gaagaacgtt ttccaatgat gagcactttt aaagttctgc tatgtggcgc ggtattatcc   2280
cgtgttgacg ccgggcaaga gcaactcggt cgccgcatac actattctca gaatgacttg   2340
gttgagtact caccagtcac agaaaagcat cttacggatg gcatgacagt aagagaatta   2400
tgcagtgctg ccataaccat gagtgataac actgcggcca acttacttct gacaacgatc   2460
ggaggaccga aggagctaac cgcttttttg cacaacatgg gggatcatgt aactcgcctt   2520
gatcgttggg aaccggagct gaatgaagcc ataccaaacg acgagcgtga caccacgatg   2580
cctgtagcaa tggcaacaac gttgcgcaaa ctattaactg gcgaactact tactctagct   2640
tcccggcaac aattaataga ctggatggag gcggataaag ttgcaggacc acttctgcgc   2700
tcggcccttc cggctggctg gtttattgct gataaatctg gagccggtga gcgtgggtct   2760
cgcggtatca ttgcagcact ggggccagat ggtaagccct cccgtatcgt agttatctac   2820
acgacgggga gtcaggcaac tatgatgaa cgaaatagac agatcgctga gataggtgcc   2880
tcactgatta agcattggta actgtcagac caagtttact catatatact ttagattgat   2940
ttaaaacttc atttttaatt taaaaggatc taggtgaaga tccttttga taatctcatg   3000 accaaaatcc cttaacgtga gttttcgttc cactgagcgt cagaccccgt agaaaagatc   3060
aaaggatctt cttgagatcc ttttttttctg cgcgtaatct gctgcttgca acaaaaaaa   3120 ccaccgctac cagcggtggt ttgtttgccg gatcaagagc taccaactct ttttccgaag   3180
gtaactggct tcagcagagc gcagatacca atactgtcc ttctagtgta gccgtagtta   3240
ggccaccact tcaagaactc tgtagcaccg cctacatacc tcgctctgct aatcctgtta   3300
ccagtggctg ctgccagtgg cgataagtcg tgtcttaccg ggttggactc aagacgatag   3360
ttaccggata aggcgcagcg gtcgggctga acggggggtt cgtgcacaca gcccagcttg   3420
gagcgaacga cctacaccga actgagatac ctacagcgtg agctatgaga aagcgccacg   3480
```

```
cttcccgaag ggagaaaggc ggacaggtat ccggtaagcg gcagggtcgg aacaggagag   3540
cgcacgaggg agcttccagg gggaaacgcc tggtatcttt atagtcctgt cgggtttcgc   3600
cacctctgac ttgagcgtcg attttttgtga tgctcgtcag gggggcggag cctatggaaa  3660
aacgccagca acgcggcctt tttacggttc ctggccttt gctggccttt tgctcacatg    3720
ttctttcctg cgttatcccc tgattctgtg ataaccgta ttaccgcctt tgagtgagct    3780
gataccgctc gccgcagccg aacgaccgag cgcagcgagt cagtgagcga ggaagcggaa   3840
gagcgcctga tgcggtattt tctccttacg catctgtgcg gtatttcaca ccgcatatgg   3900
tgcactctca gtacaatctg ctctgatgcc gcatagttaa gccagtatac actccgctat   3960
cgctacgtga ctgggtcatg gctgcgcccc gacacccgcc aacacccgct gacgcgccct   4020
gacgggcttg tctgctcccg gcatccgctt acagacaagc tgtgaccgtc tccgggagct   4080
gcatgtgtca gaggttttca ccgtcatcac cgaaacgcgc gaggcagcag atcaattcgc   4140
gcgcgaaggc gaagcggcat gcatttacgt tgacaccatc gaatggtgca aaacctttcg   4200
cggtatggca tgatagcgcc cggaagagag tcaattcagg gtggtgaatg tgaaaccagt   4260
aacgttatac gatgtcgcag agtatgccgg tgtctcttat cagaccgttt ccgcgtggtg  4320
gaaccaggcc agccacgttt ctgcgaaaac gcgggaaaaa gtggaagcgg cgatggcgga   4380
gctgaattac attcccaacc gcgtggcaca acaactggcg gcaaacagt cgttgctgat    4440
tggcgttgcc acctccagtc tggccctgca cgcgccgtcg caaattgtcg cggcgattaa   4500
atctcgcgcc gatcaactgg gtgccagcgt ggtggtgtcg atggtagaac gaagcggcgt   4560
cgaagcctgt aaagcggcgg tgcacaatct tctcgcgcaa cgcgtcagtg gctgatcat    4620
taactatccg ctggatgacc aggatgccat tgctgtggaa gctgcctgca ctaatgttcc   4680
ggcgttattt cttgatgtct ctgaccagac acccatcaac agtattattt tctcccatga   4740
agacggtacg cgactgggcg tggagcatct ggtcgcattg ggtcaccagc aaatcgcgct   4800
gttagcgggc ccattaagtt ctgtctcggc gcgtctgcgt ctggctggct ggcataaata   4860
tctcactcgc aatcaaattc agccgatagc ggaacgggaa ggcgactgga gtgccatgtc   4920
cggttttcaa caaaccatgc aaatgctgaa tgagggcatc gttcccactg cgatgctggt   4980
tgccaacgat cagatggcgc tgggcgcaat gcgcgccatt accgagtccg ggctgcgcgt   5040
tggtgcggat atctcggtag tgggatacga cgataccgaa gacagctcat gttatatccc   5100
gccgtcaacc accatcaaac aggattttcg cctgctgggg caaaccagcg tggaccgctt   5160
gctgcaactc tctcagggcc aggcggtgaa gggcaatcag ctgttgcccg tctcactggt   5220
gaaaagaaaa accaccctgg cgcccaatac gcaaaccgcc tctccccgcg cgttggccga   5280
ttcattaatg cagctggcac gacaggtttc ccgactggaa agcgggcagt gagcgcaacg   5340
caattaatgt gagttagcgc gaattgatct g                                  5371
```

<210> SEQ ID NO 39  
<211> LENGTH: 325  
<212> TYPE: PRT  
<213> ORGANISM: Thermotoga neapolitana
<400> SEQUENCE: 39

Met Ala Phe Phe Asp Met Pro Leu Glu Glu Leu Lys Lys Tyr Arg Pro  
1               5                   10                  15

Glu Arg Tyr Glu Glu Lys Asp Phe Asp Glu Phe Trp Arg Glu Thr Leu  
            20                  25                  30

Lys Glu Ser Glu Gly Phe Pro Leu Asp Pro Val Phe Glu Lys Val Asp

```
                35                  40                  45
Phe His Leu Lys Thr Val Glu Thr Tyr Asp Val Thr Phe Ser Gly Tyr
 50                  55                  60

Arg Gly Gln Arg Ile Lys Gly Trp Leu Val Pro Lys Leu Ala Glu
 65                  70                  75                  80

Glu Lys Leu Pro Cys Val Val Gln Tyr Ile Gly Tyr Asn Gly Gly Arg
                 85                  90                  95

Gly Phe Pro His Asp Trp Leu Phe Trp Pro Ser Met Gly Tyr Ile Cys
                100                 105                 110

Phe Val Met Asp Thr Arg Gly Gln Gly Ser Gly Trp Met Lys Gly Asp
                115                 120                 125

Thr Pro Asp Tyr Pro Glu Gly Pro Val Asp Pro Gln Tyr Pro Gly Phe
                130                 135                 140

Met Thr Arg Gly Ile Leu Asp Pro Gly Thr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Ala Gly Ser Gln Gly Gly Gly
                180                 185                 190

Ile Ala Leu Ala Val Ser Ala Leu Ser Asn Arg Val Lys Ala Leu Leu
                195                 200                 205

Cys Asp Val Pro Phe Leu Cys His Phe Arg Arg Ala Val Gln Leu Val
                210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
                260                 265                 270

Met Asp Thr Ile Cys Pro Pro Ser Thr Val Phe Ala Ala Tyr Asn His
                275                 280                 285

Tyr Ala Gly Pro Lys Glu Ile Arg Ile Tyr Pro Tyr Asn Asn His Glu
                290                 295                 300

Gly Gly Gly Ser Phe Gln Ala Ile Glu Gln Val Lys Phe Leu Lys Arg
305                 310                 315                 320

Leu Phe Glu Glu Gly
                325

<210> SEQ ID NO 40
<211> LENGTH: 325
<212> TYPE: PRT
<213> ORGANISM: Thermotoga maritima MSB8

<400> SEQUENCE: 40

Met Ala Phe Phe Asp Leu Pro Leu Glu Glu Leu Lys Lys Tyr Arg Pro
 1               5                  10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
                35                  40                  45

Ser His Leu Lys Thr Val Glu Ala Tyr Asp Val Thr Phe Ser Gly Tyr
                50                  55                  60

Arg Gly Gln Arg Ile Lys Gly Trp Leu Val Pro Lys Leu Glu Glu
 65                  70                  75                  80

Glu Lys Leu Pro Cys Val Val Gln Tyr Ile Gly Tyr Asn Gly Gly Arg
```

```
                85                  90                  95
Gly Phe Pro His Asp Trp Leu Phe Trp Pro Ser Met Gly Tyr Ile Cys
                100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
        130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Ala Lys Ala Leu Leu
        195                 200                 205

Cys Asp Val Pro Phe Leu Cys His Phe Arg Arg Ala Val Gln Leu Val
            210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Cys Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 41
<211> LENGTH: 320
<212> TYPE: PRT
<213> ORGANISM: Bacillus pumilus

<400> SEQUENCE: 41

Met Gln Leu Phe Asp Leu Ser Leu Glu Glu Leu Lys Lys Tyr Lys Pro
1               5                   10                  15

Lys Lys Thr Ala Arg Pro Asp Phe Ser Asp Phe Trp Lys Lys Ser Leu
            20                  25                  30

Glu Glu Leu Arg Gln Val Glu Ala Glu Pro Thr Leu Gly Ser Tyr Asp
        35                  40                  45

Tyr Pro Val Lys Gly Val Lys Val Tyr Arg Leu Thr Tyr Gln Ser Phe
    50                  55                  60

Gly His Ser Lys Ile Glu Gly Phe Tyr Ala Val Pro Asp Gln Thr Gly
65                  70                  75                  80

Pro His Pro Ala Leu Val Arg Phe His Gly Tyr Asn Ala Ser Tyr Asp
                85                  90                  95

Gly Gly Ile His Asp Ile Val Asn Trp Ala Leu His Gly Tyr Ala Thr
            100                 105                 110

Phe Gly Met Leu Val Arg Gly Gln Gly Ser Glu Asp Thr Ser Val
        115                 120                 125

Thr Pro Gly Gly His Ala Leu Gly Trp Met Thr Lys Gly Ile Leu Ser
```

```
                130              135              140
Lys Asp Thr Tyr Tyr Tyr Arg Gly Val Tyr Leu Asp Ala Val Arg Ala
145                 150                 155                 160

Leu Glu Val Ile Gln Ser Phe Pro Glu Val Asp Glu His Arg Ile Gly
                165                 170                 175

Val Ile Gly Gly Ser Gln Gly Gly Ala Leu Ala Ile Ala Ala Ala Ala
                180                 185                 190

Leu Ser Asp Ile Pro Lys Val Val Val Ala Asp Tyr Pro Tyr Leu Ser
            195                 200                 205

Asn Phe Glu Arg Ala Val Asp Val Ala Leu Glu Gln Pro Tyr Leu Glu
            210                 215                 220

Ile Asn Ser Tyr Phe Arg Arg Asn Ser Asp Pro Lys Val Glu Glu Lys
225                 230                 235                 240

Ala Phe Glu Thr Leu Ser Tyr Phe Asp Leu Ile Asn Leu Ala Gly Trp
                245                 250                 255

Val Lys Gln Pro Thr Leu Met Ala Ile Gly Leu Ile Asp Lys Ile Thr
                260                 265                 270

Pro Pro Ser Thr Val Phe Ala Ala Tyr Asn His Leu Glu Thr Asp Lys
            275                 280                 285

Asp Leu Lys Val Tyr Arg Tyr Phe Gly His Glu Phe Ile Pro Ala Phe
    290                 295                 300

Gln Thr Glu Lys Leu Ser Phe Leu Gln Lys His Leu Leu Leu Ser Thr
305                 310                 315                 320
```